US011351242B1

(12) United States Patent
Panther et al.

(10) Patent No.: US 11,351,242 B1
(45) Date of Patent: Jun. 7, 2022

(54) HMPV/HPIV3 MRNA VACCINE COMPOSITION

(71) Applicant: ModernaTX, Inc., Cambridge, MA (US)

(72) Inventors: Lori Panther, Cambridge, MA (US); Christine Shaw, Reading, MA (US); Igor Smolenov, Cambridge, MA (US); Michael Watson, Cambridge, MA (US); Tal Zaks, Newton, MA (US)

(73) Assignee: ModernaTX, Inc., Cambridge, MA (US)

( * ) Notice: Subject to any disclaimer, the term of this patent is extended or adjusted under 35 U.S.C. 154(b) by 117 days.

(21) Appl. No.: 16/788,182

(22) Filed: Feb. 11, 2020

Related U.S. Application Data

(60) Provisional application No. 62/877,937, filed on Jul. 24, 2019, provisional application No. 62/811,381, filed on Feb. 27, 2019, provisional application No. 62/804,482, filed on Feb. 12, 2019.

(51) Int. Cl.
*A61K 39/12* (2006.01)
*A61K 9/51* (2006.01)
*A61K 39/00* (2006.01)

(52) U.S. Cl.
CPC ............... *A61K 39/12* (2013.01); *A61K 9/51* (2013.01); *A61K 2039/53* (2013.01); *A61K 2039/545* (2013.01); *A61K 2039/575* (2013.01); *A61K 2039/64* (2013.01)

(58) Field of Classification Search
None
See application file for complete search history.

(56) References Cited

U.S. PATENT DOCUMENTS

| | | |
|---|---|---|
| 3,906,092 A | 9/1975 | Hilleman et al. |
| 4,790,987 A | 12/1988 | Comparts et al. |
| 5,169,628 A | 12/1992 | Wathen |
| 5,427,782 A | 6/1995 | Compans et al. |
| 6,225,091 B1 | 5/2001 | Klein et al. |
| 6,500,419 B1 | 12/2002 | Hone et al. |
| 6,514,948 B1 | 2/2003 | Raz et al. |
| 6,610,044 B2 | 8/2003 | Mathiesen |
| 7,001,890 B1 | 2/2006 | Wagner et al. |
| 7,208,161 B1 | 4/2007 | Murphy et al. |
| 7,449,324 B2 | 11/2008 | Fouchier et al. |
| 7,531,342 B2 | 5/2009 | Fouchier et al. |
| 7,671,186 B2 | 3/2010 | Klein et al. |
| 7,704,720 B2 | 4/2010 | Tang et al. |
| 8,217,016 B2 | 7/2012 | Hoerr et al. |
| 8,252,289 B2 | 8/2012 | Eleouët et al. |
| 8,569,256 B2 | 10/2013 | Heyes et al. |
| 8,609,142 B2 | 12/2013 | Troiano et al. |
| 8,613,954 B2 | 12/2013 | Zale et al. |
| 8,617,608 B2 | 12/2013 | Zale et al. |
| 8,710,200 B2 | 4/2014 | Schrum et al. |
| 8,722,341 B2 | 5/2014 | Fouchier et al. |
| 8,734,832 B2 | 5/2014 | O'Hagan et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,841,433 B2 | 9/2014 | Fouchier et al. |
| 8,889,146 B2 | 11/2014 | Blais et al. |
| 8,927,206 B2 | 1/2015 | De Jong et al. |
| 8,999,380 B2 | 4/2015 | Bancel et al. |
| 9,192,661 B2 | 11/2015 | Jain et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,376,726 B2 | 6/2016 | Fouchier et al. |
| 9,464,124 B2 | 10/2016 | Bancel et al. |
| 9,512,456 B2 | 12/2016 | Wang et al. |
| 9,567,653 B2 | 2/2017 | Fouchier et al. |
| 9,597,380 B2 | 3/2017 | Chakraborty et al. |
| 9,623,095 B2 | 4/2017 | Kallen et al. |
| 9,669,089 B2 | 6/2017 | Thess et al. |
| 9,790,531 B2 | 10/2017 | Wang et al. |
| 9,868,691 B2 | 1/2018 | Benenato et al. |
| 9,872,900 B2 | 1/2018 | Ciaramella et al. |
| 9,937,196 B2 | 4/2018 | Jain et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |

(Continued)

FOREIGN PATENT DOCUMENTS

| | | |
|---|---|---|
| AU | 652831 B2 | 9/1994 |
| CA | 2473135 | 6/2003 |

(Continued)

OTHER PUBLICATIONS

U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 90/014,395, filed Oct. 24, 2019, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/450,882, filed Jun. 24, 2019, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.

(Continued)

*Primary Examiner* — Stacy B Chen
(74) *Attorney, Agent, or Firm* — Wolf, Greenfield & Sacks, P.C.

(57) ABSTRACT

Provided herein are vaccine composition comprising a chemically-modified messenger ribonucleic acid (mRNA) encoding a hMPV fusion (F) glycoprotein and a chemically-modified mRNA encoding a hPIV3 F glycoprotein formulated in a cationic lipid nanoparticle formulation, and related method for inducing an antigen-specific immune response.

18 Claims, 7 Drawing Sheets

Figure 1:
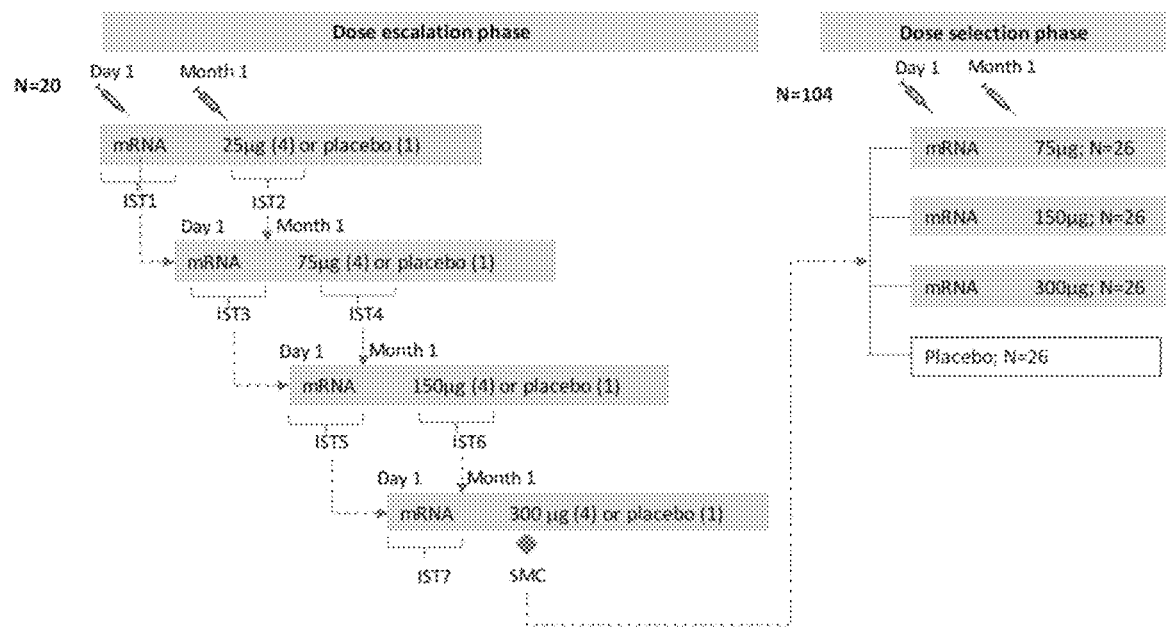

Specification includes a Sequence Listing.

(56) References Cited

U.S. PATENT DOCUMENTS

| | | | |
|---|---|---|---|
| 10,272,150 B2* | 4/2019 | Ciaramella | C07K 16/1027 |
| 10,273,269 B2 | 4/2019 | Ciaramella | |
| 10,449,244 B2 | 10/2019 | Ciaramella et al. | |
| 10,465,190 B1 | 11/2019 | Chen et al. | |
| 10,493,143 B2 | 12/2019 | Ciaramella et al. | |
| 10,526,629 B2 | 1/2020 | Rabideau et al. | |
| 2001/0001066 A1 | 5/2001 | Cezayirli et al. | |
| 2003/0032615 A1 | 2/2003 | Feigner et al. | |
| 2003/0092653 A1 | 5/2003 | Kisich et al. | |
| 2003/0232061 A1 | 12/2003 | Fouchier et al. | |
| 2004/0005545 A1 | 1/2004 | Fouchier et al. | |
| 2004/0096451 A1 | 5/2004 | Young et al. | |
| 2005/0032730 A1 | 2/2005 | Von Der Mulbe et al. | |
| 2005/0059624 A1 | 3/2005 | Hoerr et al. | |
| 2005/0250723 A1 | 11/2005 | Hoerr et al. | |
| 2006/0002958 A1 | 1/2006 | Naylor et al. | |
| 2006/0172003 A1 | 8/2006 | Meers et al. | |
| 2006/0172966 A1 | 8/2006 | Lipford et al. | |
| 2006/0228367 A1 | 10/2006 | Ulbrandt et al. | |
| 2007/0280929 A1 | 12/2007 | Hoerr et al. | |
| 2008/0025944 A1 | 1/2008 | Hoerr et al. | |
| 2008/0171711 A1 | 7/2008 | Hoerr et al. | |
| 2009/0123529 A1 | 5/2009 | Xiaomao | |
| 2009/0162395 A1 | 6/2009 | Crowe et al. | |
| 2010/0189729 A1 | 7/2010 | Hoerr et al. | |
| 2010/0203076 A1 | 8/2010 | Fotin-Mleczek et al. | |
| 2010/0239608 A1 | 9/2010 | Mulbe et al. | |
| 2010/0272747 A1 | 10/2010 | Chow et al. | |
| 2010/0291156 A1 | 11/2010 | Barner et al. | |
| 2010/0303851 A1 | 12/2010 | Hoerr et al. | |
| 2010/0305196 A1 | 12/2010 | Probst et al. | |
| 2011/0135645 A1 | 6/2011 | Williamson et al. | |
| 2011/0250225 A1 | 10/2011 | Fotin-Mleczek et al. | |
| 2011/0269950 A1 | 11/2011 | Mulbe et al. | |
| 2011/0311472 A1 | 12/2011 | Hoerr et al. | |
| 2012/0009221 A1 | 1/2012 | Hoerr et al. | |
| 2012/0045471 A1 | 2/2012 | Haller et al. | |
| 2012/0189700 A1 | 7/2012 | Aguilar et al. | |
| 2012/0219573 A1 | 8/2012 | Baumhof et al. | |
| 2012/0258046 A1 | 10/2012 | Mutske | |
| 2013/0022538 A1 | 1/2013 | Rossi | |
| 2013/0078281 A1 | 3/2013 | He et al. | |
| 2013/0102034 A1 | 4/2013 | Schrum et al. | |
| 2013/0121988 A1 | 5/2013 | Hoerr et al. | |
| 2013/0142818 A1 | 6/2013 | Baumhof et al. | |
| 2013/0171241 A1 | 7/2013 | Geall | |
| 2013/0183355 A1 | 7/2013 | Jain et al. | |
| 2013/0189351 A1 | 7/2013 | Geall | |
| 2013/0195867 A1 | 8/2013 | Hoerr et al. | |
| 2013/0195967 A1 | 8/2013 | Guild et al. | |
| 2013/0195968 A1 | 8/2013 | Geall et al. | |
| 2013/0195969 A1 | 8/2013 | Geall et al. | |
| 2013/0202684 A1 | 8/2013 | Geall et al. | |
| 2013/0236533 A1 | 9/2013 | Von Andrian et al. | |
| 2013/0243848 A1 | 9/2013 | Lobovkina et al. | |
| 2013/0245103 A1 | 9/2013 | de Fougerolles et al. | |
| 2013/0245107 A1 | 9/2013 | De Fougerolles et al. | |
| 2013/0259923 A1 | 10/2013 | Bancel et al. | |
| 2013/0266640 A1 | 10/2013 | De Fougerolles et al. | |
| 2013/0295043 A1 | 11/2013 | Kallen et al. | |
| 2013/0336998 A1 | 12/2013 | Kallen et al. | |
| 2014/0024076 A1 | 1/2014 | Tang et al. | |
| 2014/0037660 A1 | 2/2014 | Folin-Mleczek et al. | |
| 2014/0065228 A1 | 3/2014 | Yarowoski et al. | |
| 2014/0134201 A1 | 5/2014 | Tureci et al. | |
| 2014/0141042 A1 | 5/2014 | Vitelli et al. | |
| 2014/0147432 A1 | 5/2014 | Bancel et al. | |
| 2014/0148502 A1 | 5/2014 | Bancel et al. | |
| 2014/0193482 A1 | 7/2014 | Bancel et al. | |
| 2014/0206752 A1 | 7/2014 | Afeyan et al. | |
| 2014/0271829 A1 | 9/2014 | Lilja et al. | |
| 2014/0370497 A1 | 12/2014 | Fouchier et al. | |
| 2014/0378538 A1 | 12/2014 | Bancel | |
| 2015/0051268 A1 | 2/2015 | Bancel et al. | |
| 2015/0093413 A1 | 4/2015 | Thess et al. | |
| 2015/0126589 A1 | 5/2015 | Geiger et al. | |
| 2015/0141499 A1 | 5/2015 | Bancel et al. | |
| 2015/0307542 A1 | 10/2015 | Roy et al. | |
| 2015/0315541 A1 | 11/2015 | Bancel et al. | |
| 2015/0335728 A1 | 11/2015 | Wong et al. | |
| 2016/0024141 A1 | 1/2016 | Issa et al. | |
| 2016/0032273 A1 | 2/2016 | Shahrokh et al. | |
| 2016/0038612 A1 | 2/2016 | Hoge et al. | |
| 2016/0039884 A1 | 2/2016 | Li et al. | |
| 2016/0151474 A1 | 6/2016 | Kallen et al. | |
| 2016/0271272 A1 | 9/2016 | Bancel et al. | |
| 2016/0317647 A1 | 11/2016 | Ciaramella et al. | |
| 2016/0331828 A1 | 11/2016 | Ciaramella et al. | |
| 2017/0065675 A1 | 3/2017 | Bancel et al. | |
| 2017/0130255 A1 | 5/2017 | Wang et al. | |
| 2017/0202979 A1 | 7/2017 | Chakraborty et al. | |
| 2017/0340724 A1 | 11/2017 | Ciaramella et al. | |
| 2017/0340725 A1* | 11/2017 | Ciaramella | A61K 39/155 |
| 2018/0000953 A1 | 1/2018 | Almarsson et al. | |
| 2018/0002393 A1 | 1/2018 | Bancel et al. | |
| 2018/0008694 A1 | 1/2018 | Ciaramella et al. | |
| 2018/0028645 A1 | 2/2018 | Ciaramella et al. | |
| 2018/0028664 A1 | 2/2018 | Besin et al. | |
| 2018/0237849 A1 | 8/2018 | Thompson | |
| 2018/0243225 A1 | 8/2018 | Ciaramella | |
| 2018/0243230 A1 | 8/2018 | Smith | |
| 2018/0256628 A1 | 9/2018 | Hoge et al. | |
| 2018/0271970 A1 | 9/2018 | Ciaramella et al. | |
| 2018/0273977 A1 | 9/2018 | Mousavi et al. | |
| 2018/0274009 A1 | 9/2018 | Marquardt et al. | |
| 2018/0280496 A1 | 10/2018 | Ciaramella et al. | |
| 2018/0289792 A1 | 10/2018 | Ciaramella et al. | |
| 2018/0303929 A1 | 10/2018 | Ciaramella et al. | |
| 2018/0311336 A1 | 11/2018 | Ciaramella et al. | |
| 2018/0311343 A1 | 11/2018 | Huang et al. | |
| 2018/0318409 A1 | 11/2018 | Valiante et al. | |
| 2018/0363019 A1 | 12/2018 | Hoge | |
| 2018/0371047 A1 | 12/2018 | Ticho et al. | |
| 2019/0002890 A1 | 1/2019 | Martini et al. | |
| 2019/0008938 A1 | 1/2019 | Ciaramella et al. | |
| 2019/0085368 A1 | 3/2019 | Bancel et al. | |
| 2019/0099481 A1 | 4/2019 | Ciaramella et al. | |
| 2019/0175517 A1 | 6/2019 | Martini et al. | |
| 2019/0192646 A1 | 6/2019 | Cohen et al. | |
| 2019/0192653 A1 | 6/2019 | Hoge et al. | |
| 2019/0275170 A1 | 9/2019 | Benenato et al. | |
| 2019/0298658 A1 | 10/2019 | Benenato | |
| 2019/0314493 A1 | 10/2019 | Ciaramella et al. | |
| 2019/0336595 A1 | 11/2019 | Ciaramella | |
| 2019/0351040 A1 | 11/2019 | Valiante et al. | |
| 2020/0030432 A1 | 1/2020 | Ciaramella et al. | |
| 2020/0032274 A1 | 1/2020 | Mauger et al. | |
| 2020/0038499 A1 | 2/2020 | Narayanan et al. | |
| 2020/0054737 A1 | 2/2020 | Ciaramella et al. | |
| 2020/0069793 A1 | 3/2020 | Ciaramella | |
| 2020/0069794 A1 | 3/2020 | Ciaramella et al. | |
| 2020/0071689 A1 | 3/2020 | Miracco | |
| 2020/0109420 A1 | 4/2020 | Brito et al. | |

FOREIGN PATENT DOCUMENTS

| | | |
|---|---|---|
| EP | 1026253 | 8/2000 |
| EP | 1083232 | 2/2005 |
| EP | 1301614 B1 | 11/2006 |
| EP | 1383556 B1 | 10/2007 |
| EP | 1905844 A2 | 2/2008 |
| EP | 2188379 B1 | 1/2013 |
| EP | 2548960 A1 | 1/2013 |
| WO | WO 1987/005326 A1 | 9/1987 |
| WO | WO 1990/011092 A1 | 10/1990 |
| WO | WO 1993/014778 | 8/1993 |
| WO | WO 1995/024485 | 9/1995 |
| WO | WO 1995/026204 | 10/1995 |
| WO | WO 1995/033835 | 12/1995 |
| WO | WO 1998/058956 | 12/1998 |
| WO | WO 1999/033982 | 7/1999 |
| WO | WO 1999/052503 A2 | 10/1999 |
| WO | WO 2001/021810 A1 | 3/2001 |
| WO | WO 2003/072720 A2 | 9/2003 |

(56) References Cited

FOREIGN PATENT DOCUMENTS

| | | |
|---|---|---|
| WO | WO 2004/058166 A2 | 7/2004 |
| WO | WO 2004/076645 A1 | 9/2004 |
| WO | WO 2005/007689 A1 | 1/2005 |
| WO | WO 2005/009346 | 2/2005 |
| WO | WO 2005/027825 A2 | 3/2005 |
| WO | WO 2006/056027 A1 | 6/2006 |
| WO | WO 2006/071903 | 7/2006 |
| WO | WO 2006/095259 | 9/2006 |
| WO | WO 2007/038862 A1 | 4/2007 |
| WO | WO 2007/095976 A2 | 8/2007 |
| WO | WO 2008/014979 A3 | 2/2008 |
| WO | WO 2008/043052 | 4/2008 |
| WO | WO 2008/052770 A2 | 5/2008 |
| WO | WO 2008/083949 A2 | 7/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/115046 A2 | 10/2010 |
| WO | WO 2010/149743 A2 | 12/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/144358 A1 | 11/2011 |
| WO | WO 2012/006369 A2 | 1/2012 |
| WO | WO 2012/006378 A1 | 1/2012 |
| WO | WO 2012/006380 A2 | 1/2012 |
| WO | WO 2012/019630 A1 | 2/2012 |
| WO | WO 2012/019780 A1 | 2/2012 |
| WO | WO 2012/030901 A1 | 3/2012 |
| WO | WO 2012/075040 A2 | 6/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | WO 2013/052167 A2 | 4/2013 |
| WO | WO 2013/055905 A1 | 4/2013 |
| WO | WO 2013/056132 A2 | 4/2013 |
| WO | WO 2013/059496 A1 | 4/2013 |
| WO | WO 2013/090186 A1 | 6/2013 |
| WO | WO 2013/102203 A1 | 7/2013 |
| WO | WO 2013/113502 A1 | 8/2013 |
| WO | WO 2013/120628 A1 | 8/2013 |
| WO | WO 2013/120629 A1 | 8/2013 |
| WO | WO 2013/174409 A1 | 11/2013 |
| WO | WO 2013/185069 A1 | 12/2013 |
| WO | WO 2014/071963 A1 | 5/2014 |
| WO | WO 2014/072061 A1 | 5/2014 |
| WO | WO 2014/089486 A1 | 6/2014 |
| WO | WO 2014/127917 A1 | 8/2014 |
| WO | WO 2014/152027 A1 | 9/2014 |
| WO | WO 2014/152774 A1 | 9/2014 |
| WO | WO 2014/152940 A1 | 9/2014 |
| WO | WO 2014/160243 A1 | 10/2014 |
| WO | WO 2014/160463 A1 | 10/2014 |
| WO | WO 2015/013551 A1 | 1/2015 |
| WO | WO 2015/024667 A1 | 2/2015 |
| WO | WO 2015/024668 A2 | 2/2015 |
| WO | WO 2015/101414 A2 | 7/2015 |
| WO | WO 2015/101415 A1 | 7/2015 |
| WO | WO 2015/130584 A2 | 9/2015 |
| WO | WO 2015/164674 A1 | 10/2015 |
| WO | WO 2015/189425 A1 | 12/2015 |
| WO | WO 2015/199952 A1 | 12/2015 |
| WO | WO 2016/103238 | 6/2016 |
| WO | WO 2016/164762 A1 | 10/2016 |
| WO | WO 2016/176330 A1 | 11/2016 |
| WO | WO 2016/201377 A1 | 12/2016 |
| WO | WO 2016/203025 A1 | 12/2016 |
| WO | WO 2017/015457 A1 | 1/2017 |
| WO | WO 2017/015463 A1 | 1/2017 |
| WO | WO 2017/019935 A1 | 2/2017 |
| WO | WO 2017/020026 A1 | 2/2017 |
| WO | WO 2017/172890 A1 | 3/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070622 A1 | 4/2017 |
| WO | WO 2017/070623 A1 | 4/2017 |
| WO | WO 2017/070626 A2 | 4/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |
| WO | WO 2018/053209 A1 | 3/2018 |
| WO | WO 2018/075980 A1 | 4/2018 |
| WO | WO 2018/081459 A1 | 5/2018 |
| WO | WO 2018/081462 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |

OTHER PUBLICATIONS

U.S. Appl. No. 15/767,618, filed Apr. 11, 2018, Ciaramella et al.
U.S. Appl. No. 16/136,503, filed Sep. 20, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 16/582,621, filed Sep. 25, 2019, Chen et al.
U.S. Appl. No. 16/599,661, filed Oct. 11, 2019, Besin et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/839,278, filed Apr. 3, 2020, Hoge et al.
U.S. Appl. No. 16/389,545, filed Apr. 19, 2019, Ciaramella et al.
U.S. Appl. No. 16/368,270, filed Mar. 28, 2019, Ciaramella et al.
U.S. Appl. No. 16/805,587, filed Feb. 28, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.

(56) References Cited

OTHER PUBLICATIONS

U.S. Appl. No. 16/467,142, filed Jun. 6, 2019, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/131,793, filed Sep. 14, 2018, Ciaramella et al.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 16/608,451, filed Feb. 19, 2020, Mauger et al.
[No. Author Listed], "Messenger RNA", Internet: Wikipedia. Jun. 19, 2013, XP002699196, Retrieved from the Internet: URL: http://en.wikipedia.org/wiki/Messenger RNA.
Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.
Archer, S.J., Induction of a T-cell specific antigen on bone marrow lymphocytes with thymus RNA. Immunology. Jan. 1978;34(1):123-9.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.
Bettinger, T. et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bose, S. et al., Role of nucleolin in human parainfluenza virus type 3 infection of human lung epithelial cells. J Viral. Aug. 2004;78(15):8146-58.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Cheng et al., Multifunctional triblock copolymers for intracellular messenger RNA delivery. Biomaterials. Oct. 2012; 33(28): 6868-6876.
Conry, R.M. et al., Characterization of a messenger RNA polynucleotide vaccine vector. Cancer Res. Apr. 1, 1995 ;55 (7):1397-1400.
Cu et al., Enhanced Delivery and Potency of Self-Amplifying mRNA Vaccines by Electroporation in Situ, Vaccines, 2013, 1, 367-383. Abstract Only.
Dahlman, James E. et al., In vivo endothelial siRNA delivery using polymeric nanoparticles with low molecular weight, Nature Nanotechnology, 2014, No. vol.#, pp. 1-8.

Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012; 109(36): 14604-9. doi:10.1073/pnas,1209367109. Epub Aug. 20, 2012.
GenBank Accession No. ABM67072. Submitted to NCBI on Oct. 6, 2006. 1 page.
GenBank Accession No. AHX22069. First seen on NCBI on May 14, 2014. 2 pages.
GenBank Accession No. BAS30426.1 Submitted to NCBI on Sep. 2, 2015. 2 pages.
GenBank Accession No. EF051125. Submitted to NCBI on Oct. 7, 2006.
Gilboa, E. et al., Cancer immunotherapy with mRNA-transfected dendritic cells. Immunol Rev. Jun. 2004;199:251-63.
Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.
Hajj et al., Tools for translation: non-viral materials for therapeutic mRNA delivery. Nat Rev Mat. Sep. 2017;2:17056.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heiser, A. et al., Induction of polyclonal prostate cancer-specific CTL using dendritic cells transfected with amplified tumor RNA. J Immunol. Mar. 1, 2001; 166(5):2953-60.
Heyes et al., Cationic lipid saturation influences intracellular delivery of encapsulated nucleic acids. J Control Release. Oct. 3, 2005;107(2):276-87.
Hoerr, I. et al., In vivo application of RNA leads to induction of specific cytotoxic T lymphocytes and antibodies. EurJ Immunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp et al., Modification of antigen-encoding RNA increases stability, translational efficacy, and T-cell stimulatory capacity of dendritic cells. Blood. Dec. 15, 2006;108(13):4009-17.
Jirikowski, G.F., et al., Reversal of diabetes insipidus in Brattleboro Rats: Intrahypothalamic injection of vasopressin mRNA. Science. Feb. 1992; 255(5047): 996-998.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kalra et al., Virosomes: As a Drug Delivery Carrier. American Journal of Advanced Drug Delivery. 2013;1:29-35.

(56) References Cited

OTHER PUBLICATIONS

Kanapathipillai, et al., Nanoparticle targeting of anti-cancer drugs that alter intracellular signaling or influence the tumor microenvironment, Adv. Drug Deliv. Rev. (2014), , pp. 1-12.

Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.

Koztelski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.

Kreiter, S., et al., Intranodal vaccination with naked antigen-encoding RNA elicits potent prophylactic and therapeutic antitumoral immunity. Cancer Res. 2010; 70: 9031-9040.

Kreiter, S., et al., Tumor vaccination using messenger RNA: prospects of a future therapy. Curr Opinion in Immun. Jun. 2011; 23(3): 399-406.

Kuhn et al., mRNA as a versatile tool for exogenous protein expression. Current Gene Therapy. Oct. 2012; 12(5): 347-361.

Leitner et al., DNA and RNA-based vaccines: principles, progress and prospects. Vaccine. Dec. 10, 1999;18 (9-10):765-77.

Li, L. et al., Overcoming obstacles to develop effective and safe siRNA therapeutics. Expert Opin Biol Ther. May 2009; 9(5): 609-19.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi et al., Intranasal vaccination with messenger RNA as a new approach in gene therapy: Use against tuberculosis. BMC Biotechnol. Oct. 2010; 10(77): 1-11.

MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97bld2/MacLachlan_mRNA_Conf_2013.pdf. Last accessed Dec. 22, 2016.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 20165;11(8):e0161193. doi: 10.1371/journal.pone.0161193. eCollection 2016.

Martinon et al., Induction of virus-specific cytotoxic T lymphocytes in vivo by liposome-entrapped mRNA. EurJ Immunol. Jul. 1993;23(7):1719-22.

McKenzie et al., Nucleic acid vaccines: tasks and tactics. Immunol Res. 2001 ;24(3):225-44.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.

Mitchell, DA et al., RNA transfected dendritic cells as cancer vaccines. Curr Opin Mal Ther. Apr. 2000;2(2): 176-81.

Mitchell, DA et al., RNA-transfected dendritic cells in cancer immunotherapy. J Clin Invest. Nov. 2000;106 (9): 1065-9.

Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.

Muller, M.R. et al., Transfection of dendritic cells with RNA induces CD4- and COB-mediated T cell immunity against breast carcinomas and reveals the immunodominance of presented T cell epitopes. J Immunol. Jun. 15, 2003; 170 (12):5892-6.

Narayanan et al., Interplay between viruses and host mRNA degradation. Biochim Biophys Acta. Jun.-Jul. 2013;1829(6-7):732-41. doi: 10.1016/j.bbagrm.2012.12.003. Epub Dec. 26, 2012.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Phua et al., Messenger RNA (mRNA) nanoparticle tumour vaccination. Nanoscale. Jul. 21, 2014;6(14):7715-29. doi: 10.1039/c4nr01346h. Review.

Pollard et al., Type I IFN counteracts the induction of antigen-specific immune responses by lipid-based delivery of mRNA vaccines. Mol Ther. Jan. 2013; 21 (1): 251-259.

Pulford, B., et al., Liposome-siRNA-peptide complexes cross the blood-brain barrier and significantly decrease PrP'C on neuronal cells and PrP'RES in infected cell cultures. PLoS ONE. 2010; 5(6): e11085.

Rabinovich, P.M., et al., Synthetic messenger RNA as a tool for gene therapy. Hum. Gene Ther. Oct. 2006; 17: 1027-1035.

Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.

Sahin et al., mRNA-based therapeutics—developing a new class of drugs. Nat Rev Drug Discov. Oct. 2014;13(10):759-80. doi: 10.1038/nrd4278. Epub Sep. 19, 2014.

Schirrmacher et al., Intra-pinna anti-tumor vaccination with self-replicating infectious RNA or with DNA encoding a model tumor antigen and a cytokine. Gene Ther. Jul. 2000;7(13): 1137-47.

Schmitt, W.E. et al., In vitro induction of a bladder cancer-specific T-cell response by mRNA-transfected dendritic cells. J Cancer Res Clin Oncol. 2001 ;127(3):203-6.

Schott et al., Viral and non-viral approaches for transient delivery of mRNA and proteins. Current Gene Ther. 2011; 11 (5): 382-398.

Segura, J., et al., Monitoring gene therapy by external imaging of mRNA: Pilot study on murine erythropoietin. Ther Drug Monit. Oct. 2007; 29(5): 612-8.

Smits, E., et al., RNA-based gene transfer for adult stem cells and T cells. Leukemia. 2004; 18: 1898-1902.

Sohn, R.L., et al., In-vivo particle mediated delivery of mRNA to mammalian tissues: ballistic and biological effects. Wound Rep and Regen. Jul.-Aug. 2001; 287-296.

Strong, V.T. et al., Incorporation of beta-globin untranslated regions into a Sindbis virus vector for augmentation of heterologous mRNA expression. Gene Ther. Jun. 1997;4(6):624-7.

Sullenger, BA et al., Emerging clinical applications of RNA. Nature. Jul. 11, 2002;418(6894):252-8.

Tang et al., A host-range restricted parainfluenza virus type 3 (PIV3) expressing the human metapneumovirus (hMPV) fusion protein elicits protective immunity in African green monkeys. Vaccine. Feb. 25, 2005;23(14): 1657-67.

(56) References Cited

OTHER PUBLICATIONS

Tavernier, G., et al., mRNA as gene therapeutic: How to control protein expression. J. of Controlled Release. Mar. 2011; 150(3): 238-247.

Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.

Vassilev et al., Microparticle-mediated RNA immunization against bovine viral diarrhea virus. Vaccine. Feb. 28, 2001;19(15-16):2012-9.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Wong et al., An mRNA vaccine for influenza. Nat Biotechnol. Dec. 2012;30(12):1202-4. doi: 10.1038/nbt.2439.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Ying et al., Cancer therapy using a self-replicating RNA vaccine. Nat Med. Jul. 1999;5(7):823-7.

Zhou, W.Z. et al., RNA melanoma vaccine: induction of antitumor immunity by human glycoprotein 100 mRNA immunization. Hum Gene Ther. Nov. 1, 1999;10(16):2719-24.

\* cited by examiner hMPV-A hMPV-B

PIV3

“common colds” occur each year. Respiratory conditions are among the most frequent reasons for hospital stays among children.

```
                       SEQUENCE LISTING

<160> NUMBER OF SEQ ID NOS: 19

<210> SEQ ID NO 1
<211> LENGTH: 1786
<212> TYPE: RNA
<213> ORGANISM: Artificial Sequence
<220> FEATURE:
<223> OTHER INFORMATION: Synthetic Polynucleotide

<400> SEQUENCE: 1
gggaaauaag agagaaaaga agaguaagaa gaaauauaag agccaccaug agcuggaagg      60
uggugauuau cuucagccug cugauuacac cucaacacgg ccugaaggag agcuaccugg     120
aagagagcug cuccaccauc accgagggcu accugagcgu gcugcggacc ggcugguaca     180
ccaacguguu cacccuggag gugggcgacg uggagaaccu gaccugcagc gacggcccua     240
gccugaucaa gaccgagcug gaccugacca agagcgcucu gagagagcug aagaccgugu     300
ccgccgacca gcuggccaga gaggaacaga ucgagaaccc ucggcagagc agauucgugc     360
ugggcgccau cgcucuggga gucgccgcug ccgcugcagu gacagcugga guggccauug     420
cuaagaccau cagacuggaa agcgagguga cagccaucaa caaugcccug aagaagacca     480
acgaggccgu gagcacccug ggcaauggag ugagagugcu ggccacagcc gugcgggagc     540
ugaaggacuu cgugagcaag aaccugacca gagccaucaa caagaacaag ugcgacaucg     600
augaccugaa gauggccgug agcuucuccc aguucaacag acgguccug aacguggga     660 gacaguucuc cgacaacgcu ggaaucacac cugccauuag ccuggaccug augaccgacg     720
ccgagcuggc uagagccgug cccaacaugc ccaccagcgc uggccagauc aagcugaugc     780
uggagaacag agccauggug cggagaaagg gcuucggcau ccugauuggg guguauggaa     840
gcuccgugau cuacauggug cagcugccca ucuucgcgcu gaucgacaca cccugcugga     900
ucgugaaggc cgcuccuagc ugcuccgaga agaaaggaaa cuaugccugu cugcugagag     960
aggaccaggg cugguacugc cagaacgccg gaagcacagu guacauaccc aacgagaagg    1020
acugcgagac cagaggcgac cacguguucu gcgacaccgc ugccggaauc aacguggccg    1080
agcagagcaa ggagugcaac aucaacauca gcacaaccaa cuaccccugc aaggugagca    1140
ccggacggca ccccaucagc auggugggcuc ugagcccucu gggcgcucug guggccugcu    1200
auaagggcgu guccuguagc aucggcagca aucgggugg caucaucaag cagcugaaca    1260
agggaugcuc cuacaucacc aaccaggacg ccgacaccgu gaccaucgac aacaccgugu    1320
```

```
accagcugag caagguggag ggcgagcagc acgugaucaa gggcagaccc gugagcucca    1380
gcuucgaccc caucaaguuc ccugaggacc aguucaacgu ggcccuggac cagguguuug    1440
agaacaucga gaacagccag gcccuggugg accagagcaa cagaauccug uccagcgcug    1500
agaagggcaa caccggcuuc aucauguga cauucugau cgccgugcug ggcagcucca    1560
ugauccuggu gagcaucuuc aucauuauca agaagaccaa gaaacccacc ggagcccuc    1620 cugagcugag cggcgugacc aacaauggcu cauucccca caacugauga uaauaggcug    1680
gagccucggu ggccaugcuu cuugcccuu gggccucccc ccagcccuc ucccccuucc    1740 ugcacccgua cccccguggu cuuugaauaa agucugagug ggcggc    1786
```

<210> SEQ ID NO 2
<211> LENGTH: 1783
<212> TYPE: RNA
<213> ORGANISM: Artificial Sequence
<220> FEATURE:
<223> OTHER INFORMATION: Synthetic Polynucleotide

<400> SEQUENCE: 2

```
gggaauaag agagaaaaga agaguaagaa gaaauauaag agccaccaug cccaucagca      60
uccugcugau caucaccaca augaucaugg ccagccacug ccagaucgac aucaccaagc     120
ugcagcacgu gggcgugcuc gugaacagcc caagggcau gaagaucagc cagaacuucg     180
agacacgcua ccugauccug agccugaucc ccaagaucga ggacagcaac agcugcggcg     240
accagcagau caagcaguac aagcggcugc uggacagacu gauucauccc cuguacgacg     300
gccugcggcu gcagaaagac gugaucguga ccaaccagga agcaacgag acaccgaccc     360 cccggaccga gagauucuuc ggcggcguga ucggcacaau cgcccuggga guggccacaa     420
gcgcccagau uacagccgcu guggcccugg uggaagccaa gcaggccaga agcgacaucg     480
agaagcugaa agaggccauc cggacaccca acaaggccgu gcagagcgug caguccagcg     540
ugggcaaucu gaucgugggc cucaaguccg ugcaggacua cgugaacaaa gaaaucgugc     600
ccucuaucgc ccggcugggc ugugaagcug ccggacugca gcugggcauu gcccugacac     660
agcacuacag cgagcugacc aacauccuuc gcgacaacau cggcagccug caggaaaagg     720
gcauuaagcu gcagggaauc gccagccugu accgcaccaa caucaccgag aucuucacca     780
ccagcaccgu ggauaaguac gacaucuacg accugcuguu caccgagagc ucaaagugc     840 gcgugaucga cguggaccug aacgacuaca gcaucacccu gcaagugcgg cugcccucgc     900
ugaccagacu gcugaacacc cagaucuaca agguggacag caucuccuac aacauccaga     960
accgcgagug guacauccu cugcccagcc acauuaugac caagggcgcc uuucugggcg    1020
gagccgacgu gaaagagugc aucgaggccu ucagcagcua caucgccccc agcgacccug    1080
gcuucgugcu gaaccacgag auggaaagcu gccugagcgg caacaucagc cagugcccca    1140
gaaccaccgu gaccuccgac aucgugccca gauacgccuu cgugaaugg ggcgugguag    1200 ccaacugcau caccaccacc uguaccugca acggcaucgg caaccggauc aaccagccuc    1260
ccgaucaggg cgugaagauu aucacccaca agagguaa caccaucggc aucaacggca    1320
ugcuguucaa uaccaacaaa gagggcaccc uggccuucua cacccccgac gauaucaccc    1380
ugaacaacuc cguggcucug gaccccaucg acaucccau cgagcugaac aaggccaaga    1440
gcgaccugga agauccaaa gaguggauc ggcggagcaa ccagaagcug gacucuaucg    1500
gcagcuggca ccagagcagc accaccauca ucgugacccu gauuaugaug auuaccgu    1560 ucauccucaa cauuaccauc aucacuaucg ccauuaagua cuaccggauc cagaaacgga    1620
```

-continued

```
accggguuga ccagaaugac aagcccuacg ugcugacaaa caagugauaa uaggcuggag    1680 ccucggguggc caugcuucuu gccccuuggg ccuccccca gccccuccuc cccuuccugc    1740
acccguaccc ccgugguucuu ugaauaaagu cugaguggg ggc                      1783

<210> SEQ ID NO 3
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 3
gggaaauaag agagaaaaga agaguaagaa gaaauauaag agccacc                   47

<210> SEQ ID NO 4
<211> LENGTH: 57
<212> TYPE: RNA
<213> ORGANISM: Artificial Sequence
<220> FEATURE:
<223> OTHER INFORMATION: Synthetic Polynucleotide

<400> SEQUENCE: 4
gggaaauaag agagaaaaga agaguaagaa gaaauauaag accccggcgc cgccacc        57

<210> SEQ ID NO 5
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 5
cggcgggugu gucugaaaua aguuucuggu gccccauugc ccacguccuu ccccuccucc    60 ccgaccccc uccggguucc ccguucuucg uaccggguggc uccgaggucg gauaauagu    119

<210> SEQ ID NO 6
<211> LENGTH: 119
<212> TYPE: RNA
<213> ORGANISM: Artificial Sequence
<220> FEATURE:
<223> OTHER INFORMATION: Synthetic Polynulceotide

<400> SEQUENCE: 6
cggcgggugu gucugaaaua aguuucuggu gccccauugc ccacguccuu ccccuccucc    60 ccgaccccc uccggguucc ccguucuucg auccggguggc uccgaggucg gauaauagu    119

<210> SEQ ID NO 7
<211> LENGTH: 1620
<212> TYPE: RNA
<213> ORGANISM: Artificial Sequence
<220> FEATURE:
<223> OTHER INFORMATION: Synthetic Polynucleotide

<400> SEQUENCE: 7
augagcugga aggugugau uaucuucagc cugcugauua caccucaaca cggccugaag     60
gagagcuacc uggaagagag cugcuccacc aucaccgagg cuaccugag cgucugcgg     120 accggcuggu acaccaacgu guucacccug gagguggcg acguggagaa ccugaccugc    180
agcgacggcc cuagccugau caagaccgag cuggaccuga ccaagagcgc ucugagagag    240
cugaagaccg ugucccgccga ccagcuggcc agagaggaac agaucgagaa cccucggcag    300
```

```
agcagauucg ugcugggcgc caucgcucug ggagucgccg cugccgcugc agugacagcu    360
ggaguggcca uugcuaagac caucagacug gaaagcgagg ugacagccau caacaaugcc    420
cugaagaaga ccaacgaggc cgugagcacc cugggcaaug gagugagagu gcuggccaca    480
gccgugcggg agcugaagga cuucgugagc aagaaccuga ccagagccau caacaagaac    540
aagugcgaca ucgaugaccu gaagauggcc gugagcuucu cccaguucaa cagacgguuc    600
cugaacgugg ugagacaguu cuccgacaac gcuggaauca caccugccau uagccuggac    660
cugaugaccg acgccgagcu ggcuagagcc gugcccaaca ugcccaccag cgcuggccag    720
aucaagcuga ugcuggagaa cagagccaug gugcggagaa agggcuucgg cauccugauu    780
ggggugauau gaagcuccgu gaucuacaug gugcagcugc ccaucuucgg cgugaucgac    840
acaccugcu ggaucgugaa ggccgcuccu agcugcuccg agaagaaagg aaacuaugcc    900
ugucugcuga gagaggacca gggcugguac ugccagaacg ccggaagcac agucuacuau    960
cccaacgaga aggacugcga gaccagaggc gaccacugu ucugcgacac cgcugccgga   1020
aucaacgugg ccgagcagag caaggagugc aacaucaaca ucagcacaac caacuacccc   1080
ugcaagguga gcaccggacg gcaccccauc agcaugguug cucugagccc ucugggcgcu   1140
cugguggccu gcuauaaggg cgugccugu agcaucggca gcaaucgggu gggcaucauc   1200
aagcagcuga acaagggaug cuccuacauc accaaccagg acgccgacac cgugaccauc   1260
gacaacaccg uguaccagcu gagcaaggug gagggcgagc agcacgugau caagggcaga   1320
cccgugagcu ccagcuucga ccccaucaag uucccugagg accaguucaa cgguggcccug   1380
gaccaggugu uugagaacau cgagaacagc caggcccugg uggaccagag caacagaauc   1440
cuguccagcg cugagaaggg caacaccggc uucaucauug ugaucauucu gaucgccgug   1500
cugggcagcu ccaugaaccu ggugagcauc uucaucauua caagaagac caagaaacccc   1560
accggagccc cuccugagcu gagcggcgug accaacaaug gcuucauucc ccacaacuga   1620
```

<210> SEQ ID NO 8
<211> LENGTH: 541
<212> TYPE: PRT
<213> ORGANISM: Artificial Sequence
<220> FEATURE:
<223> OTHER INFORMATION: Synthetic Polypeptide

<400> SEQUENCE: 8

```
Met Ser Trp Lys Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
```

```
                130             135             140
Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Glu Thr Val Arg Arg Lys
                245                 250                 255

Gly Phe Gly Ile Leu Ile Gly Val Tyr Gly Ser Ser Val Ile Tyr Met
            260                 265                 270

Val Gln Leu Pro Ile Phe Gly Val Ile Asp Thr Pro Cys Trp Ile Val
        275                 280                 285

Lys Ala Ala Pro Ser Cys Ser Glu Lys Lys Gly Asn Tyr Ala Cys Leu
290                 295                 300

Leu Arg Glu Asp Gln Gly Trp Tyr Cys Gln Asn Ala Gly Ser Thr Val
305                 310                 315                 320

Tyr Tyr Pro Asn Glu Lys Asp Cys Glu Thr Arg Gly Asp His Val Phe
                325                 330                 335

Cys Asp Thr Ala Ala Gly Ile Asn Val Ala Glu Gln Ser Lys Glu Cys
            340                 345                 350

Asn Ile Asn Ile Ser Thr Thr Asn Tyr Pro Cys Lys Val Ser Thr Gly
        355                 360                 365

Arg His Pro Ile Ser Met Val Ala Leu Ser Pro Leu Gly Ala Leu Val
370                 375                 380

Ala Cys Tyr Lys Gly Val Ser Cys Ser Ile Gly Ser Asn Arg Val Gly
385                 390                 395                 400

Ile Ile Lys Gln Leu Asn Lys Gly Cys Ser Tyr Ile Thr Asn Gln Asp
                405                 410                 415

Ala Asp Thr Val Thr Ile Asp Asn Thr Val Tyr Gln Leu Ser Lys Val
            420                 425                 430

Glu Gly Glu Gln His Val Ile Lys Gly Arg Pro Val Ser Ser Ser Phe
        435                 440                 445

Asp Pro Ile Lys Phe Pro Glu Asp Gln Phe Asn Val Ala Leu Asp Gln
450                 455                 460

Val Phe Glu Asn Ile Glu Asn Ser Gln Ala Leu Val Asp Gln Ser Asn
465                 470                 475                 480

Arg Ile Leu Ser Ser Ala Glu Lys Gly Asn Thr Gly Phe Ile Ile Val
                485                 490                 495

Ile Ile Leu Ile Ala Val Leu Gly Ser Ser Met Ile Leu Val Ser Ile
            500                 505                 510

Phe Ile Ile Ile Lys Lys Thr Lys Lys Pro Thr Gly Ala Pro Pro Glu
        515                 520                 525

Leu Ser Gly Val Thr Asn Asn Gly Phe Ile Pro His Asn
530                 535                 540

<210> SEQ ID NO 9
```

<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| augcccauca | gcauccugcu | gaucaucacc | acaaugauca | uggccagcca | cugccagauc | 60 |
| gacaucacca | agcugcagca | cgugggcgug | cucgugaaca | gccccaaggg | caugaagauc | 120 |
| agccagaacu | ucgagacacg | cuaccugauc | cugagccuga | uccccaagau | cgaggacagc | 180 |
| aacagcugcg | gcgaccagca | gaucaagcag | uacaagcggc | ugcuggacag | acugaucauc | 240 |
| ccccuguacg | acggccugcg | gcugcagaaa | gacgugaucu | ugaccaacca | ggaaagcaac | 300 |
| gagaacaccg | accccccggac | cgagagauuc | uucggcggcg | ugaucggcac | aaucgcccug | 360 |
| ggaguggcca | agcgcccca | gauuacagcc | gcugguggcc | ugguggaagc | caagcaggcc | 420 |
| agaagcgaca | ucgagaagcu | gaaagaggcc | auccgggaca | ccaacaaggc | cgugcagagc | 480 |
| gugcagucca | gcgugggcaa | ucugaucgug | gccaucaagu | ccgugcagga | cuacgugaac | 540 |
| aaagaaaucg | ugcccucuau | cgcccggcug | gcugugaag | cugccggacu | gcagcugggc | 600 |
| auugcccuga | cacagcacua | cagcgagcug | accaacaucu | ucggcgacaa | caucggcagc | 660 |
| cugcaggaaa | agggcauuaa | gcugcaggga | aucgccagcc | uguaccgcac | caacaucacc | 720 |
| gagaucuuca | ccaccagcac | cguggauaag | uacgacaucu | cgaccugcu | guucaccgag | 780 |
| agcaucaaag | ugcgcgugau | cgacguggac | cugaacgacu | acagcaucac | ccugcaagug | 840 |
| cggcugcccc | ugcugaccag | acugcugaac | acccagaucu | caaggugga | cagcaucucc | 900 |
| uacaacaucc | agaaccgcga | gugguacauc | ccucugccca | gccacauuau | gaccaagggc | 960 |
| gccuuucugg | cgcagagccga | cgugaaagag | ugcaucgagg | ccuucagcag | cuacaucugc | 1020 |
| cccagcgacc | cuggcuucgu | gcugaaccac | gagauggaaa | gcugccugag | cggcaacauc | 1080 |
| agccagugcc | ccagaaccac | cgugaccucc | gacaucgugc | ccagauacgc | cuucgugaau | 1140 |
| ggcggcgugg | uggccaacug | caucaccacc | accuguaccu | gcaacggcau | cggcaaccgg | 1200 |
| aucaaccagc | cucccgauca | gggcgugaag | auuauccccc | acaaagagug | uaacaccauc | 1260 |
| ggcaucaacg | gcaugcuguu | caauaccaac | aaagagggca | cccuggccuu | cuacaccccc | 1320 |
| gacgauauca | cccugaacaa | uccguggcu | cuggacccca | ucgacaucuc | caucgagcug | 1380 |
| aacaaggcca | agagcgaccu | ggaagagucc | aagaguggga | uccggcggag | caaccagaag | 1440 |
| cuggacucua | ucggcagcug | gcaccagagc | agcaccacca | ucaucgugau | ccugauuaug | 1500 |
| augauuaucc | uguucaucau | caacauuacc | aucaucacua | ucgccauuaa | guacuaccgg | 1560 |
| auccagaaac | ggaaccgggu | ggaccagaau | gacaagcccu | acgugcugac | aaacaag | 1617 |

<210> SEQ ID NO 10
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 10

Met Pro Ile Ser Ile Leu Leu Ile Ile Thr Thr Met Ile Met Ala Ser
1               5                   10                  15

His Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr

```
              35                  40                  45
Leu Ile Leu Ser Leu Ile Pro Lys Ile Glu Asp Ser Asn Ser Cys Gly
 50                  55                  60

Asp Gln Gln Ile Lys Gln Tyr Lys Arg Leu Leu Asp Arg Leu Ile Ile
 65                  70                  75                  80

Pro Leu Tyr Asp Gly Leu Arg Leu Gln Lys Asp Val Ile Val Thr Asn
                 85                  90                  95

Gln Glu Ser Asn Glu Asn Thr Asp Pro Arg Thr Glu Arg Phe Phe Gly
                100                 105                 110

Gly Val Ile Gly Thr Ile Ala Leu Gly Val Ala Thr Ser Ala Gln Ile
                115                 120                 125

Thr Ala Ala Val Ala Leu Val Glu Ala Lys Gln Ala Arg Ser Asp Ile
130                 135                 140

Glu Lys Leu Lys Glu Ala Ile Arg Asp Thr Asn Lys Ala Val Gln Ser
145                 150                 155                 160

Val Gln Ser Ser Val Gly Asn Leu Ile Val Ala Ile Lys Ser Val Gln
                165                 170                 175

Asp Tyr Val Asn Lys Glu Ile Val Pro Ser Ile Ala Arg Leu Gly Cys
                180                 185                 190

Glu Ala Ala Gly Leu Gln Leu Gly Ile Ala Leu Thr Gln His Tyr Ser
                195                 200                 205

Glu Leu Thr Asn Ile Phe Gly Asp Asn Ile Gly Ser Leu Gln Glu Lys
210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
                260                 265                 270

Asp Tyr Ser Ile Thr Leu Gln Val Arg Leu Pro Leu Leu Thr Arg Leu
                275                 280                 285

Leu Asn Thr Gln Ile Tyr Lys Val Asp Ser Ile Ser Tyr Asn Ile Gln
290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
                340                 345                 350

Glu Ser Cys Leu Ser Gly Asn Ile Ser Gln Cys Pro Arg Thr Thr Val
                355                 360                 365

Thr Ser Asp Ile Val Pro Arg Tyr Ala Phe Val Asn Gly Gly Val Val
370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
                420                 425                 430

Gly Thr Leu Ala Phe Tyr Thr Pro Asp Asp Ile Thr Leu Asn Asn Ser
                435                 440                 445

Val Ala Leu Asp Pro Ile Asp Ile Ser Ile Glu Leu Asn Lys Ala Lys
450                 455                 460
```

```
Ser Asp Leu Glu Glu Ser Lys Glu Trp Ile Arg Arg Ser Asn Gln Lys
465                 470                 475                 480

Leu Asp Ser Ile Gly Ser Trp His Gln Ser Ser Thr Thr Ile Ile Val
            485                 490                 495

Ile Leu Ile Met Met Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535

<210> SEQ ID NO 11
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 11

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Gly
            20                  25                  30

<210> SEQ ID NO 12
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 12

Met Asp Trp Thr Trp Ile Leu Phe Leu Val Ala Ala Thr Arg Val
1               5                   10                  15

His Ser

<210> SEQ ID NO 13
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 13

Met Glu Thr Pro Ala Gln Leu Leu Phe Leu Leu Leu Leu Trp Leu Pro
1               5                   10                  15

Asp Thr Thr Gly
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 14

Met Leu Gly Ser Asn Ser Gly Gln Arg Val Val Phe Thr Ile Leu Leu
1               5                   10                  15

Leu Leu Val Ala Pro Ala Tyr Ser
            20
```

```
<210> SEQ ID NO 15
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 15

Met Lys Cys Leu Leu Tyr Leu Ala Phe Leu Phe Ile Gly Val Asn Cys
1               5                   10                  15

Ala

<210> SEQ ID NO 16
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 16

Met Trp Leu Val Ser Leu Ala Ile Val Thr Ala Cys Ala Gly Ala
1               5                   10                  15

<210> SEQ ID NO 17
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(3)
<223> OTHER INFORMATION: Where N may be Adenine or Guanine

<400> SEQUENCE: 17 ccnccaugg                                                                9

<210> SEQ ID NO 18
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 18
gggauccuac c                                                            11

<210> SEQ ID NO 19
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(9)
<223> OTHER INFORMATION: Where n may be Adenine or Uracil

<400> SEQUENCE: 19 uuauuuann                                                                9
```

HMPV/HPIV3 MRNA VACCINE COMPOSITION

RELATED APPLICATIONS

This application claims the benefit under 35 U.S.C. § 119(e) of U.S. provisional application 62/804,482, filed Feb. 12, 2019, U.S. provisional application 62/811,381, filed Feb. 27, 2019, and U.S. provisional application 62/877,937, filed Jul. 24, 2019, each of which is herein incorporated by reference in its entirety.

BACKGROUND

Respiratory disease is a medical term that encompasses pathological conditions affecting the organs and tissues that make gas exchange possible in higher organisms, and includes conditions of the upper respiratory tract, trachea, bronchi, bronchioles, alveoli, pleura and pleural cavity, and the nerves and muscles of breathing. Respiratory diseases range from mild and self-limiting, such as the common cold, to life-threatening entities like bacterial pneumonia, pulmonary embolism, acute asthma and lung cancer. Respiratory disease is a common and significant cause of illness and death around the world. In the US, approximately 1 billion "common colds" occur each year. Respiratory conditions are among the most frequent reasons for hospital stays among children.

Despite decades of research, no vaccines currently exist (Sato and Wright, *Pediatr. Infect. Dis. J.* 2008; 27(10 Suppl): S123-5) for respiratory virus, such as human metapneumovirus (hMPV) and human parainfluenza virus type 3 (hPIV3). The continuing health problems associated with hMPV and hPIV3 are of concern internationally, reinforcing the importance of developing effective and safe vaccine candidates against these viruses.

SUMMARY

Provided herein is a messenger ribonucleic acid (mRNA)-based prophylactic vaccine comprising a mRNA encoding the full length hMPV F glycoprotein and a mRNA encoding the full length hPIV3 F glycoprotein, which has been shown to be safe and effective for inducing a neutralizing antibody response specific for hMPV F glycoprotein and hPIV3 F glycoprotein. The vaccine should prevent upper and lower respiratory illnesses associated with hMPV and/or hPIV3 infection, particularly among young children and older adults. A principal immunological goal is to boost functional antibody responses (serum neutralizing antibodies) along with cellular immune responses against these respiratory viruses. The mRNA vaccines provided herein include, in some embodiments, chemically modified mRNAs formulated within ionizable cationic lipid (e.g., Compound I)-containing lipid nanoparticles (LNPs). The mRNA vaccine is, in some embodiments, intramuscularly administered in single dose annually prior to, or during, the cold season. To date, no effective vaccine to prevent hMPV or hPIV3 has been licensed, and treatment is limited to supportive therapy.

Thus, some aspects of the present disclosure provide a method for producing an antigen-specific immune response to human metapneumovirus (hMPV) and human parainfluenza virus (hPIV3) in a subject comprising administering to a human subject a safe and effective dose of a vaccine composition comprising a chemically-modified messenger ribonucleic acid (mRNA) encoding a hMPV fusion (F) glycoprotein and a chemically-modified mRNA encoding a hPIV3 F glycoprotein formulated in a lipid nanoparticle comprising an ionizable cationic lipid, cholesterol, DSPC (1,2-Distearoyl-sn-glycero-3-phosphocholine), and optionally DMG-PEG (1,2-dimyristoyl-rac-glycero-3-methoxypolyethylene glycol-2000), thereby inducing an antigen-specific immune response to hMPV and hPIV3 in the subject.

In some aspects, the methods comprise administering to a human subject a 25 µg to 100 µg dose of a vaccine composition comprising (a) a chemically-modified messenger ribonucleic acid (mRNA) that encodes a hMPV fusion (F) glycoprotein and comprises an open reading frame that comprises a nucleotide sequence having at least 95% identity to the nucleotide sequence of SEQ ID NO: 7, and (b) a chemically-modified mRNA that encodes a hPIV3 F glycoprotein and comprises an open reading frame that comprises a nucleotide sequence having at least 95% identity to the nucleotide sequence of SEQ ID NO: 9, formulated in a lipid nanoparticle comprising 45-55 mole percent ionizable cationic lipid, 5-15 mole percent DSPC, 35-40 mole percent cholesterol, and optionally 1-2 mole percent DMG-PEG, thereby inducing an antigen-specific immune response to hMPV and hPIV3 in the subject.

In other aspects, the methods comprise administering to a human subject a 25 µg to 100 µg dose of a vaccine composition comprising (a) a chemically-modified messenger ribonucleic acid (mRNA) that encodes a hMPV fusion (F) glycoprotein and comprises an open reading frame that comprises the nucleotide sequence of SEQ ID NO: 7, and (b) a chemically-modified mRNA that encodes a hPIV3 F glycoprotein and comprises an open reading frame that comprises the nucleotide sequence of SEQ ID NO: 9, formulated in formulated in an ionizable cationic lipid nanoparticle, thereby inducing an antigen-specific immune response to hMPV and hPIV3 in the subject, wherein the antigen-specific immune response is measured as a geometric mean ratio (GMR) of serum neutralizing antibody titers to hMPV and hPIV3, the GMR for hMPV is in the range of 6 to 6.5, and the GMR for hPIV3 is in the range of 3 to 3.5.

In some embodiments, the open reading frame of (a) comprises the nucleotide sequence of SEQ ID NO: 7. In some embodiments, the mRNA of (a) comprises the nucleotide sequence of SEQ ID NO: 1. In some embodiments, the open reading frame of (b) comprises the nucleotide sequence of SEQ ID NO: 9. In some embodiments, the mRNA of (b) comprises the nucleotide sequence of SEQ ID NO: 2.

In some embodiments, the composition is administered at a dose of 25 µg to 300 µg, at a dose of 25 µg to 150 µg, at a dose of 25 µg to 100 µg, at a dose of 25 µg to 75 µg, or at a dose of 25 µg to 50 µg. In some embodiments, the composition is administered at a dose of 25 µg. In some embodiments, the composition is administered at a dose of 30 µg. In some embodiments, the composition is administered at a dose of 75 µg. In some embodiments, the composition is administered at a dose of 150 µg.

In some embodiments, the subject is an adult subject.

In some embodiments, the subject is a pediatric subject and the composition is administered at a dose of 10 µg to 150 µg, at a dose of 10 µg to 100 µg, at a dose of 10 µg to 50 µg, or at a dose of 10 µg to 30 µg. In some embodiments, the composition is administered at a dose of 10 µg. In some embodiments, the composition is administered at a dose of 30 µg. In some embodiments, the composition is administered at a dose of 100 µg.

In some embodiments, administration of the vaccine composition elicits serum neutralizing antibody titers against hMPV, including hMPV-A and hMPV-B, and hPIV3.

In some embodiments, administration of a single 10 μg, 25 μg, 30 μg, 75 μg, 100 μg, 150 μg, or 300 μg dose of the vaccine composition elicits serum neutralizing antibody titers against hMPV and hPIV3 with no apparent dose response.

In some embodiments, the antigen-specific immune response is measured as a geometric mean ratio (GMR) of serum neutralizing antibody titers to hMPV and hPIV3, and the GMR of 28 days to baseline titers for hMPV in subjects administered a ≥75 μg dose of the vaccine composition is in the range of 4 to 8, optionally 4.87-7.73. In some embodiments, the GMR for hMPV-A is 6.04. In some embodiments, the GMR for hMPV-B is 6.33.

In some embodiments, the antigen-specific immune response is measured as a geometric mean ratio (GMR) of serum neutralizing antibody titers to hMPV and hPIV3, and the GMR of 28 days to baseline titers for hPIV3 in subjects administered a ≥75 μg dose of the vaccine composition is in the range of 3 to 4, optionally 3.13-3.36. In some embodiments, the GMR for hPIV3 is 3.24.

In some embodiments, the antigen-specific immune response is measured as a geometric mean titer (GMT) of serum neutralizing antibodies to hMPV, and wherein the GMT in serum neutralizing antibodies to hMPV increases in the subject at least 2 fold within 30 days relative to baseline. In some embodiments, the antigen-specific immune response is measured as a geometric mean titer (GMT) of serum neutralizing antibodies to hMPV, and wherein the GMT in serum neutralizing antibodies to hMPV increases in the subject at least 2 fold within 30 days relative to baseline, following a single 25 μg dose or a single 75 μg dose of the vaccine composition. In some embodiments, the antigen-specific immune response is measured as a geometric mean titer (GMT) of serum neutralizing antibodies to hMPV, and wherein the GMT in serum neutralizing antibodies to hMPV increases in the subject at least 6 fold within 30 days relative to baseline. In some embodiments, the antigen-specific immune response is measured as a GMT of serum neutralizing antibodies to hMPV, and wherein the GMT in serum neutralizing antibodies to hMPV increases in the subject at least 6 fold within 30 days relative to baseline, following a single 25 μg dose or a single 75 μg dose of the vaccine composition.

In some embodiments, the antigen-specific immune response is measured as a GMT of serum neutralizing antibodies to hPIV3, and wherein the GMT in serum neutralizing antibodies to hPIV3 increases in the subject at least 2 fold within 30 days relative to baseline. In some embodiments, the antigen-specific immune response is measured as a GMT of serum neutralizing antibodies to hPIV3, and wherein the GMT in serum neutralizing antibodies to hPIV3 increases in the subject at least 2 fold within 30 days relative to baseline, following a single 25 μg dose or a single 75 μg dose of the vaccine composition. In some embodiments, the antigen-specific immune response is measured as a GMT of serum neutralizing antibodies to hPIV3, and wherein the GMT in serum neutralizing antibodies to hPIV3 increases in the subject at least 3 fold within 30 days relative to baseline. In some embodiments, the antigen-specific immune response is measured as a GMT of serum neutralizing antibodies to hPIV3, and wherein the GMT in serum neutralizing antibodies to hPIV3 increases in the subject at least 3 fold within 30 days relative to baseline, following a single 25 μg dose or a single 75 μg dose of the vaccine composition.

In some embodiments, administration of the vaccine composition elicits serum neutralizing antibody titers against hMPV, including hMPV-A and hMPV-B, and hPIV3 that persist for at least 196 days post administration.

In some embodiments, administration of the vaccine composition elicits serum neutralizing antibody titers against hMPV, including hMPV-A and hMPV-B, that persist for at least 13 months post administration.

In some embodiments, administration of a second dose of the vaccine composition has negligible impact on the magnitude of hMPV or hPIV3 serum neutralizing antibody titers.

In some embodiments, the ionizable cationic lipid comprises Compound I:

(Compound I)

In some embodiments, the lipid nanoparticle comprises 45-55 mole percent ionizable cationic lipid, 5-15 mole percent DSPC, 35-40 mole percent cholesterol, and optionally 1-2 mole percent DMG-PEG. In some embodiments, the lipid nanoparticle comprises 50 mole percent ionizable cationic lipid, 10 mole percent DSPC, 38.5 mole percent cholesterol, and 1.5 mole percent DMG-PEG.

In some embodiments, the ratio of the mRNA encoding hMPV F glycoprotein to the mRNA encoding hPIV3 F glycoprotein in the vaccine composition is 1:1.

In some embodiments, the mRNA encoding hMPV F glycoprotein and the mRNA encoding hPIV3 F glycoprotein comprise a 1-methylpseudouridine chemical modification.

In some embodiments, the mRNA encoding hMPV F glycoprotein comprises an open reading frame that comprises a nucleotide sequence having at least 90% identity to the sequence of SEQ ID NO: 7. In some embodiments, the mRNA encoding hMPV F glycoprotein comprises an open reading frame that comprises the nucleotide sequence of sequence of SEQ ID NO: 7. In some embodiments, the mRNA encoding hMPV F glycoprotein comprises a nucleotide sequence having at least 90% identity to the sequence of SEQ ID NO: 1. In some embodiments, the mRNA encoding hMPV F glycoprotein comprises the nucleotide sequence of SEQ ID NO: 1.

In some embodiments, the mRNA encoding hPIV3 F glycoprotein comprises an open reading frame that comprises a nucleotide sequence having at least 90% identity to the sequence of SEQ ID NO: 9. In some embodiments, the mRNA encoding hPIV3 F glycoprotein comprises an open reading frame that comprises the nucleotide sequence of sequence of SEQ ID NO: 9. In some embodiments, the mRNA encoding hPIV3 F glycoprotein comprises a nucleotide sequence having at least 90% identity to the sequence of SEQ ID NO: 2. In some embodiments, the mRNA encoding hPIV3 F glycoprotein comprises the nucleotide sequence of SEQ ID NO: 2.

In some embodiments, the vaccine composition is administered via intramuscular injection.

In some embodiments, the vaccine composition further comprises a mRNA encoding a respiratory syncytial virus (RSV) antigen formulated in a lipid nanoparticle.

It should be understood that the vaccine compositions of the present disclosure are not naturally-occurring. That is, the RNA polynucleotides encoding the respiratory virus antigens, as provided herein, do not occur in nature. It should also be understood that the RNA polynucleotides described herein are isolated from viral proteins and viral lipids as they exist in nature. Thus, as provided herein, vaccine composition comprising an RNA formulated in a lipid nanoparticle, for example, excludes viruses (i.e., the compositions are not, nor do they contain, viruses).

BRIEF DESCRIPTION OF THE DRAWINGS

FIG. 1 depicts an overview of the study design. IST—internal safety team; SMC—safety monitoring committee FIG. 2 depicts the dose-escalation phase of the study. BS—blood sample; 'visit' denotes clinical visit.

FIG. 3 depicts the dose-selection phase of the study. BS—blood sample; 'visit' denotes clinical visit.

FIGS. 4A-4C show graphs of neutralizing antibody (FIG. 4A, hMPV-A; FIG. 4B, hMPV-B; FIG. 4C, PIV 3) by dose level and visit day; Pre-Protocol (PP) immunogenicity set.

FIGS. 5A-5C show graphs of neutralizing antibody (FIG. 5A, hMPV-A; FIG. 5B, hMPV-B; FIG. 5C, PIV 3) by dose level (25 μg, 75 μg, 150 μg, or 300 μg), regimen (1-dose vs. 2-dose) and visit day (day 1, day 28, day 56, and day 196 post first dose); PP immunogenicity set.

FIG. 6 shows the relationship between day 1 titer and response to first hMPV/hPIV3 mRNA vaccination (day 28/day 1 titer ratio); PP immunogenicity set.

FIGS. 7A-7C show neutralizing antibody kinetics by dose level and regimen (1-dose vs. 2-dose); PP immunogenicity set. FIG. 7A: hMPV-A neutralizing antibody. FIG. 7B: hMPV-B neutralizing antibody. FIG. 7C: PIV3 neutralizing antibody.

FIG. 8 shows a schematic of the study design of a Phase 1b, randomized, observer-blinded, placebo-controlled, dose-ranging trial.

DETAILED DESCRIPTION

Results from the clinical trial data provided herein demonstrate that a single hMPV/hPIV3 mRNA vaccination of the present disclosure elicited a boost in serum neutralization titers against both human metapneumovirus (hMPV) and human parainfluenza virus type 3 (hPIV3) at all dose levels tested (25, 75, 150 and 300 μg) with no apparent dose response. The geometric mean ratio (GMR) of Month 1 (28 days) to baseline titers in dose groups >75 μg ranged from 4.87-7.73 for hMPV (e.g., 6.04 for hMPV-A and 6.33 for hMPV-B) and from 3.13-3.36 for PIV3 (e.g., 3.24). A second hMPV/hPIV3 mRNA vaccination at Month 1 had negligible impact on the magnitude of hMPV or PIV3 neutralization titers. PIV3 neutralizing antibody titers remained above baseline at all dose levels tested through Month 7 (the pooled GMR was 2.03 at Month 7), while hMPV neutralizing antibody titers remained above baseline at all dose levels tested through Month 13 (the pooled GMR was 1.87 for hMPV-A and 2.91 for hMPV-B). These results demonstrate that the hMPV/hPIV3 mRNA vaccine provided herein is immunogenic at the lowest dose level tested and that the neutralizing antibody response reached a plateau. This hMPV/hPIV3 mRNA vaccine is the first known vaccine targeting both hMPV and PIV3. The few other investigational vaccines that have been evaluated targeting either hMPV or PIV3 are all live-attenuated or chimeric viruses, and none have induced significant antibody responses in adults. Given the similarities between hMPV, PIV3, and respiratory syncytial virus (RSV), it is also informative to benchmark the hMPV/hPIV3 mRNA vaccination of the present disclosure against the many investigational RSV vaccines that have been evaluated in adults. Such an analysis suggests that the hMPV/hPIV3 mRNA vaccine provided herein is at least as immunogenic as most RSV vaccines (including RSV mRNA vaccines), with the PIV3 response roughly equivalent, and the hMPV response superior.

Only one hMPV vaccine has been evaluated in the clinic; the National Institute of Allergy and Infectious Diseases (NIAID) evaluated a live-attenuated hMPV vaccine in a phase 1 study. A single dose was administered intranasally to adults, seropositive children and seronegative children. As expected, vaccine replication was restricted in adults and seropositive children, and therefore did not induce an antibody response. However, the vaccine was also over-attenuated in seronegative children, and induced seroconversion in a minority of these subjects. It is thought that this program is still active, however there are no known ongoing clinical studies.

Four different live-attenuated PIV3 vaccines have been developed by NIAID and tested in clinical studies. Two of these vaccines were partnered with MedImmune (MEDI-560, MEDI-534), one of which also includes the F antigen from RSV. All vaccines were administered intranasally. Many (>10) phase 1 studies have been conducted over the past ~30 years, in populations including adults, seropositive children, seronegative children, and unscreened infants. A few progressed to phase 2. Generalizing the results of these phase 1 and phase 2 studies: (1) vaccine replication was very restricted in adults and seropositive children and therefore little/no antibody response was induced; and (2) the vaccines induced seroconversion in most seronegative children, with booster vaccine doses primarily increasing titers only in subjects with a low response to the first vaccination. These programs are not thought to be active, and there are no known ongoing clinical studies.

RSV is also responsible for substantial respiratory disease and associated hospitalizations in infants and young children, with an incidence approximately the sum of hMPV+PIV3. RSV is closely related to hMPV and PIV3, and is a member of the Pneumoviradae family with hMPV. RSV also has a F protein on the viral surface that is highly conserved and is a major target of protective RSV neutralizing antibodies. Given the similarities between hMPV, PIV3 and RSV, it is worthwhile to consider the immunogenicity of the hMPV/hPIV3 mRNA vaccine of the present disclosure relative to RSV vaccines. There is no licensed vaccine for RSV, but many institutions have investigational vaccines in their pipelines, spanning phase 1 to phase 3 studies. A variety of different vaccine modalities are being evaluated, including subunit vaccines, nucleic acid-based vaccines (including an RSV mRNA vaccine), nanoparticles vaccines, vectored vaccines, and live-attenuated vaccines. All candidates were evaluated in adults that are all seropositive, and humoral immunity is typically measured by RSV neutralizing antibody. Generally, most investigational RSV vaccines elicit a 2- to 5-fold rise in baseline neutralizing antibody titers.

While it is difficult to directly compare virus neutralization titers across institutions/studies/vaccines due to differences in neutralization assays and viruses. However, some general statements seem supported by the data described herein. The hMPV/hPIV3 mRNA vaccine of the present disclosure is the first known vaccine targeting both hMPV and PIV3 to be tested in a clinical study; the neutralizing antibody response elicited by the hMPV/hPIV3 mRNA vaccine in adults is superior to that induced by the other investigational hMPV or PIV3 vaccines evaluated in this age group; the boost in hMPV neutralization titers elicited by the hMPV/hPIV3 mRNA vaccine is superior to the boost in RSV neutralization titers by most RSV vaccines; and the boost in PIV3 neutralization titers elicited by the hMPV/hPIV3 mRNA vaccine of the present disclosure is roughly equivalent.

Further, the Phase 1 safety findings of the hMPV/hPIV3 mRNA vaccine provided herein in adults were generally consistent with Phase 1 safety profiles of other mRNA vaccines. These findings suggest that a dose level of less than 300 µg has acceptable safety and tolerability.

Data from animal models and humans suggest that neutralizing antibodies are important for protection against hMPV and PIV3, although correlates have not been established in vaccine efficacy studies. The fusion (F) protein of hMPV and PIV3 are present on the viral surfaces, are highly conserved on an amino acid level within each virus, and are dominant targets of protective neutralizing antibodies. The hMPV/hPIV3 mRNA vaccine of the present disclosure, in some embodiments, includes two distinct mRNA sequences that encode the full-length membrane-bound F proteins of hMPV and PIV3, in a 1:1 target mass ratio. The mRNA vaccine provided herein, which comprises mRNA encoding hMPV and mRNA encoding hPIV3 (e.g., on the same mRNA molecule or on separate mRNA molecules), is referred to as the "mRNA hMPV/hPIV3 vaccine."

Infants acquire hMPV- and PIV3-specific antibodies from their mothers, and these antibodies are thought to provide substantial protection against hMPV- and PIV3-associated respiratory disease during the very first months of life. As maternal antibody wanes, disease incidence/severity tends to increase, followed by acquisition of natural immunity and a corresponding reduction of incidence/severity. Prior infection does not always prevent re-infection, although disease severity is typically less, particularly in immune competent healthy adults and older children. Secondary infections can boost neutralizing antibody titers, particularly if baseline titers are low. The vast majority of adults have been infected at least once with both hMPV and PIV3, and therefore are seropositive as measured by serum neutralizing antibody.

As shown in the Examples herein, humoral immunity was assessed in the hMPV/hPIV3 mRNA vaccine by three different microneutralization assays, hMPV-A, hMPV-B, and PIV3. A and B are the two lineages of hMPV, and were both evaluated to investigate the breadth of antibodies elicited by the hMPV/hPIV3 mRNA vaccine. The F protein is well conserved between hMPV-A and hMPV-B (~95% amino acid identity), so it was thought that antibodies primed by one would neutralize both. Indeed, the hMPV/hPIV3 mRNA vaccine effectively boosted antibodies that neutralized hMPV-A and hMPV-B.

Neutralizing antibodies against hMPV-A, hMPV-B, and PIV3 were detected at baseline (Day 1, prior to vaccination) in all hMPV/hPIV3 mRNA vaccinated subjects. The magnitude of baseline neutralizing antibody titers against hMPV-A and hMPV-B was similar (geometric mean titers [GMT]=3088.4 and 4453.2, respectively), given the ability of serum antibodies to cross-neutralize both hMPV lineages. The baseline neutralizing titer against PIV3 (GMT=378.4) was lower than that against hMPV. However, comparison of titers between the hMPV and PIV3 microneutralization assays was caveated by technical and biological differences in the assays and viruses. For example, hMPV forms foci of infected cells in culture, whereas PIV3 rapidly spreads throughout a cell monolayer.

Human metapneumovirus (hMPV) is a negative-sense, single-stranded RNA virus of the genus *Pneumovirinae* and of the family Paramyxoviridae and is closely related to the avian metapneumovirus (AMPV) subgroup C. It was isolated for the first time in 2001 in the Netherlands by using the RAP-PCR (RNA arbitrarily primed PCR) technique for identification of unknown viruses growing in cultured cells. hMPV is second only to RSV as an important cause of viral lower respiratory tract illness (LRI) in young children. The seasonal epidemiology of hMPV appears to be similar to that of RSV, but the incidence of infection and illness appears to be substantially lower. hMPV shares substantial homology with respiratory syncytial virus in its surface glycoproteins. hMPV fusion (F) glycoprotein is related to other paramyxovirus fusion glycoproteins and appears to have homologous regions that may have similar functions. The hMPV fusion glycoprotein amino acid sequence contains features characteristic of other paramyxovirus F glycoproteins, including a putative cleavage site and potential N-linked glycosylation sites. Paramyxovirus fusion proteins are synthesized as inactive precursors (F0) that are cleaved by host cell proteases into the biologically fusion-active F1 and F2 domains (see, e.g., Cseke G. et al. Journal of Virology 2007; 81(2): 698-707, incorporated herein by reference). Fusion glycoproteins are major antigenic determinants for all known paramyxoviruses and for other viruses that possess similar fusion proteins such as human immunodeficiency virus, influenza virus, and Ebola virus.

Human parainfluenza virus type 3 (hPIV3), like hMPV, is also a negative-sense, single-stranded sense RNA virus of the genus *Pneumovirinae* and of the family Paramyxoviridae and is a major cause of ubiquitous acute respiratory infections of infancy and early childhood. Its incidence peaks around 4-12 months of age, and the virus is responsible for 3-10% of hospitalizations, mainly for bronchiolitis and pneumonia. hPIV3 can be fatal, and in some instances is associated with neurologic diseases, such as febrile seizures. It can also result in airway remodeling, a significant cause of morbidity. In developing regions of the world, infants and young children are at the highest risk of mortality, either from primary hPIV3 viral infection or from secondary consequences, such as bacterial infections. hPIV3 F glycoprotein is located on the viral envelope, where it facilitates the viral fusion and cell entry. The F glycoprotein is initially inactive, but proteolytic cleavage leads to its active forms, F1 and F2, which are linked by disulfide bonds. This occurs when the HN protein binds its receptor on the host cell's surface. During early phases of infection, the F glycoprotein mediates penetration of the host cell by fusion of the viral envelope to the plasma membrane. In later stages of the infection, the F glycoprotein facilitates the fusion of the infected cells with neighboring uninfected cells, which leads to the formation of a syncytium and spread of the infection.

It should be understood that the term "hMPV/hPIV3" encompasses "hMPV and hPIV3" as well as "hMPV or PIV3."

Antigens

Antigens are proteins capable of inducing an immune response (e.g., causing an immune system to produce antibodies against the antigens). Herein, use of the term antigen encompasses immunogenic proteins and immunogenic fragments (an immunogenic fragment that induces (or is capable of inducing) an immune response to hMPV/hPIV3), unless otherwise stated. It should be understood that the term "protein" encompasses peptides and the term "antigen" encompasses antigenic fragments.

The hMPV/hPIV3 antigens of the mRNA vaccine of the present disclosure are provided in the Sequence Listing elsewhere herein. In some embodiments, the hMPV/hPIV3 mRNA vaccine comprises a mRNA comprising the open reading frame (ORF) sequence of SEQ ID NO: 7. In some embodiments, the hMPV/hPIV3 mRNA vaccine comprises a mRNA comprising the ORF sequence of SEQ ID NO: 9. In some embodiments, the mRNA encoding the hMPV F glycoprotein comprises the sequence of SEQ ID NO: 1. In some embodiments, the mRNA encoding the hPIV3 F glycoprotein comprises the sequence of SEQ ID NO: 2. In some embodiments, the hMPV F glycoprotein comprises the sequence of SEQ ID NO: 8. In some embodiments, the hPIV3 F glycoprotein comprises the sequence of SEQ ID NO: 10. In some embodiments, the aforementioned mRNAs may further comprise a 5' cap (e.g., 7mG(5')ppp(5')NlmpNp), a polyA tail (e.g., ~100 nucleotides), or a 5' cap and a polyA tail.

It should be understood that the hMPV/hPIV3 mRNA vaccine of the present disclosure may comprise a signal sequence. It should also be understood that the hMPV/hPIV3 mRNA vaccine of the present disclosure may include any 5' untranslated region (UTR) and/or any 3' UTR. Exemplary UTR sequences are provided in the Sequence Listing; however, other UTR sequences (e.g., of the prior art) may be used or exchanged for any of the UTR sequences described herein. UTRs may also be omitted from the vaccine constructs provided herein.

Nucleic Acids

The hMPV/hPIV3 mRNA vaccine of the present disclosure comprise at least one (one or more) ribonucleic acid (RNA) having an open reading frame encoding at least one hMPV/hPIV3 antigen. In some embodiments, the RNA is a messenger RNA (mRNA) having an open reading frame encoding at least one hMPV/hPIV3 antigen. In some embodiments, the RNA (e.g., mRNA) further comprises a (at least one) 5' UTR, 3' UTR, a polyA tail and/or a 5' cap.

Nucleic acids comprise a polymer of nucleotides (nucleotide monomers), also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ or ex vivo. The skilled artisan will appreciate that, except where otherwise noted, nucleic acid sequences set forth in the instant application may recite "T"'s in a representative DNA sequence but where the sequence represents RNA (e.g., mRNA), the "T"'s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure.

Variants

In some embodiments, the hMPV/hPIV3 mRNA vaccine of the present disclosure encodes an hMPV/hPIV3 antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a hMPV/hPIV3 mRNA vaccine comprises an mRNA ORF having a nucleotide sequence identified by any one of the sequences provided herein (see e.g., Sequence Listing), or having a nucleotide sequence at least 80%, at least 85%, at least 90%, at least 95%, at least 96%, at least 97%, at least 98%, or at least 99% identical to a nucleotide sequence identified by any one of the sequence provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of hMPV/hPIV3 antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the hMPV/hPIV3 pathogen. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, the hMPV/hPIV3 mRNA vaccine includes at least one RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp (5') G [the ARCA cap]; G(5')ppp(5')A; G(5')ppp(5')G; m7G (5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G (5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, the hMPV/hPIV3 mRNA vaccine includes one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the hMPV/hPIV3 mRNA vaccine includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, the hMPV/hPIV3 mRNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

The hMPV/hPIV3 mRNA vaccine may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, the hMPV/hPIV3 mRNA vaccine has one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Signal Peptides

In some embodiments, a hMPV/hPIV3 mRNA vaccine comprises a mRNA having an ORF that encodes a signal peptide fused to the hMPV/hPIV3 antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than hMPV/hPIV3 antigens in nature) are known in the art and can be tested for desired properties and then incorporated into a nucleic acid of the disclosure. In some embodiments, the signal peptide may comprise one of the following sequences: MDSKGSSQ-KGSRLLLLLVVSNLLLPQGVVG (SEQ ID NO: 11), MDWTWILFLVAAATRVHS (SEQ ID NO: 12); METPAQ-LLFLLLLWLPDTTG (SEQ ID NO: 13); MLGSNSGQRV-VFTILLLLVAPAYS (SEQ ID NO: 14); MKCLLYLAFL-FIGVNCA (SEQ ID NO: 15); MWLVSLAIVTACAGA (SEQ ID NO: 16).

Fusion Proteins

In some embodiments, the hMPV/hPIV3 mRNA vaccine of the present disclosure includes a mRNA encoding an antigenic fusion protein. Thus, the encoded antigen or antigens may include two or more proteins (e.g., protein and/or protein fragment) joined together. In some embodiments, the mRNA encodes a hMPV F glycoprotein fused to a hPIV3 F glycoprotein. Alternatively, the protein to which a protein antigen is fused does not promote a strong immune response to itself, but rather to the hMPV/hPIV3 antigen. Antigenic fusion proteins, in some embodiments, retain the functional property from each original protein.

Scaffold Moieties

The RNA (e.g., mRNA) vaccines as provided herein, in some embodiments, encode fusion proteins that comprise hMPV/hPIV3 antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. Computational and Structural Biotechnology Journal 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments the hMPV/hPIV3 antigen is fused to HBsAG or HBcAG to facilitate self-assembly of nanoparticles displaying the hMPV/hPIV3 antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. J Mol Biol. 2009; 390:83-98). Several high-resolution structures of ferritin have been determined, confirming that Helicobacter pylori ferritin is made of 24 identical protomers, whereas in animals, there are ferritin light and heavy chains that can assemble alone or combine with different ratios into particles of 24 subunits (Granier T. et al. J Biol Inorg Chem. 2003; 8:105-111; Lawson D. M. et al. Nature. 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. Flavins and Flavoproteins. Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. J Mol Biol. 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. Nat Struct Mol Biol. 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. FEBS J. 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a hMPV/hPIV3 antigen). In some embodiments, a codon optimized sequence shares less than 90% sequence identity to a naturally-occurring or wild-type sequence (e.g., a naturally-occurring or wild-type mRNA sequence encoding a hMPV/hPIV3 antigen). In some embodiments, a codon optimized sequence shares less than 85% sequence identity to a naturally-occurring or wild-type sequence (e.g., a naturally-occurring or wild-type mRNA sequence encoding a hMPV/hPIV3 antigen). In some embodiments, a codon optimized sequence shares less than 80% sequence identity to a naturally-occurring or wild-type sequence (e.g., a naturally-occurring or wild-type mRNA sequence encoding a hMPV/hPIV3 antigen). In some embodiments, a codon optimized sequence shares less than 75% sequence identity to a naturally-occurring or wild-type sequence (e.g., a naturally-occurring or wild-type mRNA sequence encoding a hMPV/hPIV3 antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a hMPV/hPIV3 antigen). In some embodiments, a codon optimized sequence shares between 65% and 75% or about 80% sequence identity to a naturally-occurring or wild-type sequence (e.g., a naturally-occurring or wild-type mRNA sequence encoding a hMPV/hPIV3 antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a hMPV/hPIV3 antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of the hMPV/hPIV3 mRNA vaccine of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

The hMPV/hPIV3 mRNA vaccine of the present disclosure comprise, in some embodiments, at least one nucleic acid (e.g., RNA) having an open reading frame encoding at least one hMPV/hPIV3 antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (w). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 17), where R is a purine (adenine or guanine) three bases upstream of the start codon (AUG), which is followed by another 'G'0.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include Xenopus or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 18) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (1743) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 3 and SEQ ID NO: 4.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 19) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

3' UTRs may be heterologous or synthetic. With respect to 3' UTRs, globin UTRs, including Xenopus β-globin UTRs and human β-globin UTRs are known in the art (U.S. Pat. Nos. 8,278,063, 9,012,219, US20110086907). A modified β-globin construct with enhanced stability in some cell types by cloning two sequential human β-globin 3'UTRs head to tail has been developed and is well known in the art (US2012/0195936, WO2014/071963). In addition a2-globin, a1-globin, UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014152774), rabbit β globin and hepatitis B virus (HBV), α-globin 3' UTR and Viral VEEV 3' UTR sequences are also known in the art. In some embodiments, the sequence UUUGAAUU (WO2014144196) is used. In some embodiments, 3' UTRs of human and mouse ribosomal protein are used. Other examples include rps9 3'UTR (WO2015101414), FIG. 4 (WO2015101415), and human albumin 7 (WO2015-101415).

In some embodiments, a 3' UTR of the present disclosure comprises a sequence selected from SEQ ID NO: 5 and SEQ ID NO: 6.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO/2014/152027, which is incorporated by reference herein in its entirety.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide, for example, but not limited to hMPV/hPIV3 mRNA. In some embodiments, cells, e.g., bacterial cells, e.g., E. coli, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis.

The synthesis of nucleic acids of the present disclosure by the sequential addition of monomer building blocks may be carried out in a liquid phase.

Combination of Synthetic Methods.

The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the hMPV/hPIV3 mRNA vaccine of the disclosure is formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

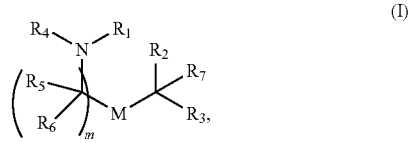

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O) OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- or 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

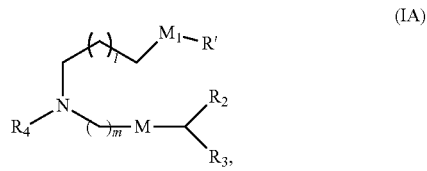

(IA)

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-4}$ alkyl, and $C_{2-14}$ alkenyl.

In some embodiments, a subset of compounds of Formula (I) includes those of Formula (II):

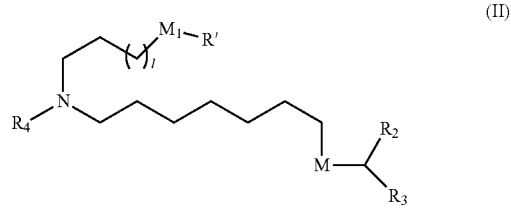

(II)

or a salt or isomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

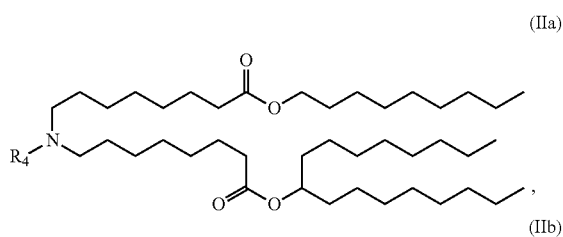

(IIa)

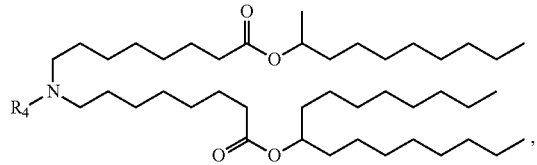

(IIb)

33

-continued

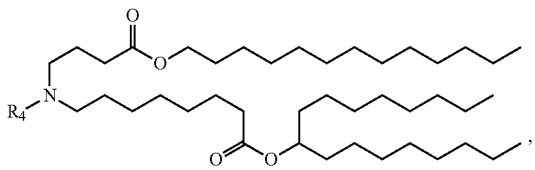
(IIc)

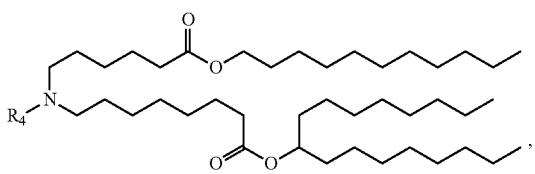
(IId)

or a salt or isomer thereof, wherein $R_4$ is as described herein.

In some embodiments, a subset of compounds of Formula (I) includes those of Formula (IId):

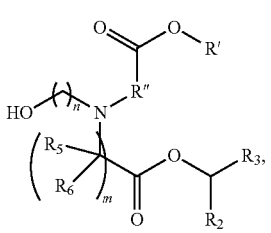
(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

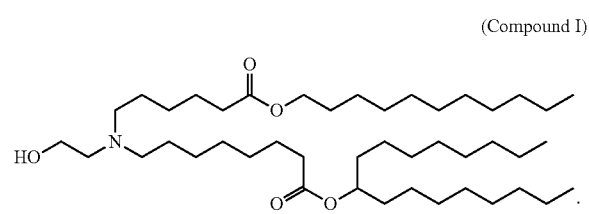 [SMILES: CCCCCCCCCCCOC(=O)CCCCCN(CCO)CCCCCCCC(=O)OC(CCCCCCCC)CCCCCCCC]
(Compound I)

In some embodiments, an ionizable cationic lipid of the disclosure comprises a compound having structure:

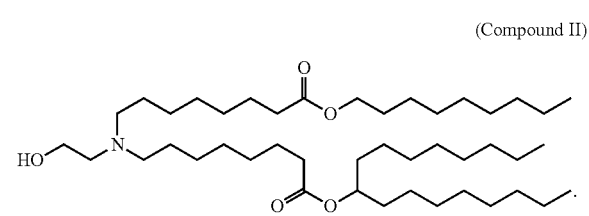 [SMILES: CCCCCCCCCOC(=O)CCCCCCCN(CCO)CCCCCCCC(=O)OC(CCCCCCCC)CCCCCCCC]
(Compound II)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DL-PC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is DMG-PEG.

In some embodiments, the lipid nanoparticle comprises 45-55 mole percent ionizable cationic lipid. For example, lipid nanoparticle may comprise 45, 46, 47, 48, 49, 50, 51, 52, 53, 54, or 55 mole percent ionizable cationic lipid.

In some embodiments, the lipid nanoparticle comprises 5-15 mole percent DSPC. For example, the lipid nanoparticle may comprise 5, 6, 7, 8, 9, 10, 11, 12, 13, 14, or 15 mole percent DSPC.

In some embodiments, the lipid nanoparticle comprises 35-40 mole percent cholesterol. For example, the lipid nanoparticle may comprise 35, 36, 37, 38, 39, or 40 mole percent cholesterol.

In some embodiments, the lipid nanoparticle comprises 1-2 mole percent DMG-PEG. For example, the lipid nanoparticle may comprise 1, 1.5, or 2 mole percent DMG-PEG.

In some embodiments, the lipid nanoparticle comprises 50 mole percent ionizable cationic lipid, 10 mole percent DSPC, 38.5 mole percent cholesterol, and 1.5 mole percent DMG-PEG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The hMPV/hPIV3 vaccines, as provided herein, may include mRNA or multiple mRNAs encoding two or more antigens of the same or different hMPV/hPIV3 species. In some embodiments, the hMPV/hPIV3 vaccine includes an RNA or multiple RNAs encoding two or more antigens. In some embodiments, the mRNA of a hMPV/hPIV3 vaccine may encode 1, 2, 3, 4, 5, 6, 7, 8, 9, 10, 11, 12, or more antigens.

In some embodiments, the hMPV/hPIV3 mRNA vaccine comprises at least one RNA encoding a hMPV F glycoprotein and a hPIV3 F glycoprotein antigen.

In some embodiments, two or more different RNA (e.g., mRNA) encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The hMPV/hPIV3 mRNA vaccines, as provided herein, may include an RNA or multiple RNAs encoding two or more antigens of the same or different hMPV/hPIV3 strains. Also provided herein are combination vaccines that include RNA encoding one or more hMPV/hPIV3 antigen(s) and one or more antigen(s) of a different organisms. Thus, the vaccines of the present disclosure may be combination vaccines that target one or more antigens of the same strain/species, or one or more antigens of different strains/species, e.g., antigens which induce immunity to organisms which are found in the same geographic areas where the risk of hMPV/hPIV3 infection is high or organisms to which an individual is likely to be exposed to when exposed to hMPV/hPIV3.

Pharmaceutical Formulations

Provided herein are compositions (e.g., pharmaceutical compositions), methods, kits and reagents for prevention or treatment of hMPV/hPIV3 in humans and other mammals, for example. hMPV/hPIV3 mRNA vaccines can be used as therapeutic or prophylactic agents. They may be used in medicine to prevent and/or treat infectious disease.

In some embodiments, the hMPV/hPIV3 vaccine containing mRNA as described herein can be administered to a subject (e.g., a mammalian subject, such as a human subject), and the RNA polynucleotides are translated in vivo to produce an antigenic polypeptide (antigen).

An "effective amount" of a hMPV/hPIV3 vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a hMPV/hPIV3 mRNA vaccine provides an induced or boosted immune response as a function of antigen production in the cells of the subject. In some embodiments, an effective amount of the hMPV/hPIV3 mRNA vaccine containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of hMPV/hPIV3. The hMPV/hPIV3 mRNA vaccine may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

The hMPV/hPIV3 mRNA vaccine may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, the hMPV/hPIV3 mRNA vaccine may be administered intramuscularly, intranasally or intradermally, similarly to the administration of inactivated vaccines known in the art.

The hMPV/hPIV3 mRNA vaccine may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including the hMPV/hPIV3 mRNA vaccine and/or complexes optionally in combination with one or more pharmaceutically acceptable excipients.

The hMPV/hPIV3 mRNA vaccine may be formulated or administered alone or in conjunction with one or more other components. For instance, the hMPV/hPIV3 mRNA vaccine may comprise other components including, but not limited to, adjuvants.

In some embodiments, the hMPV/hPIV3 mRNA vaccine does not include an adjuvant (they are adjuvant free).

The hMPV/hPIV3 mRNA vaccine may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, the hMPV/hPIV3 mRNA vaccine are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the hMPV/hPIV3 mRNA vaccine is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the hMPV/hPIV3 mRNA vaccine (e.g., for transplantation into a subject), hyaluronidase, nanoparticle mimics and combinations thereof.

Dosing/Administration

Provided herein are compositions (e.g., pharmaceutical compositions), methods, kits and reagents for prevention and/or treatment of hMPV/hPIV3 in humans and other mammals. The hMPV/hPIV3 vaccine can be used as therapeutic or prophylactic agents. In some aspects, the RNA vaccines of the disclosure are used to provide prophylactic protection from hMPV/hPIV3. In some aspects, the RNA vaccines of the disclosure are used to treat a hMPV/hPIV3 infection. In some embodiments, the hMPV/hPIV3 mRNA vaccine of the present disclosure is used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the hMPV/hPIV3 mRNA vaccine is administered to a subject (e.g., a mammalian subject, such as a human subject) in an effective amount to induce an antigen-specific immune response. The RNA encoding the hMPV/hPIV3 antigen is expressed and translated in vivo to produce the antigen, which then stimulates an immune response in the subject.

Prophylactic protection from hMPV/hPIV3 can be achieved following administration of the hMPV/hPIV3 mRNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against hMPV/hPIV3 is provided in aspects of the present disclosure. The method involves administering to the subject a hMPV/hPIV3 mRNA vaccine comprising at least one RNA (e.g., mRNA) having an open reading frame encoding at least one hMPV/hPIV3 antigen, thereby inducing in the subject an immune response specific to a hMPV/hPIV3 antigen, wherein anti-antigen antibody titer in the subject is increased following vaccination relative to anti-antigen antibody titer in a subject vaccinated with a prophylactically effective dose of a traditional vaccine against the hMPV/ hPIV3. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the hMPV/hPIV3 or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the hMPV/hPIV3 or an unvaccinated subject.

A method of eliciting an immune response in a subject against hMPV/hPIV3 is provided in other aspects of the disclosure. The method involves administering to the subject the hMPV/hPIV3 mRNA vaccine comprising at least one RNA polynucleotide having an open reading frame encoding at least one hMPV/hPIV3 antigen, thereby inducing in the subject an immune response specific to hMPV/hPIV3 antigen, wherein the immune response in the subject is equivalent to an immune response in a subject vaccinated with a traditional vaccine against the hMPV/hPIV3 at 2 times to 100 times the dosage level relative to the RNA vaccine.

In some embodiments, the immune response in the subject is equivalent to an immune response in a subject vaccinated with a traditional vaccine at twice the dosage level relative to the hMPV/hPIV3 mRNA vaccine. In some embodiments, the immune response in the subject is equivalent to an immune response in a subject vaccinated with a traditional vaccine at three times the dosage level relative to the hMPV/hPIV3 mRNA vaccine. In some embodiments, the immune response in the subject is equivalent to an immune response in a subject vaccinated with a traditional vaccine at 4 times, 5 times, 10 times, 50 times, or 100 times the dosage level relative to the hMPV/hPIV3 mRNA vaccine. In some embodiments, the immune response in the subject is equivalent to an immune response in a subject vaccinated with a traditional vaccine at 10 times to 1000 times the dosage level relative to the hMPV/hPIV3 mRNA vaccine. In some embodiments, the immune response in the subject is equivalent to an immune response in a subject vaccinated with a traditional vaccine at 100 times to 1000 times the dosage level relative to the hMPV/hPIV3 mRNA vaccine.

In other embodiments, the immune response is assessed by determining [protein] antibody titer in the subject. In other embodiments, the ability of serum or antibody from an immunized subject is tested for its ability to neutralize viral uptake or reduce hMPV/hPIV3 transformation of human B lymphocytes. In other embodiments, the ability to promote a robust T cell response(s) is measured using art recognized techniques.

Other aspects the disclosure provide methods of eliciting an immune response in a subject against hMPV/hPIV3 by administering to the subject the hMPV/hPIV3 mRNA vaccine comprising at least one RNA polynucleotide having an open reading frame encoding at least one hMPV/hPIV3 antigen, thereby inducing in the subject an immune response specific to hMPV/hPIV3 antigen, wherein the immune response in the subject is induced 2 days to 10 weeks earlier relative to an immune response induced in a subject vaccinated with a prophylactically effective dose of a traditional vaccine against hMPV/hPIV3. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against a hMPV/hPIV3 by administering to the subject the hMPV/hPIV3 mRNA vaccine having an open reading frame encoding a first antigen, wherein the RNA polynucleotide does not include a stabilization element, and wherein an adjuvant is not co-formulated or co-administered with the vaccine.

The hMPV/hPIV3 mRNA vaccine may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The hMPV/hPIV3 mRNA vaccine is typically formulated in dosage unit form for ease of administration and uniformity of dosage. It will be understood, however, that the total daily usage of the hMPV/hPIV3 mRNA vaccine may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, the subject is an adult subject. An adult subject is any human subject who has an age of 18 years or older. In some embodiments, an adult subject is between the ages of 18 to 49 years (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 years). In some embodiments, an adult subject is between the ages of 18 and 65 years. In some embodiments, an adult subject is a geriatric subject who has an age of at least 65 years.

In other embodiments, the subject is a pediatric subject. A pediatric subject is any human subject who has an age of younger than 18 years. In some embodiments, a pediatric subject is between the ages of 12 months and 36 months. In some embodiments, a pediatric subject is between the ages of 1 year and 17 years (e.g., 1, 2, 3, 4, 5, 6, 7, 8, 9, 10, 11, 12, 13, 14, 15, 16, or 17 years). In some embodiments, a pediatric subject has an age of 10 years or younger (e.g., 6 months to 10 years, or 12 months to 10 years). In some embodiments, a pediatric subject has an age of 5 years or younger (e.g., 6 months to 5 years, or 12 months to 5 years).

The effective amount of the hMPV/hPIV3 mRNA vaccine, as provided herein, may be as low as 10 μg, administered for example as a single dose or as two 5 μg doses. In some embodiments, the effective amount of the hMPV/hPIV3 mRNA vaccine, as provided herein, may be as low as 20 μg, administered for example as a single dose or as two 10 μg doses. In some embodiments, the effective amount is a total dose of 10 μg-300 μg or 20 μg-300 μg or 25 μg-300 μg. For example, the effective amount may be a total dose of 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 160 μg, 170 μg, 180 μg, 190 μg, 200 μg, 250 μg, or 300 μg. In some embodiments, the effective amount is a total dose of 10 μg-300 μg. In some embodiments, the effective amount is a total dose of 10 μg. In some embodiments, the effective amount is a total dose of 20 μg. In some embodiments, the effective amount is a total dose of 25 μg. In some embodiments, the effective amount is a total dose of 30 μg. In some embodiments, the effective amount is a total dose of 75 μg. In some embodiments, the effective amount is a total dose of 100 μg. In some embodiments, the effective amount is a total dose of 150 μg. In some embodiments, the effective amount is a total dose of 300 μg.

In some embodiments, the hMPV/hPIV3 mRNA vaccine is administered to an adult human subject. The effective amount of the hMPV/hPIV3 mRNA vaccine for the adult subject, as provided herein, may be as low as 20 μg, administered for example as a single dose or as two 10 μg doses. In some embodiments, the effective amount is a total dose of 20 μg-300 μg, 25 μg-300 μg, or 30 μg-300 μg. For example, the effective amount may be a total dose of 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 250 μg, or 300 μg. In some embodiments, the effective amount is a total dose of 25 μg-300 μg. In some embodiments, the effective amount is a total dose of 20 μg. In some embodiments, the effective amount is a total dose of 30 μg. In some embodiments, the effective amount is a total dose of 25 μg. In some embodiments, the effective amount is a total dose of 75 μg. In some embodiments, the effective amount is a total dose of 150 μg. In some embodiments, the effective amount is a total dose of 300 μg.

In some embodiments, the hMPV/hPIV3 mRNA vaccine is administered to pediatric human subject. The effective amount of the hMPV/hPIV3 mRNA vaccine for the pediatric subject, as provided herein, may be as low as 10 μg, administered for example as a single dose or as two 5 μg doses. In some embodiments, the effective amount is a total dose of 10 μg-150 μg or 20 μg-150 μg or 30 μg-150 μg. For example, the effective amount may be a total dose of 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, or 150 μg. In some embodiments, the effective amount is a total dose of 10 μg-150 μg. In some embodiments, the effective amount is a total dose of 10 μg. In some embodiments, the effective amount is a total dose of 30 μg. In some embodiments, the effective amount is a total dose of 100 μg. The hMPV/hPIV3 mRNA vaccine described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the hMPV/hPIV3 mRNA vaccine, wherein the hMPV/hPIV3 mRNA vaccine is formulated in an effective amount to produce an antigen specific immune response in a subject (e.g., production of antibodies specific to an anti-hMPV/hPIV3 antigen). "An effective amount" is a dose of the hMPV/hPIV3 mRNA vaccine effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) hMPV/hPIV3 protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-hMPV/hPIV3 antigen antibody titer produced in a subject administered the hMPV/hPIV3 mRNA vaccine as provided herein. An antibody titer is a measurement of the amount of antibodies within a subject, for example, antibodies that are specific to a particular antigen (e.g., an anti-hMPV/hPIV3 antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the hMPV/hPIV3 mRNA vaccine.

In some embodiments, an anti-hMPV/hPIV3 antigen antibody titer produced in a subject is increased by at least 1 log relative to a control. For example, anti-hMPV/hPIV3 antigen antibody titer produced in a subject may be increased by at least 1.5, at least 2, at least 2.5, or at least 3 log relative to a control. In some embodiments, the anti-hMPV/hPIV3 antigen antibody titer produced in the subject is increased by 1, 1.5, 2, 2.5 or 3 log relative to a control. In some embodiments, the anti-hMPV/hPIV3 antigen antibody titer produced in the subject is increased by 1-3 log relative to a control. For example, the anti-hMPV/hPIV3 antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-hMPV/hPIV3 antigen antibody titer produced in a subject is increased at least 2 times relative to a control. For example, the anti-hMPV/hPIV3 antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-hMPV/hPIV3 antigen antibody titer produced in the subject is increased 2, 3, 4, 5, 6, 7, 8, 9, or 10 times relative to a control. In some embodiments, the anti-hMPV/hPIV3 antigen antibody titer produced in a subject is increased 2-10 times relative to a control. For example, the anti-hMPV/hPIV3 antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to hMPV and hPIV3. A geometric mean titer (GMT) is the average antibody titer for a group of subjects calculated by multiplying all values and taking the nth root of the number, where n is the number of subjects with available data.

In some embodiments, the GMR of 28 days to baseline titers for hMPV (e.g., hMPV-A and/or hMPV-B) in subjects administered a ≥25 µg, ≥30 µg, ≥75 µg, ≥150 µg, or ≥300 µg dose of the vaccine composition is in the range of 4 to 8. In some embodiments, the GMR of 28 days to baseline titers for hMPV (e.g., hMPV-A and/or hMPV-B) in pediatric subjects administered a ≥10 µg, ≥30 µg, or ≥100 µg dose of the vaccine composition is in the range of 3 to 9. In some embodiments, the GMR of 28 days to baseline titers for hMPV (e.g., hMPV-A and/or hMPV-B) in subjects administered a ≥75 µg dose of the vaccine composition is in the range of 4 to 8. For example, the GMR of 28 days to baseline titers for hMPV in subjects administered a ≥25 µg, ≥30 µg, ≥75 µg, ≥150 µg, or ≥300 µg dose of the vaccine composition may be 3, 3.5, 4, 4.5, 5, 5.5, 6, 6.5, 7, 7.5, 8, 8.5, or 9. In some embodiments, the GMR of 28 days to baseline titers for hMPV in pediatric subjects administered a ≥10 µg, ≥30 µg, or ≥100 µg dose of the vaccine composition may be 3, 3.5, 4, 4.5, 5, 5.5, 6, 6.5, 7, 7.5, 8, 8.5, or 9. In some embodiments, the GMR of 28 days to baseline titers for hMPV in subjects administered a ≥25 µg, ≥30 µg, ≥75 µg, ≥150 µg, or ≥300 µg dose of the vaccine composition is 3.53-8.52. In some embodiments, the GMR of 28 days to baseline titers for hMPV in subjects administered a ≥25 µg, ≥30 µg, ≥75 µg, ≥150 µg, or ≥300 µg dose of the vaccine composition is 6-6.5. For example, the GMR of 28 days to baseline titers for hMPV in subjects administered a ≥25 µg, ≥30 µg, ≥75 µg, ≥150 µg, or ≥300 µg dose of the vaccine composition may be 6, 6.1, 6.15, 6.2, 6.25, 6.3, 6.35, 6.4, 6.45, or 6.5. In some embodiments, the GMR of 28 days to baseline titers for hMPV (e.g., hMPV-A) in subjects administered a ≥25 µg, ≥30 µg, ≥75 µg, ≥150 µg, or ≥300 µg dose of the vaccine composition is 6.04. In some embodiments, the GMR of 28 days to baseline titers for hMPV (e.g., hMPV-B) in subjects administered a ≥25 µg, ≥30 µg, ≥75 µg, ≥150 µg, or ≥300 µg dose of the vaccine composition is 6.33.

In some embodiments, the GMR of 28 days to baseline titers for hPIV3 in subjects administered a ≥25 µg, ≥30 µg, ≥75 µg, ≥150 µg, or ≥300 µg dose of the vaccine composition is in the range of 2 to 5. In some embodiments, the GMR of 28 days to baseline titers for hPIV3 in pediatric subjects administered a ≥10 µg, ≥30 µg, or ≥100 µg dose of the vaccine composition is in the range of 2 to 5. In some embodiments, the GMR of 28 days to baseline titers for hPIV3 in subjects administered a ≥75 µg dose of the vaccine composition is in the range of 2 to 5. For example, the GMR of 28 days to baseline titers for hPIV3 in subjects administered a ≥25 µg, ≥30 µg, ≥75 µg, ≥150 µg, or ≥300 µg dose of the vaccine composition may be 2, 2.5, 3, 3.5, 4, 4.5, or 5. In some embodiments, the GMR of 28 days to baseline titers for hPIV3 in pediatric subjects administered a ≥10 µg, ≥30 µg, or ≥100 µg dose of the vaccine composition may be 2, 2.5, 3, 3.5, 4, 4.5, or 5. In some embodiments, the GMR of 28 days to baseline titers for hPIV3 in subjects administered a ≥25 µg, ≥30 µg, ≥75 µg, ≥150 µg, or ≥300 µg dose of the vaccine composition is 2.67-3.36. For example, the GMR of 28 days to baseline titers for hPIV3 in subjects administered a ≥25 µg, ≥30 µg, ≥75 µg, ≥150 µg, or ≥300 µg dose of the vaccine composition may be 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, or 3.55. In some embodiments, the GMR of 28 days to baseline titers for hPIV3 in subjects administered a ≥25 µg, ≥30 µg, ≥75 µg, ≥150 µg, or ≥300 µg dose of the vaccine composition is 3.24.

In some embodiments, the GMR of 28 days to baseline titers for hMPV-A in subjects administered a 75 µg dose of the vaccine composition is in the range of 4 to 6, e.g., 5.07. In some embodiments, the GMR of 28 days to baseline titers for hMPV-A in subjects administered a 150 µg dose of the vaccine composition is in the range of 4.5 to 6.5, e.g., 5.84. In some embodiments, the GMR of 28 days to baseline titers for hMPV-A in subjects administered a 300 µg dose of the vaccine composition is in the range of 6 to 8, e.g., 7.09. In some embodiments, the GMR of 56 days to baseline titers for hMPV-A in subjects administered a 75 µg dose of the vaccine composition is in the range of 3 to 5, e.g., 3.87. In some embodiments, the GMR of 56 days to baseline titers for hMPV-A in subjects administered a 150 µg dose of the vaccine composition is in the range of 3 to 5, e.g., 3.18. In some embodiments, the GMR of 56 days to baseline titers for hMPV-A in subjects administered a 300 µg dose of the vaccine composition is in the range of 5.5 to 7.5, e.g., 6.05. In some embodiments, the GMR of 196 days to baseline titers for hMPV-A in subjects administered a 75 µg dose of the vaccine composition is in the range of 1 to 3, e.g., 1.82. In some embodiments, the GMR of 196 days to baseline titers for hMPV-A in subjects administered a 150 µg dose of the vaccine composition is in the range of 2 to 4, e.g., 2.08. In some embodiments, the GMR of 196 days to baseline titers for hMPV-A in subjects administered a 300 µg dose of the vaccine composition is in the range of 2.5 to 4.5, e.g., 3.33.

In some embodiments, the GMR of 28 days to baseline titers for hMPV-B in subjects administered a 75 µg dose of the vaccine composition is in the range of 3.5 to 5.5, e.g., 4.87. In some embodiments, the GMR of 28 days to baseline titers for hMPV-B in subjects administered a 150 µg dose of the vaccine composition is in the range of 6.5 to 8.5, e.g., 7.73. In some embodiments, the GMR of 28 days to baseline titers for hMPV-B in subjects administered a 300 μg dose of the vaccine composition is in the range of 6 to 8, e.g., 7.01. In some embodiments, the GMR of 56 days to baseline titers for hMPV-B in subjects administered a 75 μg dose of the vaccine composition is in the range of 3 to 5, e.g., 4.14. In some embodiments, the GMR of 56 days to baseline titers for hMPV-B in subjects administered a 150 μg dose of the vaccine composition is in the range of 6 to 8, e.g., 6.58. In some embodiments, the GMR of 56 days to baseline titers for hMPV-B in subjects administered a 300 μg dose of the vaccine composition is in the range of 3.5 to 5.5, e.g., 4.24. In some embodiments, the GMR of 196 days to baseline titers for hMPV-B in subjects administered a 75 μg dose of the vaccine composition is in the range of 2 to 5, e.g., 3.06. In some embodiments, the GMR of 196 days to baseline titers for hMPV-B in subjects administered a 150 μg dose of the vaccine composition is in the range of 3 to 5, e.g., 3.47. In some embodiments, the GMR of 196 days to baseline titers for hMPV-B in subjects administered a 300 μg dose of the vaccine composition is in the range of 3 to 5, e.g., 3.93.

In some embodiments, the GMR of 28 days to baseline titers for hPIV3 in subjects administered a 75 μg dose of the vaccine composition is in the range of 2.5 to 4.5, e.g., 3.36. In some embodiments, the GMR of 28 days to baseline titers for hPIV3 in subjects administered a 150 μg dose of the vaccine composition is in the range of 2 to 4, e.g., 3.13. In some embodiments, the GMR of 28 days to baseline titers for hPIV3 in subjects administered a 300 μg dose of the vaccine composition is in the range of 2 to 4, e.g., 3.29. In some embodiments, the GMR of 56 days to baseline titers for hPIV3 in subjects administered a 75 μg dose of the vaccine composition is in the range of 2.5 to 4.5, e.g., 3.34. In some embodiments, the GMR of 56 days to baseline titers for hPIV3 in subjects administered a 150 μg dose of the vaccine composition is in the range of 1 to 3, e.g., 1.97. In some embodiments, the GMR of 56 days to baseline titers for hPIV3 in subjects administered a 300 μg dose of the vaccine composition is in the range of 2.5 to 4.5, e.g., 3.23. In some embodiments, the GMR of 196 days to baseline titers for hPIV3 in subjects administered a 75 μg dose of the vaccine composition is in the range of 1 to 3, e.g., 1.76. In some embodiments, the GMR of 196 days to baseline titers for hPIV3 in subjects administered a 150 μg dose of the vaccine composition is in the range of 1 to 3, e.g., 1.26. In some embodiments, the GMR of 196 days to baseline titers for hPIV3 in subjects administered a 300 μg dose of the vaccine composition is in the range of 1 to 3, e.g., 1.73.

In some embodiments, the GMR of 28 days to baseline titers for hMPV-A in subjects administered two 75 μg doses of the vaccine composition is in the range of 6 to 8, e.g., 7.06. In some embodiments, the GMR of 28 days to baseline titers for hMPV-A in subjects administered two 150 μg doses of the vaccine composition is in the range of 7 to 9, e.g., 8.16. In some embodiments, the GMR of 28 days to baseline titers for hMPV-A in subjects administered two 300 μg doses of the vaccine composition is in the range of 6 to 8, e.g., 6.99. In some embodiments, the GMR of 56 days to baseline titers for hMPV-A in subjects administered two 75 μg doses of the vaccine composition is in the range of 6.5 to 8.5, e.g., 7.56. In some embodiments, the GMR of 56 days to baseline titers for hMPV-A in subjects administered two 150 μg doses of the vaccine composition is in the range of 8.5 to 10.5, e.g., 9.82. In some embodiments, the GMR of 56 days to baseline titers for hMPV-A in subjects administered two 300 μg doses of the vaccine composition is in the range of 5.5 to 7.5, e.g., 5.86. In some embodiments, the GMR of 196 days to baseline titers for hMPV-A in subjects administered two 75 μg doses of the vaccine composition is in the range of 2 to 4, e.g., 3.10. In some embodiments, the GMR of 196 days to baseline titers for hMPV-A in subjects administered two 150 μg doses of the vaccine composition is in the range of 3.5 to 5.5, e.g., 4.48. In some embodiments, the GMR of 196 days to baseline titers for hMPV-A in subjects administered two 300 μg doses of the vaccine composition is in the range of 2 to 4, e.g., 2.89.

In some embodiments, the GMR of 28 days to baseline titers for hMPV-B in subjects administered two 75 μg doses of the vaccine composition is in the range of 3.5 to 5.5, e.g., 4.38. In some embodiments, the GMR of 28 days to baseline titers for hMPV-B in subjects administered two 150 μg doses of the vaccine composition is in the range of 6.5 to 8.5, e.g., 7.80. In some embodiments, the GMR of 28 days to baseline titers for hMPV-B in subjects administered two 300 μg doses of the vaccine composition is in the range of 7.5 to 9.5, e.g., 8.65. In some embodiments, the GMR of 56 days to baseline titers for hMPV-B in subjects administered two 75 μg doses of the vaccine composition is in the range of 4 to 6, e.g., 5.06. In some embodiments, the GMR of 56 days to baseline titers for hMPV-B in subjects administered two 150 μg doses of the vaccine composition is in the range of 9.5 to 11.5, e.g., 10.59. In some embodiments, the GMR of 56 days to baseline titers for hMPV-B in subjects administered two 300 μg doses of the vaccine composition is in the range of 7 to 9, e.g., 8.30. In some embodiments, the GMR of 196 days to baseline titers for hMPV-B in subjects administered two 75 μg doses of the vaccine composition is in the range of 1 to 3, e.g., 2.08. In some embodiments, the GMR of 196 days to baseline titers for hMPV-B in subjects administered two 150 μg doses of the vaccine composition is in the range of 5 to 7, e.g., 6.22. In some embodiments, the GMR of 196 days to baseline titers for hMPV-B in subjects administered two 300 μg doses of the vaccine composition is in the range of 3 to 5, e.g., 4.23.

In some embodiments, the GMR of 28 days to baseline titers for hPIV3 in subjects administered two 75 μg doses of the vaccine composition is in the range of 2 to 4, e.g., 2.78. In some embodiments, the GMR of 28 days to baseline titers for hPIV3 in subjects administered two 150 μg doses of the vaccine composition is in the range of 2 to 4, e.g., 3.39. In some embodiments, the GMR of 28 days to baseline titers for hPIV3 in subjects administered two 300 μg doses of the vaccine composition is in the range of 2.5 to 4.5, e.g., 3.54. In some embodiments, the GMR of 56 days to baseline titers for hPIV3 in subjects administered two 75 μg doses of the vaccine composition is in the range of 2.5 to 4.5, e.g., 3.60. In some embodiments, the GMR of 56 days to baseline titers for hPIV3 in subjects administered two 150 μg doses of the vaccine composition is in the range of 2.5 to 4.5, e.g., 3.74. In some embodiments, the GMR of 56 days to baseline titers for hPIV3 in subjects administered two 300 μg doses of the vaccine composition is in the range of 3.5 to 5.5, e.g., 4.76. In some embodiments, the GMR of 196 days to baseline titers for hPIV3 in subjects administered two 75 μg doses of the vaccine composition is in the range of 1 to 3, e.g., 1.87. In some embodiments, the GMR of 196 days to baseline titers for hPIV3 in subjects administered two 150 μg doses of the vaccine composition is in the range of 1 to 3, e.g., 2.33. In some embodiments, the GMR of 196 days to baseline titers for hPIV3 in subjects administered two 300 µg doses of the vaccine composition is in the range of 2.5 to 4.5, e.g., 3.52.

In some embodiments, the geometric mean titer (GMT) of serum neutralizing antibodies to hMPV increases in the subject by at least 2-fold within 30 days relative to baseline. For example, the GMT of serum neutralizing antibodies to hMPV may increase in the subject by at least 3-fold, at least 4-fold, at least 5-fold, at least 6-fold, at least 7-fold, at least 8-fold, at least 9-fold, or at least 10-fold within 30 days relative to baseline. In some embodiments, the GMT of serum neutralizing antibodies to hMPV increases in the subject by 2-fold to 10-fold within 30 days relative to baseline. In some embodiments, the increase in GMT of serum neutralizing antibodies to hMPV follows a single 25 µg dose of the vaccine composition. In other embodiments, the increase in GMT of serum neutralizing antibodies to hMPV follows a single 50 µg dose of the vaccine composition. In yet other embodiments, the increase in GMT of serum neutralizing antibodies to hMPV follows a single 75 µg dose of the vaccine composition. For example, the GMT in serum neutralizing antibodies to hMPV may increase in the subject by at least 2-fold within 30 days relative to baseline, following a single 25 µg dose of the vaccine composition. As another example, the GMT in serum neutralizing antibodies to hMPV may increase in the subject by at least 2-fold within 30 days relative to baseline, following a single 75 µg dose. As yet another example, the GMT in serum neutralizing antibodies to hMPV may increase in the subject by at least 6-fold within 30 days relative to baseline, following a single 25 µg dose of the vaccine composition. As still another example, the GMT in serum neutralizing antibodies to hMPV may increase in the subject by at least 6-fold within 30 days relative to baseline, following a single 75 µg dose.

In some embodiments, the geometric mean titer (GMT) of serum neutralizing antibodies to hPIV3 increases in the subject by at least 2-fold within 30 days relative to baseline. For example, the GMT of serum neutralizing antibodies to hPIV3 may increase in the subject by at least 3-fold, at least 4-fold, at least 5-fold, at least 6-fold, at least 7-fold, at least 8-fold, at least 9-fold, or at least 10-fold within 30 days relative to baseline. In some embodiments, the GMT of serum neutralizing antibodies to hPIV3 increases in the subject by 2-fold to 10-fold within 30 days relative to baseline. In some embodiments, the increase in GMT of serum neutralizing antibodies to hPIV3 follows a single 25 µg dose of the vaccine composition. In other embodiments, the increase in GMT of serum neutralizing antibodies to hPIV3 follows a single 50 µg dose of the vaccine composition. In yet other embodiments, the increase in GMT of serum neutralizing antibodies to hPIV3 follows a single 75 µg dose of the vaccine composition. For example, the GMT in serum neutralizing antibodies to hPIV3 may increase in the subject by at least 2-fold within 30 days relative to baseline, following a single 25 µg dose of the vaccine composition. As another example, the GMT in serum neutralizing antibodies to hPIV3 may increase in the subject by at least 2-fold within 30 days relative to baseline, following a single 75 µg dose. As yet another example, the GMT in serum neutralizing antibodies to hPIV3 may increase in the subject by at least 3-fold within 30 days relative to baseline, following a single 25 µg dose of the vaccine composition. As still another example, the GMT in serum neutralizing antibodies to hPIV3 may increase in the subject by at least 3-fold within 30 days relative to baseline, following a single 75 µg dose.

A control, in some embodiments, is the anti-hMPV/hPIV3 antigen antibody titer produced in a subject who has not been administered the hMPV/hPIV3 mRNA vaccine. In some embodiments, a control is an anti-hMPV/hPIV3 antigen antibody titer produced in a subject administered a recombinant or purified hMPV/hPIV3protein vaccine. Recombinant protein vaccines typically include protein antigens that either have been produced in a heterologous expression system (e.g., bacteria or yeast) or purified from large amounts of the pathogenic organism.

In some embodiments, the ability of the hMPV/hPIV3 mRNA vaccine to be effective is measured in a murine model. For example, the hMPV/hPIV3 mRNA vaccine may be administered to a murine model and the murine model assayed for induction of neutralizing antibody titers. Viral challenge studies may also be used to assess the efficacy of a vaccine of the present disclosure. For example, the hMPV/hPIV3 mRNA vaccine may be administered to a murine model, the murine model challenged with hMPV/hPIV3, and the murine model assayed for survival and/or immune response (e.g., neutralizing antibody response, T cell response (e.g., cytokine response)).

In some embodiments, an effective amount of the hMPV/hPIV3 mRNA vaccine is a dose that is reduced compared to the standard of care dose of a recombinant hMPV/hPIV3protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hMPV/hPIV3protein vaccine, or a live attenuated or inactivated hMPV/hPIV3vaccine, or a hMPV/hPIV3VLP vaccine, that a physician/clinician or other medical professional would administer to a subject to treat or prevent hMPV/hPIV3, or a hMPV/hPIV3-related condition, while following the standard of care guideline for treating or preventing hMPV/hPIV3, or a hMPV/hPIV3-related condition.

In some embodiments, the anti-hMPV/hPIV3 antigen antibody titer produced in a subject administered an effective amount of the hMPV/hPIV3 mRNA vaccine is equivalent to an anti-hMPV/hPIV3 antigen antibody titer produced in a control subject administered a standard of care dose of a recombinant or purified hMPV/hPIV3 protein vaccine, or a live attenuated or inactivated hMPV/hPIV3 vaccine, or a hMPV/hPIV3 VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy} = (ARU - ARV)/ARU \times 100; \text{ and}$$

$$\text{Efficacy} = (1 - RR) \times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, efficacy of the hMPV/hPIV3 mRNA vaccine is at least 60% relative to unvaccinated control subjects. For example, efficacy of the hMPV/hPIV3 mRNA vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a the hMPV/hPIV3 mRNA vaccine of the present disclosure is sufficient to provide sterilizing immunity in the subject for at least 1 year. For example, the effective amount of the hMPV/hPIV3 mRNA vaccine of the present disclosure is sufficient to provide sterilizing immunity in the subject for at least 2 years, at least 3 years, at least 4 years, or at least 5 years. In some embodiments, the effective amount of the hMPV/hPIV3 mRNA vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of the hMPV/hPIV3 mRNA vaccine of the present disclosure is sufficient to produce detectable levels of hMPV/hPIV3 antigen as measured in serum of the subject at 1-72 hours post administration.

Titer. An antibody titer is a measurement of the amount of antibodies within a subject, for example, antibodies that are specific to a particular antigen (e.g., an anti-hMPV/hPIV3 antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of the hMPV/hPIV3 mRNA vaccine of the present disclosure is sufficient to produce a 1,000-10,000 neutralizing antibody titer produced by neutralizing antibody against the hMPV/hPIV3 antigen as measured in serum of the subject at 1-72 hours post administration. In some embodiments, the effective amount is sufficient to produce a 1,000-5,000 neutralizing antibody titer produced by neutralizing antibody against the hMPV/hPIV3 antigen as measured in serum of the subject at 1-72 hours post administration. In some embodiments, the effective amount is sufficient to produce a 5,000-10,000 neutralizing antibody titer produced by neutralizing antibody against the hMPV/hPIV3 antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-hMPV/hPIV3 antigen antibody titer produced in the subject is increased by at least 1 log relative to a control. For example, an anti-hMPV/hPIV3 antigen antibody titer produced in the subject may be increased by at least 2, 3, 4, 5, 6, 7, 8, 9 or 10 log relative to a control.

In some embodiments, an anti-hMPV/hPIV3 antigen antibody titer produced in the subject is increased at least 2 times relative to a control. For example, an anti-hMPV/hPIV3 antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated hMPV/hPIV3 vaccine, an inactivated hMPV/hPIV3 vaccine, or a protein subunit hMPV/hPIV3 vaccine.

EXAMPLES

Example 1. A Phase 1, Randomized, Observer-Blind, Placebo-Controlled, Dose-Ranging Study to Evaluate the Safety, Reactogenicity, and Immunogenicity of the mRNA hMPV/hPIV3 Vaccine, a Combined Human Metapneumovirus (hMPV) and Human Parainfluenza Virus Type 3 (hPIV3) Vaccine, when Administered to Healthy Adults This was a Phase 1, first-in-human (FIH), randomized, observer-blind, placebo-controlled, dose-ranging study to evaluate the safety, reactogenicity, and immunogenicity of a the combined hMPV and hPIV3 mRNA vaccine provided herein, administered intramuscularly (IM) according to a 1-dose versus 2-dose schedule in healthy adults (18 through 49 years of age).

Study Overview

Study Design

The study was conducted in 2 phases, the dose-escalation phase and the dose-selection phase. All subjects are followed up for 1 year after the last vaccination.

Figure 2:
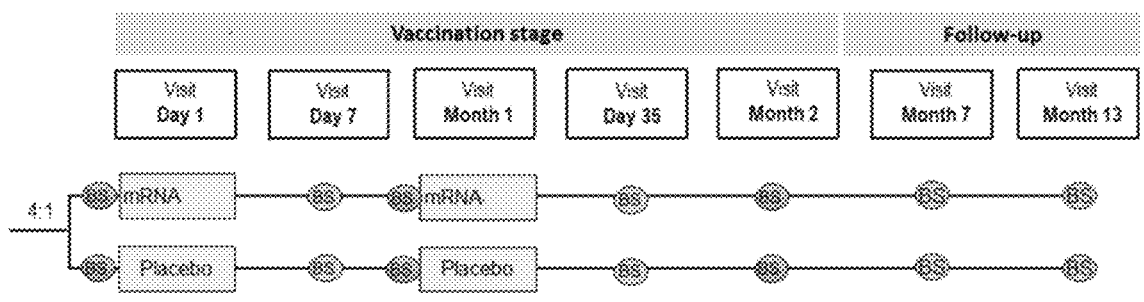

In the dose-escalation phase (FIGS. 1 and 2), there was sequential enrollment of 5 subjects at each dose level (N=20), randomized in a 4:1 ratio to receive either the hMPV/hPIV3 mRNA vaccine or placebo. Dose levels were 25, 75, 150, and 300 μg. Subjects were administered two doses, at Day 1 and Month 1 (Day 28). Following Safety Monitoring Committee (SMC) review of all safety and reactogenicity data up to Day 35 of the dose-escalation phase, the 3 highest dose levels (75, 150, and 300 µg) were selected to be evaluated in the dose-selection phase of the study.

Figure 3:
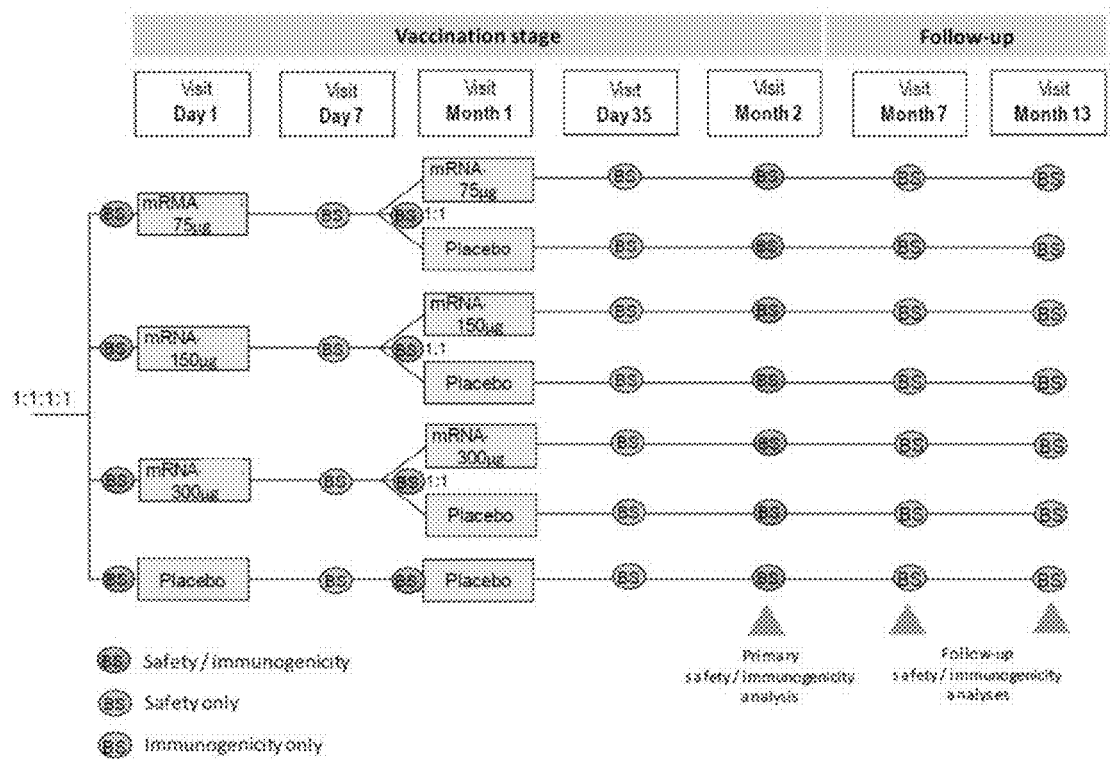

In the dose-selection phase (FIGS. 1 and 3), subjects were randomly assigned into one of 4 dose groups (75 µg hMPV/hPIV3 mRNA vaccine, 150 µg hMPV/hPIV3 mRNA vaccine, 300 µg hMPV/hPIV3 mRNA vaccine, or placebo) in a 1:1:1:1 ratio, each cohort consisting of 26 subjects. Within each hMPV/hPIV3 mRNA vaccine dose level group, subjects were randomly assigned in a 1:1 ratio to receive the second dose of hMPV/hPIV3 mRNA vaccine or placebo at Month 1 (Day 28).

Objectives and Endpoints
Primary Objectives

1. To evaluate the safety and reactogenicity of the hMPV/hPIV3 mRNA vaccine, administered according to a 1-dose versus 2-dose schedule, through 28 days after the last vaccination.
2. To evaluate the humoral immunogenicity of the hMPV/hPIV3 mRNA vaccine, administered according to a 1-dose versus 2-dose schedule, through 28 days after the last vaccination.
3. To select the optimal dose and vaccination schedule of the hMPV/hPIV3 mRNA vaccine for further clinical development.

Primary Safety Endpoints

1. Occurrence of each solicited local and systemic adverse events (AE), during a 7-day follow-up period after each and any vaccination (i.e., the day of vaccination and 6 subsequent days).
2. Occurrence of any unsolicited adverse events (AEs), serious adverse events (SAEs), and adverse event of special interest (AESIs) that are considered related to the hMPV/hPIV3 mRNA vaccine during the entire study period (Day 1 through Month 13).
3. Occurrence of any laboratory abnormality at Day 1, Day 7, Month 1, Day 35, and Month 2.
4. Occurrence of any unsolicited AE, during a 28-day follow-up period after each study vaccination (the day of vaccination and 27 subsequent days). 5. Occurrence of any medically-attended AEs from Day 1 to Month 2.
6. Occurrence of any AESIs from Day 1 to Month 2.
7. Occurrence of any SAEs from Day 1 to Month 2.

Primary Immunogenicity Endpoints

1. Geometric mean titer (GMT) of the serum anti-hMPV and anti-PIV3 neutralizing antibodies at Day 1 (baseline), Month 1, and Month 2.
2. Proportion of subjects with a ≥4-fold increase in serum anti-hMPV and anti-PIV3 neutralizing antibody titer from Day 1 to Month 1 and Month 2.
3. Proportion of subjects at Month 1 and Month 2 who achieve serum anti-hMPV and anti-PIV3 neutralizing antibody titers greater than the third quartile of the serum anti-hMPV and anti-PIV3 antibody titers overall distribution at Day 1.
4. Reverse cumulative distribution of serum anti-hMPV and anti-PIV3 neutralizing antibody titers at Day 1, Month 1, and Month 2.

Analyses

1. A 2-month interim analysis of safety, reactogenicity, and immunogenicity data collected from Visit Day 1 to Visit Month 2 and associated endpoints was conducted on cleaned data and reported on a treatment group level. This was a partially unblinded analysis in that access to individual listings was restricted to pre-identified Sponsor study team members. Study sites remained blinded.
2. A 7-month interim analysis of immunogenicity data collected from Visit Day 1 to Visit Month 7 was conducted on cleaned data and was reported on a treatment group level. This was a partially unblinded analysis in that access to individual listings was restricted to pre-identified Sponsor study team members. Study sites remained blinded. This analysis provided information about short-term antibody persistence.
3. The final analysis of safety and immunogenicity data collected from Visit Day 1 through the end of the study was performed as soon as the study database is cleaned and locked.

Results
Demographics

Demographic and baseline characteristics were generally balanced across treatment groups (Table 1). There were more females than males enrolled across the treatment groups, except for the 300 µg 2-dose group, and body mass index was higher in this group. Age was somewhat lower in the 25 µg group, and there were more subjects of white race in the 75 µg 2-dose and 300 µg 1-dose groups.

TABLE 1

Study Demographics

| | | hMPV/hPIV3 mRNA vaccine | | | | | | | | |
|---|---|---|---|---|---|---|---|---|---|---|
| | | 25 µg | 75 µg | | 150 µg | | 300 µg | | Total | Total |
| | Placebo (N = 30) | 2-Dose (N = 4) | 1-Dose (N = 13) | 2-Dose (N = 17) | 1-Dose (N = 13) | 2-Dose (N = 17) | 1-Dose (N = 13) | 2-Dose (N = 17) | Total (N = 94) | Total (N = 124) |
| Age (years) | | | | | | | | | | |
| Mean | 39.7 | 28.0 | 36.4 | 39.6 | 34.3 | 35.6 | 34.9 | 35.1 | 35.7 | 36.7 |
| (SD) | (7.67) | (9.38) | (6.21) | (6.85) | (9.10) | (7.98) | (8.34) | (9.47) | (8.23) | (8.25) |
| Min, Max | 19, 48 | 20, 38 | 25, 45 | 29, 49 | 20, 47 | 22, 48 | 19, 47 | 19, 49 | 19, 49 | 19, 49 |
| Gender, n (%) | | | | | | | | | | |
| Male | 12 | 1 | 3 | 4 | 4 | 7 | 4 | 11 | 34 | 46 |
| | (40.0) | (25.0) | (23.1) | (23.5) | (30.8) | (41.2) | (30.8) | (64.7) | (36.2) | (37.1) |
| Female | 18 | 3 | 10 | 13 | 9 | 10 | 9 | 6 | 60 | 78 |
| | (60.0) | (75.0) | (76.9) | (76.5) | (69.2) | (58.8) | (69.2) | (35.3) | (63.8) | (62.9) |
| Race, n (%) | | | | | | | | | | |
| Am. Indian or Alaskan Native | 1 (3.3) | 0 | 0 | 0 | 0 | 0 | 0 | 0 | 0 | 1 (0.8) |

TABLE 1-continued

Study Demographics

| | | hMPV/hPIV3 mRNA vaccine | | | | | | | | |
|---|---|---|---|---|---|---|---|---|---|---|
| | | 25 µg | 75 µg | | 150 µg | | 300 µg | | | |
| | Placebo (N = 30) | 2-Dose (N = 4) | 1-Dose (N = 13) | 2-Dose (N = 17) | 1-Dose (N = 13) | 2-Dose (N = 17) | 1-Dose (N = 13) | 2-Dose (N = 17) | Total (N = 94) | Total (N = 124) |
| Asian | 1 (3.3) | 0 | 0 | 0 | 0 | 0 | 0 | 0 | 0 | 1 (0.8) |
| Black or African American | 8 (26.7) | 2 (50.0) | 6 (46.2) | 3 (17.6) | 5 (38.5) | 6 (35.3) | 2 (15.4) | 8 (47.1) | 32 (34.0) | 40 (32.3) |
| White | 20 (66.7) | 2 (50.0) | 7 (53.8) | 14 (82.4) | 8 (61.5) | 10 (58.8) | 11 (84.6) | 9 (52.9) | 61 (64.9) | 81 (65.3) |
| Multi-racial | 0 | 0 | 0 | 0 | 0 | 1 (5.9) | 0 | 0 | 1 (1.1) | 1 (0.8) |
| | | | | | Ethnicity, n (%) | | | | | |
| Hispanic, Latino, or Spanish | 3 (10.0) | 0 | 3 (23.1) | 1 (5.9) | 2 (15.4) | 1 (5.9) | 2 (15.4) | 2 (11.8) | 11 (11.7) | 14 (11.3) |
| Not Hispanic, Latino, or Spanish | 27 (90.0) | 4 (100.0) | 10 (76.9) | 16 (94.1) | 11 (84.6) | 16 (94.1) | 11 (84.6) | 15 (88.2) | 83 (88.3) | 110 (88.7) |
| | | | | | Weight (kg) | | | | | |
| Mean (SD) | 77.25 (13.885) | 80.60 (13.561) | 74.99 (10.651) | 76.67 (12.703) | 74.49 (15.598) | 78.98 (10.404) | 73.55 (11.881) | 86.17 (16.160) | 78.01 (13.425) | 77.83 (13.485) |
| Min, Max | 52.3, 114.0 | 60.3, 88.5 | 61.6, 103.2 | 51.2, 95.5 | 52.5, 101.2 | 63.2, 94.9 | 53.7, 91.1 | 51.7, 119.0 | 51.2, 119.0 | 51.2, 119.0 |
| | | | | | Height (cm) | | | | | |
| Mean (SD) | 168.81 (8.502) | 175.58 (8.310) | 167.35 (8.055) | 166.45 (9.071) | 168.72 (8.342) | 167.88 (6.282) | 165.29 (9.866) | 173.61 (10.133) | 168.67 (8.951) | 168.70 (8.810) |
| Min, Max | 154.9, 189.0 | 165.1, 185.4 | 152.5, 179.0 | 147.3, 179.0 | 157.0, 182.5 | 156.2, 181.0 | 146.0, 179.0 | 155.0, 190.5 | 146.0, 190.5 | 146.0, 190.5 |
| | | | | | Body mass index (kg/m$^2$) | | | | | |
| Mean (SD) | 27.04 (3.924) | 26.35 (5.480) | 26.81 (3.278) | 27.65 (3.984) | 26.18 (5.173) | 28.07 (3.843) | 26.92 (3.712) | 28.50 (4.341) | 27.40 (4.093) | 27.32 (4.040) |
| Min, Max | 20.4, 34.7 | 19.4, 32.5 | 21.1, 32.6 | 20.5, 34.6 | 18.5, 34.5 | 22.7, 34.8 | 20.6, 35.0 | 20.1, 34.7 | 18.5, 35.0 | 18.5, 35.0 |

Safety

Solicited Events

Solicited adverse events were collected through 7 days after each vaccination (Table 2 and Table 3). Across dose levels, the rate of solicited adverse events generally decreased between the first and second vaccination. Injection site pain was the most common solicited local adverse event, with rates of 10-100% across treatment groups, which did not increase with dose level.

Solicited Adverse Events by Grade and Treatment Group - First Vaccination
(First Vaccination Solicited Safety Set)

| | | hMPV/hPIV3 mRNA vaccine | | | | | | | |
|---|---|---|---|---|---|---|---|---|---|
| | | 25 µg | 75 µg | | 150 µg | | 300 µg | | |
| | Placebo (N = 30) n (%) | 2-Dose (N = 4) n (%) | 1-Dose (N = 13) n (%) | 2-Dose (N = 17) n (%) | 1-Dose (N = 13) n (%) | 2-Dose (N = 17) n (%) | 1-Dose (N = 13) n (%) | 2-Dose (N = 17) n (%) | Total (N = 94) n (%) |
| | | | | Solicited Local AEs | | | | | |
| Pain-N1 | 28 | 4 | 13 | 17 | 13 | 17 | 13 | 17 | 94 |
| Any | 3 (10.7) | 3 (75.0) | 12 (92.3) | 14 (82.4) | 10 (76.9) | 15 (88.2) | 13 (100.0) | 13 (76.5) | 80 (85.1) |
| Grade 1 | 2 (7.1) | 1 (25.0) | 8 (61.5) | 6 (35.3) | 3 (23.1) | 7 (41.2) | 2 (15.4) | 6 (35.3) | 33 (35.1) |
| Grade 2 | 1 (3.6) | 2 (50.0) | 2 (15.4) | 7 (41.2) | 5 (38.5) | 7 (41.2) | 7 (53.8) | 5 (29.4) | 35 (37.2) |
| Grade 3 | 0 | 0 | 2 (15.4) | 1 (5.9) | 2 (15.4) | 1 (5.9) | 4 (30.8) | 2 (11.8) | 12 (12.8) |
| Erythema (Redness)-N1 | 27 | 4 | 11 | 15 | 11 | 15 | 12 | 16 | 84 |

-continued

Solicited Adverse Events by Grade and Treatment Group - First Vaccination
(First Vaccination Solicited Safety Set)

|  | Placebo (N = 30) n (%) | hMPV/hPIV3 mRNA vaccine | | | | | | | Total (N = 94) n (%) |
|---|---|---|---|---|---|---|---|---|---|
|  | | 25 µg 2-Dose (N = 4) n (%) | 75 µg 1-Dose (N = 13) n (%) | 2-Dose (N = 17) n (%) | 150 µg 1-Dose (N = 13) n (%) | 2-Dose (N = 17) n (%) | 300 µg 1-Dose (N = 13) n (%) | 2-Dose (N = 17) n (%) | |
| Any | 0 | 0 | 0 | 2 (13.3) | 0 | 0 | 0 | 1 (6.3) | 3 (3.6) |
| Grade 1 | 0 | 0 | 0 | 1 (6.7) | 0 | 0 | 0 | 1 (6.3) | 2 (2.4) |
| Grade 2 | 0 | 0 | 0 | 0 | 0 | 0 | 0 | 0 | 0 |
| Grade 3 | 0 | 0 | 0 | 1 (6.7) | 0 | 0 | 0 | 0 | 1 (1.2) |
| Swelling (Hardness)-N1 | 26 | 4 | 11 | 16 | 11 | 15 | 12 | 16 | 85 |
| Any | 0 | 0 | 0 | 3 (18.8) | 1 (9.1) | 0 | 2 (16.7) | 2 (12.5) | 8 (9.4) |
| Grade 1 | 0 | 0 | 0 | 2 (12.5) | 1 (9.1) | 0 | 0 | 1 (6.3) | 4 (4.7) |
| Grade 2 | 0 | 0 | 0 | 0 | 0 | 0 | 1 (8.3) | 1 (6.3) | 2 (2.4) |
| Grade 3 | 0 | 0 | 0 | 1 (6.3) | 0 | 0 | 1 (8.3) | 0 | 2 (2.4) |
| Solicited Systemic AEs | | | | | | | | | |
| Fever-N1 | 30 | 4 | 13 | 17 | 13 | 17 | 13 | 17 | 94 |
| Any | 0 | 0 | 1 (7.7) | 1 (5.9) | 4 (30.8) | 0 | 4 (30.8) | 4 (23.5) | 14 (14.9) |
| Grade 1 | 0 | 0 | 0 | 0 | 0 | 0 | 1 (7.7) | 0 | 1 (1.1) |
| Grade 2 | 0 | 0 | 0 | 1 (5.9) | 3 (23.1) | 0 | 3 (23.1) | 4 (23.5) | 11 (11.7) |
| Grade 3 | 0 | 0 | 1 (7.7) | 0 | 1 (7.7) | 0 | 0 | 0 | 2 (2.1) |
| Headache-N1 | 27 | 4 | 13 | 17 | 12 | 17 | 13 | 17 | 93 |
| Any | 3 (11.1) | 1 (25.0) | 6 (46.2) | 5 (29.4) | 7 (58.3) | 8 (47.1) | 11 (84.6) | 10 (58.8) | 48 (51.6) |
| Grade 1 | 3 (11.1) | 1 (25.0) | 5 (38.5) | 1 (5.9) | 6 (50.0) | 5 (29.4) | 7 (53.8) | 6 (35.3) | 31 (33.3) |
| Grade 2 | 0 | 0 | 0 | 4 (23.5) | 1 (8.3) | 1 (5.9) | 2 (15.4) | 4 (23.5) | 12 (12.9) |
| Grade 3 | 0 | 0 | 1 (7.7) | 0 | 0 | 2 (11.8) | 2 (15.4) | 0 | 5 (5.4) |
| Fatigue-N1 | 27 | 4 | 13 | 17 | 11 | 17 | 13 | 17 | 92 |
| Any | 4 (14.8) | 1 (25.0) | 3 (23.1) | 5 (29.4) | 8 (72.7) | 6 (35.3) | 10 (76.9) | 11 (64.7) | 44 (47.8) |
| Grade 1 | 4 (14.8) | 1 (25.0) | 1 (7.7) | 2 (11.8) | 6 (54.5) | 1 (5.9) | 3 (23.1) | 7 (41.2) | 21 (22.8) |
| Grade 2 | 0 | 0 | 1 (7.7) | 2 (11.8) | 1 (9.1) | 4 (23.5) | 5 (38.5) | 4 (23.5) | 17 (18.5) |
| Grade 3 | 0 | 0 | 1 (7.7) | 1 (5.9) | 1 (9.1) | 1 (5.9) | 2 (15.4) | 0 | 6 (6.5) |
| Myalgia-N1 | 27 | 4 | 13 | 17 | 11 | 17 | 13 | 17 | 92 |
| Any | 2 (7.4) | 1 (25.0) | 4 (30.8) | 2 (11.8) | 7 (63.6) | 5 (29.4) | 9 (69.2) | 11 (64.7) | 39 (42.4) |
| Grade 1 | 2 (7.4) | 0 | 3 (23.1) | 0 | 4 (36.4) | 2 (11.8) | 3 (23.1) | 4 (23.5) | 16 (17.4) |
| Grade 2 | 0 | 1 (25.0) | 0 | 1 (5.9) | 2 (18.2) | 1 (5.9) | 5 (38.5) | 6 (35.3) | 16 (17.4) |
| Grade 3 | 0 | 0 | 1 (7.7) | 1 (5.9) | 1 (9.1) | 2 (11.8) | 1 (7.7) | 1 (5.9) | 7 (7.6) |
| Arthralgia-N1 | 27 | 4 | 13 | 17 | 11 | 17 | 13 | 17 | 92 |
| Any | 2 (7.4) | 1 (25.0) | 2 (15.4) | 5 (29.4) | 4 (36.4) | 4 (23.5) | 8 (61.5) | 6 (35.3) | 30 (32.6) |
| Grade 1 | 2 (7.4) | 1 (25.0) | 0 | 2 (11.8) | 2 (18.2) | 2 (11.8) | 3 (23.1) | 3 (17.6) | 13 (14.1) |
| Grade 2 | 0 | 0 | 2 (15.4) | 2 (11.8) | 2 (18.2) | 1 (5.9) | 3 (23.1) | 3 (17.6) | 13 (14.1) |
| Grade 3 | 0 | 0 | 0 | 1 (5.9) | 0 | 1 (5.9) | 2 (15.4) | 0 | 4 (4.3) |
| Nausea-N1 | 27 | 4 | 13 | 17 | 11 | 17 | 13 | 17 | 92 |
| Any | 0 | 0 | 3 (23.1) | 3 (17.6) | 4 (36.4) | 3 (17.6) | 4 (30.8) | 4 (23.5) | 21 (22.8) |
| Grade 1 | 0 | 0 | 2 (15.4) | 1 (5.9) | 2 (18.2) | 1 (5.9) | 4 (30.8) | 4 (23.5) | 14 (15.2) |
| Grade 2 | 0 | 0 | 0 | 2 (11.8) | 2 (18.2) | 1 (5.9) | 0 | 0 | 5 (5.4) |
| Grade 3 | 0 | 0 | 1 (7.7) | 0 | 0 | 1 (5.9) | 0 | 0 | 2 (2.2) |

TABLE 3

Solicited Adverse Events by Grade and Treatment Group - Second Vaccination
(Second Vaccination Solicited Safety Set)

|  | Placebo (N = 28) n (%) | hMPV/hPIV3 mRNA vaccine | | | | | | | Total (N = 91) n (%) |
|---|---|---|---|---|---|---|---|---|---|
|  | | 25 µg 2-Dose (N = 4) n (%) | 75 µg 1-Dose (N = 12) n (%) | 2-Dose (N = 17) n (%) | 150 µg 1-Dose (N = 13) n (%) | 2-Dose (N = 17) n (%) | 300 µg 1-Dose (N = 11) n (%) | 2-Dose (N = 17) n (%) | |
| Solicited Local AEs | | | | | | | | | |
| Pain-N1 | 27 | 4 | 12 | 17 | 13 | 17 | 10 | 17 | 90 |
| Any | 4 (14.8) | 2 (50.0) | 2 (16.7) | 12 (70.6) | 4 (30.8) | 12 (70.6) | 1 (10.0) | 13 (76.5) | 46 (51.1) |
| Grade 1 | 3 (11.1) | 0 | 2 (16.7) | 6 (35.3) | 2 (15.4) | 7 (41.2) | 1 (10.0) | 7 (41.2) | 25 (27.8) |
| Grade 2 | 1 (3.7) | 2 (50.0) | 0 | 5 (29.4) | 2 (15.4) | 4 (23.5) | 0 | 5 (29.4) | 18 (20.0) |
| Grade 3 | 0 | 0 | 0 | 1 (5.9) | 0 | 1 (5.9) | 0 | 1 (5.9) | 3 (3.3) |
| Erythema (Redness)-N1 | 26 | 4 | 12 | 15 | 13 | 17 | 9 | 17 | 87 |
| Any | 1 (3.8) | 0 | 0 | 1 (6.7) | 0 | 1 (5.9) | 0 | 1 (5.9) | 3 (3.4) |
| Grade 1 | 0 | 0 | 0 | 1 (6.7) | 0 | 0 | 0 | 1 (5.9) | 2 (2.3) |

TABLE 3-continued

Solicited Adverse Events by Grade and Treatment Group - Second Vaccination
(Second Vaccination Solicited Safety Set)

| | | hMPV/hPIV3 mRNA vaccine | | | | | | | |
|---|---|---|---|---|---|---|---|---|---|
| | | 25 µg | | 75 µg | | 150 µg | | 300 µg | |
| | Placebo (N = 28) n (%) | 2-Dose (N = 4) n (%) | 1-Dose (N = 12) n (%) | 2-Dose (N = 17) n (%) | 1-Dose (N = 13) n (%) | 2-Dose (N = 17) n (%) | 1-Dose (N = 11) n (%) | 2-Dose (N = 17) n (%) | Total (N = 91) n (%) |
| Grade 2 | 0 | 0 | 0 | 0 | 0 | 1 (5.9) | 0 | 0 | 1 (1.1) |
| Grade 3 | 1 (3.8) | 0 | 0 | 0 | 0 | 0 | 0 | 0 | 0 |
| Swelling (Hardness)-N1 | 26 | 4 | 12 | 15 | 13 | 17 | 9 | 17 | 87 |
| Any | 0 | 0 | 0 | 2 (13.3) | 0 | 2 (11.8) | 0 | 1 (5.9) | 5 (5.7) |
| Grade 1 | 0 | 0 | 0 | 2 (13.3) | 0 | 2 (11.8) | 0 | 1 (5.9) | 5 (5.7) |
| Grade 2 | 0 | 0 | 0 | 0 | 0 | 0 | 0 | 0 | 0 |
| Grade 3 | 0 | 0 | 0 | 0 | 0 | 0 | 0 | 0 | 0 |
| Solicited Systemic AEs | | | | | | | | | |
| Fever-N1 | 28 | 4 | 12 | 17 | 13 | 17 | 11 | 17 | 91 |
| Any | 0 | 0 | 0 | 0 | 0 | 1 (5.9) | 0 | 2 (11.8) | 3 (3.3) |
| Grade 1 | 0 | 0 | 0 | 0 | 0 | 1 (5.9) | 0 | 0 | 1 (1.1) |
| Grade 2 | 0 | 0 | 0 | 0 | 0 | 0 | 0 | 1 (5.9) | 1 (1.1) |
| Grade 3 | 0 | 0 | 0 | 0 | 0 | 0 | 0 | 1 (5.9) | 1 (1.1) |
| Headache-N1 | 27 | 4 | 12 | 17 | 13 | 17 | 10 | 17 | 90 |
| Any | 2 (7.4) | 1 (25.0) | 1 (8.3) | 5 (29.4) | 4 (30.8) | 9 (52.9) | 1 (10.0) | 8 (47.1) | 29 (32.2) |
| Grade 1 | 1 (3.7) | 1 (25.0) | 1 (8.3) | 3 (17.6) | 4 (30.8) | 7 (41.2) | 0 | 5 (29.4) | 21 (23.3) |
| Grade 2 | 1 (3.7) | 0 | 0 | 2 (11.8) | 0 | 0 | 1 (10.0) | 3 (17.6) | 6 (6.7) |
| Grade 3 | 0 | 0 | 0 | 0 | 0 | 2 (11.8) | 0 | 0 | 2 (2.2) |
| Fatigue-N1 | 27 | 4 | 12 | 17 | 13 | 17 | 10 | 17 | 90 |
| Any | 2 (7.4) | 0 | 0 | 4 (23.5) | 4 (30.8) | 7 (41.2) | 3 (30.0) | 9 (52.9) | 27 (30.0) |
| Grade 1 | 1 (3.7) | 0 | 0 | 2 (11.8) | 2 (15.4) | 5 (29.4) | 2 (20.0) | 5 (29.4) | 16 (17.8) |
| Grade 2 | 1 (3.7) | 0 | 0 | 1 (5.9) | 2 (15.4) | 1 (5.9) | 1 (10.0) | 4 (23.5) | 9 (10.0) |
| Grade 3 | 0 | 0 | 0 | 1 (5.9) | 0 | 1 (5.9) | 0 | 0 | 2 (2.2) |
| Myalgia-N1 | 27 | 4 | 12 | 17 | 13 | 17 | 10 | 17 | 90 |
| Any | 2 (7.4) | 1 (25.0) | 1 (8.3) | 6 (35.3) | 2 (15.4) | 7 (41.2) | 1 (10.0) | 10 (58.8) | 28 (31.1) |
| Grade 1 | 2 (7.4) | 0 | 1 (8.3) | 4 (23.5) | 1 (7.7) | 4 (23.5) | 1 (10.0) | 5 (29.4) | 16 (17.8) |
| Grade 2 | 0 | 1 (25.0) | 0 | 1 (5.9) | 1 (7.7) | 2 (11.8) | 0 | 5 (29.4) | 10 (11.1) |
| Grade 3 | 0 | 0 | 0 | 1 (5.9) | 0 | 1 (5.9) | 0 | 0 | 2 (2.2) |
| Arthralgia-N1 | 27 | 4 | 12 | 17 | 13 | 17 | 10 | 17 | 90 |
| Any | 0 | 1 (25.0) | 1 (8.3) | 4 (23.5) | 2 (15.4) | 4 (23.5) | 1 (10.0) | 8 (47.1) | 21 (23.3) |
| Grade 1 | 0 | 0 | 1 (8.3) | 2 (11.8) | 2 (15.4) | 2 (11.8) | 1 (10.0) | 5 (29.4) | 13 (14.4) |
| Grade 2 | 0 | 1 (25.0) | 0 | 2 (11.8) | 0 | 1 (5.9) | 0 | 3 (17.6) | 7 (7.8) |
| Grade 3 | 0 | 0 | 0 | 0 | 0 | 1 (5.9) | 0 | 0 | 1 (1.1) |
| Nausea-N1 | 27 | 4 | 12 | 17 | 13 | 17 | 10 | 17 | 90 |
| Any | 1 (3.7) | 0 | 0 | 4 (23.5) | 0 | 4 (23.5) | 1 (10.0) | 5 (29.4) | 14 (15.6) |
| Grade 1 | 1 (3.7) | 0 | 0 | 4 (23.5) | 0 | 3 (17.6) | 1 (10.0) | 4 (23.5) | 12 (13.3) |
| Grade 2 | 0 | 0 | 0 | 0 | 0 | 1 (5.9) | 0 | 1 (5.9) | 2 (2.2) |
| Grade 3 | 0 | 0 | 0 | 0 | 0 | 0 | 0 | 0 | 0 |

Unsolicited Events

Unsolicited events were collected through 28 days after each vaccination (Table 4 and Table 5). For subjects in the treatment groups, the most common unsolicited AEs overall were upper respiratory tract infection, chills, and headache, which were reported by 5 (5.3%) subjects each.

No SAEs, AEs of special interest, or AEs leading to withdrawal were reported.

There was no pattern of clinically relevant lab abnormalities or changes from baseline lab values across vaccine treatment groups.

TABLE 4

Solicited Adverse Events by Grade and Treatment Group - First Vaccination
(First Vaccination Solicited Safety Set)

| | | hMPV/hPIV3 mRNA vaccine | | | | | | | |
|---|---|---|---|---|---|---|---|---|---|
| | | 25 µg | | 75 µg | | 150 µg | | 300 µg | |
| | Placebo (N = 30) n (%) | 2-Dose (N = 4) n (%) | 1-Dose (N = 13) n (%) | 2-Dose (N = 17) n (%) | 1-Dose (N = 13) n (%) | 2-Dose (N = 17) n (%) | 1-Dose (N = 13) n (%) | 2-Dose (N = 17) n (%) | Total (N = 94) n (%) |
| Solicited Local AEs | | | | | | | | | |
| Pain-N1 | 28 | 4 | 13 | 17 | 13 | 17 | 13 | 17 | 94 |
| Any | 3 (10.7) | 3 (75.0) | 12 (92.3) | 14 (82.4) | 10 (76.9) | 15 (88.2) | 13 (100.0) | 13 (76.5) | 80 (85.1) |

TABLE 4-continued

Solicited Adverse Events by Grade and Treatment Group - First Vaccination
(First Vaccination Solicited Safety Set)

| | | | hMPV/hPIV3 mRNA vaccine | | | | | | |
|---|---|---|---|---|---|---|---|---|---|
| | | 25 µg | 75 µg | | 150 µg | | 300 µg | | |
| | Placebo (N = 30) n (%) | 2-Dose (N = 4) n (%) | 1-Dose (N = 13) n (%) | 2-Dose (N = 17) n (%) | 1-Dose (N = 13) n (%) | 2-Dose (N = 17) n (%) | 1-Dose (N = 13) n (%) | 2-Dose (N = 17) n (%) | Total (N = 94) n (%) |
| Grade 1 | 2 (7.1) | 1 (25.0) | 8 (61.5) | 6 (35.3) | 3 (23.1) | 7 (41.2) | 2 (15.4) | 6 (35.3) | 33 (35.1) |
| Grade 2 | 1 (3.6) | 2 (50.0) | 2 (15.4) | 7 (41.2) | 5 (38.5) | 7 (41.2) | 7 (53.8) | 5 (29.4) | 35 (37.2) |
| Grade 3 | 0 | 0 | 2 (15.4) | 1 (5.9) | 2 (15.4) | 1 (5.9) | 4 (30.8) | 2 (11.8) | 12 (12.8) |
| Erythema (Redness)-N1 | 27 | 4 | 11 | 15 | 11 | 15 | 12 | 16 | 84 |
| Any | 0 | 0 | 0 | 2 (13.3) | 0 | 0 | 0 | 1 (6.3) | 3 (3.6) |
| Grade 1 | 0 | 0 | 0 | 1 (6.7) | 0 | 0 | 0 | 1 (6.3) | 2 (2.4) |
| Grade 2 | 0 | 0 | 0 | 0 | 0 | 0 | 0 | 0 | 0 |
| Grade 3 | 0 | 0 | 0 | 1 (6.7) | 0 | 0 | 0 | 0 | 1 (1.2) |
| Swelling (Hardness)-N1 | 26 | 4 | 11 | 16 | 11 | 15 | 12 | 16 | 85 |
| Any | 0 | 0 | 0 | 3 (18.8) | 1 (9.1) | 0 | 2 (16.7) | 2 (12.5) | 8 (9.4) |
| Grade 1 | 0 | 0 | 0 | 2 (12.5) | 1 (9.1) | 0 | 0 | 1 (6.3) | 4 (4.7) |
| Grade 2 | 0 | 0 | 0 | 0 | 0 | 0 | 1 (8.3) | 1 (6.3) | 2 (2.4) |
| Grade 3 | 0 | 0 | 0 | 1 (6.3) | 0 | 0 | 1 (8.3) | 0 | 2 (2.4) |
| | | | | Solicited Systemic AEs | | | | | |
| Fever-N1 | 30 | 4 | 13 | 17 | 13 | 17 | 13 | 17 | 94 |
| Any | 0 | 0 | 1 (7.7) | 1 (5.9) | 4 (30.8) | 0 | 4 (30.8) | 4 (23.5) | 14 (14.9) |
| Grade 1 | 0 | 0 | 0 | 0 | 0 | 0 | 1 (7.7) | 0 | 1 (1.1) |
| Grade 2 | 0 | 0 | 0 | 1 (5.9) | 3 (23.1) | 0 | 3 (23.1) | 4 (23.5) | 11 (11.7) |
| Grade 3 | 0 | 0 | 1 (7.7) | 0 | 1 (7.7) | 0 | 0 | 0 | 2 (2.1) |
| Headache-N1 | 27 | 4 | 13 | 17 | 12 | 17 | 13 | 17 | 93 |
| Any | 3 (11.1) | 1 (25.0) | 6 (46.2) | 5 (29.4) | 7 (58.3) | 8 (47.1) | 11 (84.6) | 10 (58.8) | 48 (51.6) |
| Grade 1 | 3 (11.1) | 1 (25.0) | 5 (38.5) | 1 (5.9) | 6 (50.0) | 5 (29.4) | 7 (53.8) | 6 (35.3) | 31 (33.3) |
| Grade 2 | 0 | 0 | 0 | 4 (23.5) | 1 (8.3) | 1 (5.9) | 2 (15.4) | 4 (23.5) | 12 (12.9) |
| Grade 3 | 0 | 0 | 1 (7.7) | 0 | 0 | 2 (11.8) | 2 (15.4) | 0 | 5 (5.4) |
| Fatigue-N1 | 27 | 4 | 13 | 17 | 11 | 17 | 13 | 17 | 92 |
| Any | 4 (14.8) | 1 (25.0) | 3 (23.1) | 5 (29.4) | 8 (72.7) | 6 (35.3) | 10 (76.9) | 11 (64.7) | 44 (47.8) |
| Grade 1 | 4 (14.8) | 1 (25.0) | 1 (7.7) | 2 (11.8) | 6 (54.5) | 1 (5.9) | 3 (23.1) | 7 (41.2) | 21 (22.8) |
| Grade 2 | 0 | 0 | 1 (7.7) | 2 (11.8) | 1 (9.1) | 4 (23.5) | 5 (38.5) | 4 (23.5) | 17 (18.5) |
| Grade 3 | 0 | 0 | 1 (7.7) | 1 (5.9) | 1 (9.1) | 1 (5.9) | 2 (15.4) | 0 | 6 (6.5) |
| Myalgia-N1 | 27 | 4 | 13 | 17 | 11 | 17 | 13 | 17 | 92 |
| Any | 2 (7.4) | 1 (25.0) | 4 (30.8) | 2 (11.8) | 7 (63.6) | 5 (29.4) | 9 (69.2) | 11 (64.7) | 39 (42.4) |
| Grade 1 | 2 (7.4) | 0 | 3 (23.1) | 0 | 4 (36.4) | 2 (11.8) | 3 (23.1) | 4 (23.5) | 16 (17.4) |
| Grade 2 | 0 | 1 (25.0) | 0 | 1 (5.9) | 2 (18.2) | 1 (5.9) | 5 (38.5) | 6 (35.3) | 16 (17.4) |
| Grade 3 | 0 | 0 | 1 (7.7) | 1 (5.9) | 1 (9.1) | 2 (11.8) | 1 (7.7) | 1 (5.9) | 7 (7.6) |
| Arthralgia-N1 | 27 | 4 | 13 | 17 | 11 | 17 | 13 | 17 | 92 |
| Any | 2 (7.4) | 1 (25.0) | 2 (15.4) | 5 (29.4) | 4 (36.4) | 4 (23.5) | 8 (61.5) | 6 (35.3) | 30 (32.6) |
| Grade 1 | 2 (7.4) | 1 (25.0) | 0 | 2 (11.8) | 2 (18.2) | 2 (11.8) | 3 (23.1) | 3 (17.6) | 13 (14.1) |
| Grade 2 | 0 | 0 | 2 (15.4) | 2 (11.8) | 2 (18.2) | 1 (5.9) | 3 (23.1) | 3 (17.6) | 13 (14.1) |
| Grade 3 | 0 | 0 | 0 | 1 (5.9) | 0 | 1 (5.9) | 2 (15.4) | 0 | 4 (4.3) |
| Nausea-N1 | 27 | 4 | 13 | 17 | 11 | 17 | 13 | 17 | 92 |
| Any | 0 | 0 | 3 (23.1) | 3 (17.6) | 4 (36.4) | 3 (17.6) | 4 (30.8) | 4 (23.5) | 21 (22.8) |
| Grade 1 | 0 | 0 | 2 (15.4) | 1 (5.9) | 2 (18.2) | 1 (5.9) | 4 (30.8) | 4 (23.5) | 14 (15.2) |
| Grade 2 | 0 | 0 | 0 | 2 (11.8) | 2 (18.2) | 1 (5.9) | 0 | 0 | 5 (5.4) |
| Grade 3 | 0 | 0 | 1 (7.7) | 0 | 0 | 1 (5.9) | 0 | 0 | 2 (2.2) |

TABLE 5

Solicited Adverse Events by Grade and Treatment Group - Second Vaccination
(Second Vaccination Solicited Safety Set)

| | | hMPV/hPIV3 mRNA vaccine | | | | | | | |
|---|---|---|---|---|---|---|---|---|---|
| | | 25 µg | | 75 µg | | 150 µg | | 300 µg | |
| | Placebo (N = 28) n (%) | 2-Dose (N = 4) n (%) | 1-Dose (N = 12) n (%) | 2-Dose (N = 17) n (%) | 1-Dose (N = 13) n (%) | 2-Dose (N = 17) n (%) | 1-Dose (N = 11) n (%) | 2-Dose (N = 17) n (%) | Total (N = 94) n (%) |
| Solicited Local AEs | | | | | | | | | |
| Pain-N1 | 27 | 4 | 12 | 17 | 13 | 17 | 10 | 17 | 90 |
| Any | 4 (14.8) | 2 (50.0) | 2 (16.7) | 12 (70.6) | 4 (30.8) | 12 (70.6) | 1 (10.0) | 13 (76.5) | 46 (51.1) |
| Grade 1 | 3 (11.1) | 0 | 2 (16.7) | 6 (35.3) | 2 (15.4) | 7 (41.2) | 1 (10.0) | 7 (41.2) | 25 (27.8) |
| Grade 2 | 1 (3.7) | 2 (50.0) | 0 | 5 (29.4) | 2 (15.4) | 4 (23.5) | 0 | 5 (29.4) | 18 (20.0) |
| Grade 3 | 0 | 0 | 0 | 1 (5.9) | 0 | 1 (5.9) | 0 | 1 (5.9) | 3 (3.3) |
| Erythema (Redness)-N1 | 26 | 4 | 12 | 15 | 13 | 17 | 9 | 17 | 87 |
| Any | 1 (3.8) | 0 | 0 | 1 (6.7) | 0 | 1 (5.9) | 0 | 1 (5.9) | 3 (3.4) |
| Grade 1 | 0 | 0 | 0 | 1 (6.7) | 0 | 0 | 0 | 1 (5.9) | 2 (2.3) |
| Grade 2 | 0 | 0 | 0 | 0 | 0 | 1 (5.9) | 0 | 0 | 1 (1.1) |
| Grade 3 | 1 (3.8) | 0 | 0 | 0 | 0 | 0 | 0 | 0 | 0 |
| Swelling (Hardness)-N1 | 26 | 4 | 12 | 15 | 13 | 17 | 9 | 17 | 87 |
| Any | 0 | 0 | 0 | 2 (13.3) | 0 | 2 (11.8) | 0 | 1 (5.9) | 5 (5.7) |
| Grade 1 | 0 | 0 | 0 | 2 (13.3) | 0 | 2 (11.8) | 0 | 1 (5.9) | 5 (5.7) |
| Grade 2 | 0 | 0 | 0 | 0 | 0 | 0 | 0 | 0 | 0 |
| Grade 3 | 0 | 0 | 0 | 0 | 0 | 0 | 0 | 0 | 0 |
| Solicited Systemic AEs | | | | | | | | | |
| Fever-N1 | 28 | 4 | 12 | 17 | 13 | 17 | 11 | 17 | 91 |
| Any | 0 | 0 | 0 | 0 | 0 | 1 (5.9) | 0 | 2 (11.8) | 3 (3.3) |
| Grade 1 | 0 | 0 | 0 | 0 | 0 | 1 (5.9) | 0 | 0 | 1 (1.1) |
| Grade 2 | 0 | 0 | 0 | 0 | 0 | 0 | 0 | 1 (5.9) | 1 (1.1) |
| Grade 3 | 0 | 0 | 0 | 0 | 0 | 0 | 0 | 1 (5.9) | 1 (1.1) |
| Headache-N1 | 27 | 4 | 12 | 17 | 13 | 17 | 10 | 17 | 90 |
| Any | 2 (7.4) | 1 (25.0) | 1 (8.3) | 5 (29.4) | 4 (30.8) | 9 (52.9) | 1 (10.0) | 8 (47.1) | 29 (32.2) |
| Grade 1 | 1 (3.7) | 1 (25.0) | 1 (8.3) | 3 (17.6) | 4 (30.8) | 7 (41.2) | 0 | 5 (29.4) | 21 (23.3) |
| Grade 2 | 1 (3.7) | 0 | 0 | 2 (11.8) | 0 | 0 | 1 (10.0) | 3 (17.6) | 6 (6.7) |
| Grade 3 | 0 | 0 | 0 | 0 | 0 | 2 (11.8) | 0 | 0 | 2 (2.2) |
| Fatigue-N1 | 27 | 4 | 12 | 17 | 13 | 17 | 10 | 17 | 90 |
| Any | 2 (7.4) | 0 | 0 | 4 (23.5) | 4 (30.8) | 7 (41.2) | 3 (30.0) | 9 (52.9) | 27 (30.0) |
| Grade 1 | 1 (3.7) | 0 | 0 | 2 (11.8) | 2 (15.4) | 5 (29.4) | 2 (20.0) | 5 (29.4) | 16 (17.8) |
| Grade 2 | 1 (3.7) | 0 | 0 | 1 (5.9) | 2 (15.4) | 1 (5.9) | 1 (10.0) | 4 (23.5) | 9 (10.0) |
| Grade 3 | 0 | 0 | 0 | 1 (5.9) | 0 | 1 (5.9) | 0 | 0 | 2 (2.2) |
| Myalgia-N1 | 27 | 4 | 12 | 17 | 13 | 17 | 10 | 17 | 90 |
| Any | 2 (7.4) | 1 (25.0) | 1 (8.3) | 6 (35.3) | 2 (15.4) | 7 (41.2) | 1 (10.0) | 10 (58.8) | 28 (31.1) |
| Grade 1 | 2 (7.4) | 0 | 1 (8.3) | 4 (23.5) | 1 (7.7) | 4 (23.5) | 1 (10.0) | 5 (29.4) | 16 (17.8) |
| Grade 2 | 0 | 1 (25.0) | 0 | 1 (5.9) | 1 (7.7) | 2 (11.8) | 0 | 5 (29.4) | 10 (11.1) |
| Grade 3 | 0 | 0 | 0 | 1 (5.9) | 0 | 1 (5.9) | 0 | 0 | 2 (2.2) |
| Arthralgia-N1 | 27 | 4 | 12 | 17 | 13 | 17 | 10 | 17 | 90 |
| Any | 0 | 1 (25.0) | 1 (8.3) | 4 (23.5) | 2 (15.4) | 4 (23.5) | 1 (10.0) | 8 (47.1) | 21 (23.3) |
| Grade 1 | 0 | 0 | 1 (8.3) | 2 (11.8) | 2 (15.4) | 2 (11.8) | 1 (10.0) | 5 (29.4) | 13 (14.4) |
| Grade 2 | 0 | 1 (25.0) | 0 | 2 (11.8) | 0 | 1 (5.9) | 0 | 3 (17.6) | 7 (7.8) |
| Grade 3 | 0 | 0 | 0 | 0 | 0 | 1 (5.9) | 0 | 0 | 1 (1.1) |
| Nausea-N1 | 27 | 4 | 12 | 17 | 13 | 17 | 10 | 17 | 90 |
| Any | 1 (3.7) | 0 | 0 | 4 (23.5) | 0 | 4 (23.5) | 1 (10.0) | 5 (29.4) | 14 (15.6) |
| Grade 1 | 1 (3.7) | 0 | 0 | 4 (23.5) | 0 | 3 (17.6) | 1 (10.0) | 4 (23.5) | 12 (13.3) |
| Grade 2 | 0 | 0 | 0 | 0 | 0 | 1 (5.9) | 0 | 1 (5.9) | 2 (2.2) |
| Grade 3 | 0 | 0 | 0 | 0 | 0 | 0 | 0 | 0 | 0 |

Immunogenicity

All immunogenicity analyses were performed on the Per Protocol (PP) immunogenicity set, which included 118 of the 124 exposed subjects.

Baseline Neutralizing Antibody

Neutralizing antibodies against hMPV-A, hMPV-B, and PIV3 were present at baseline (Day 1, prior to vaccination) in all subjects (Table 6). The baseline geometric mean titer (GMT) of neutralizing antibodies was generally well balanced across treatment groups (Tables 7 and 8).

TABLE 6

Summary of Antibody Titers by Dose Group at Baseline (Day 1) (Per Protocol Immunogenicity Set)

| | | hMPV/hPIV3 mRNA vaccine | | | | | |
|---|---|---|---|---|---|---|---|
| | Placebo (N = 27) | 25 μg (N = 4) | 75 μg (N = 27) | 150 μg (N = 29) | 300 μg (N = 29) | Total (mRNA) (N = 89) | Total (N = 116) |
| hMPV-A | | | | | | | |
| Median | 3694.0 | 3068.0 | 3310.0 | 2931.0 | 4407.0 | 3488.0 | 3582.5 |
| Min, | 406, | 860, | 625, | 455, | 398, | 398, | 398, |
| max | 11806 | 6407 | 23216 | 11796 | 24084 | 24084 | 24084 |
| GMT | 2808.7 | 2464.9 | 2884.0 | 2974.8 | 3851.1 | 3178.6 | 3088.4 |
| 95% CI | 1964.9, 4014.9 | 537.9, 11294.8 | 1969.4, 4223.2 | 2250.0, 3933.2 | 2579.4, 5750.0 | 2617.5, 3860.0 | 2609.9, 3654.6 |
| hMPV-B | | | | | | | |
| Median | 4214.0 | 4352.5 | 5522.0 | 2793.0 | 4865.0 | 4178.0 | 4194.5 |
| Min, | 587, | 1786, | 177, | 688, | 590, | 177, | 177, |
| max | 23032 | 6042 | 562130 | 13138 | 236202 | 562130 | 562130 |
| GMT | 3518.8 | 3779.7 | 6337.0 | 2926.8 | 6213.7 | 4783.0 | 4453.2 |
| 95% CI | 2277.4, 5436.8 | 1641.1, 8705.1 | 3025.3, 13274.0 | 2133.5, 4015.0 | 3570.2, 10814.8 | 3533.6, 6474.1 | 3462.7, 5727.0 |
| PIV3 | | | | | | | |
| Median | 380.0 | 328.5 | 345.0 | 352.0 | 363.0 | 352.0 | 354.0 |
| Min, | 92, | 179, | 113, | 138, | 63, | 63, | 63, |
| max | 2692 | 791 | 3144 | 2302 | 2678 | 3144 | 3144 |
| GMT | 374.2 | 336.3 | 341.6 | 359.0 | 450.5 | 379.7 | 378.4 |
| 95% CI | 267.2, 523.9 | 108.3, 1043.9 | 251.4, 464.2 | 278.7, 462.5 | 303.9, 667.6 | 318.7, 452.3 | 324.7, 441.0 |

Figure 4A:
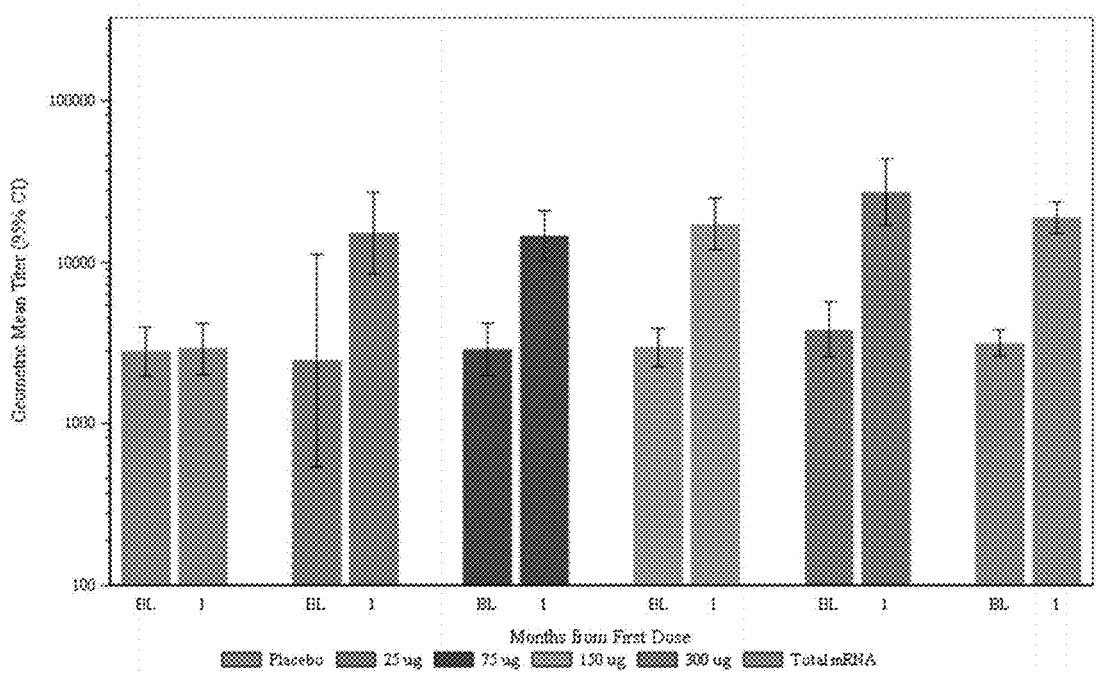
Figure 4B:
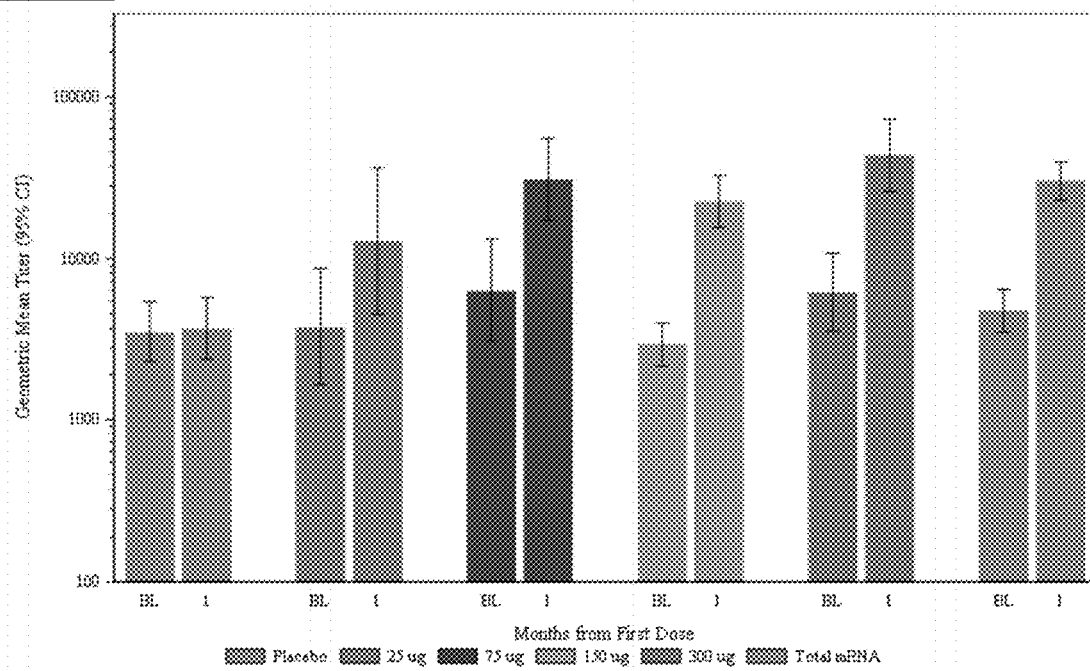
Figure 4C:
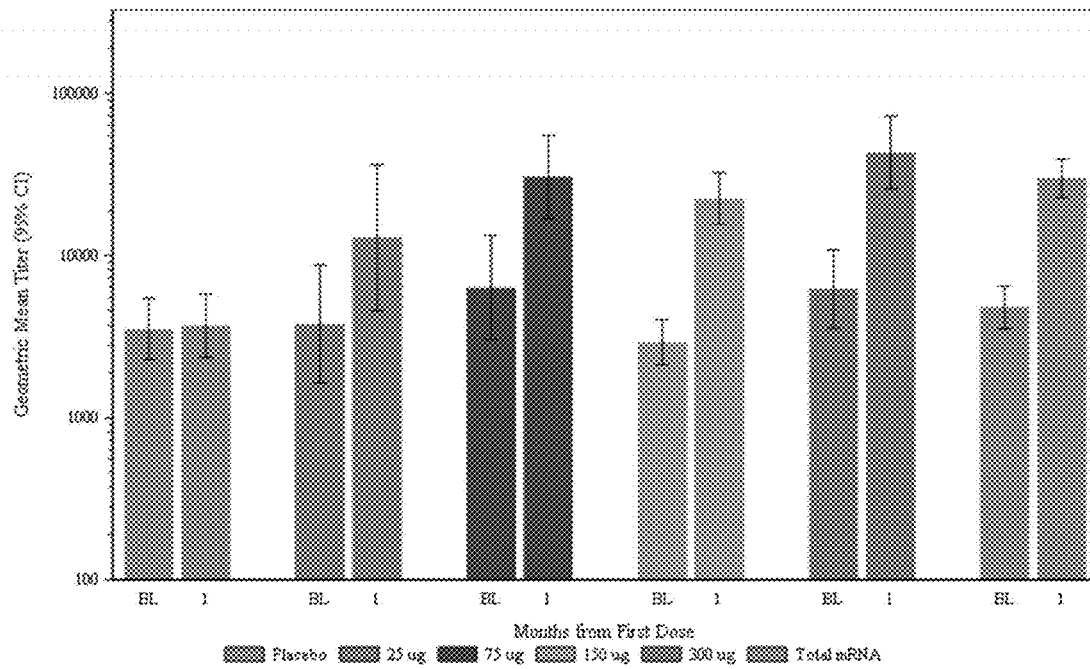
Figure 6:
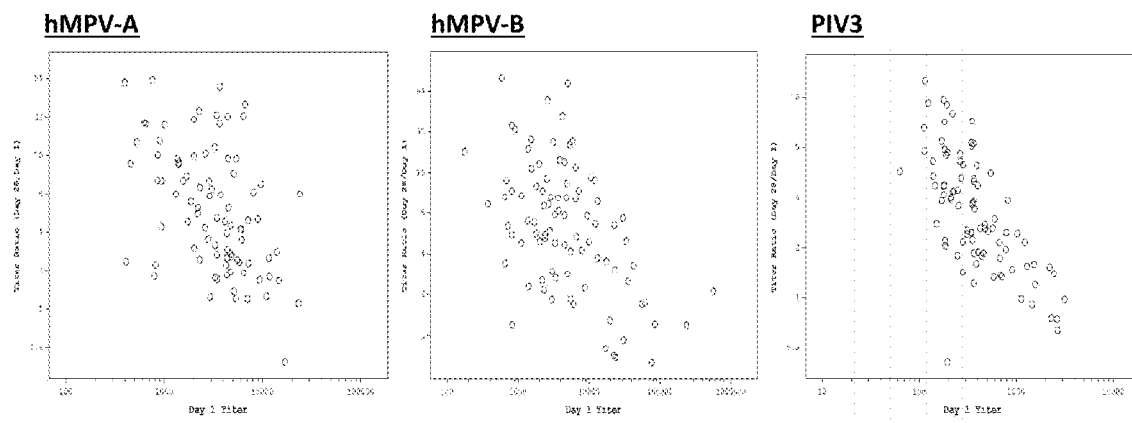
Figure 7A:
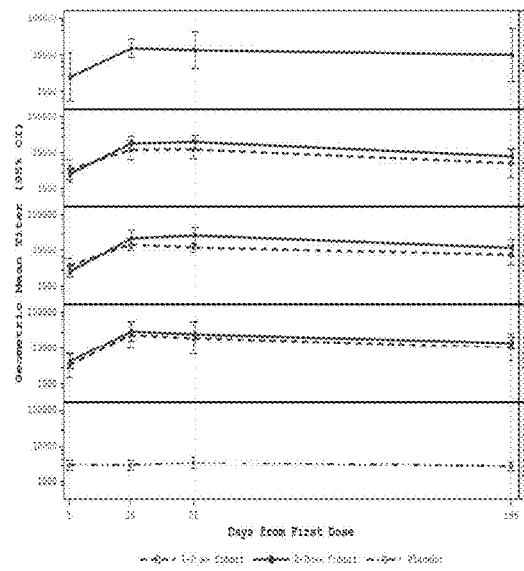
Figure 7B:
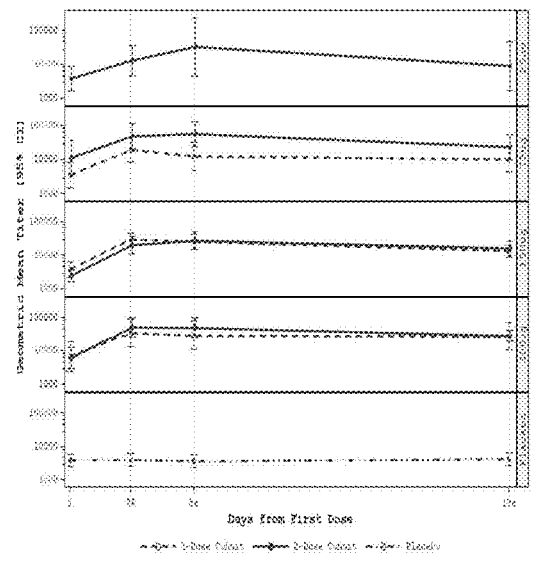
Figure 7C:
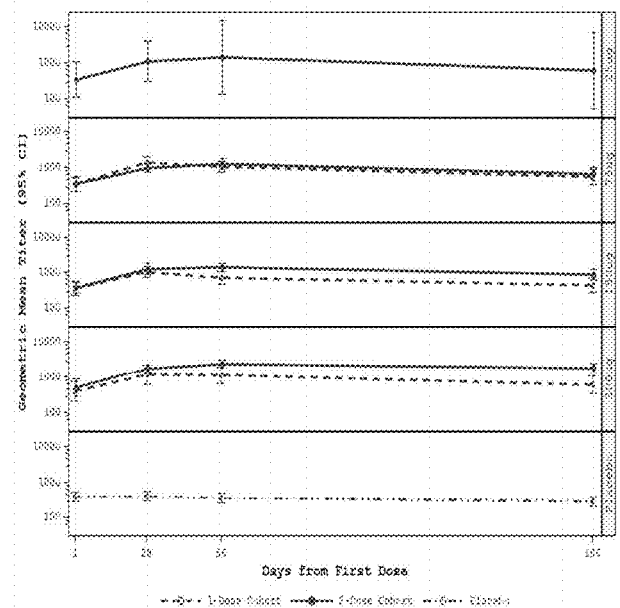

N = number of subjects who meet per protocol analysis at baseline (Day 1);
GMT—geometric mean titer;
CI—confidence interval Neutralizing Antibody Response to First Vaccination A single hMPV/hPIV3 mRNA vaccination boosted neutralizing antibody titers against hMPV (lineages A and B) and PIV3 at all dose levels tested (25, 75, 150 and 300 μg) with no apparent dose response (FIG. 4). As shown in Table 7, the Day 28 (Month 1) to baseline GMR in the 75, 150 and 300 μg dose groups ranged from 5.07-7.09 for hMPV-A, from 4.87-7.73 for hMPV-B, and from 3.13-3.36 for PIV3, and the Day 28 (Month 1) to baseline GMR for pooled hMPV/hPIV3 mRNA vaccination dose levels was 6.15 for hMPV-A, 6.36 for hMPV-B, and 3.29 for PIV3; and the seroresponse (percentage of subjects with >4× baseline titer) ranged from 51.9%-66.7% for hMPV-A, 59.3%-82.8% for hMPV-B, and 31.0%-51.7% for PIV3. A similar trend was observed in the 25 μg dose group of 4 subjects. There was an inverse relationship between baseline neutralizing antibody titer and the response to the first hMPV/hPIV3 mRNA vaccination (day 28/day 1 titer ratio), particularly for PIV3 (FIG. 6). Thus, the hMPV/hPIV3 mRNA vaccination tended to induce a greater boost in neutralizing antibody in subjects with lower baseline titers. There was no change in neutralizing antibody titer in the placebo group from baseline to Day 28, translating to a GMR ~1 and a 0% seroresponse, and suggesting absence of intercurrent hMPV or PIV3 infections during this time.

TABLE 7

Neutralizing Antibody by Dose Level and Visit Day; PP Immunogenicity Set

| | Placebo N = 28 | 25 μg N = 4 | 75 μg N = 27 | 150 μg N = 29 | 300 μg N = 29 | Total (mRNA) N = 89 |
|---|---|---|---|---|---|---|
| hMPV-A | | | | | | |
| Day 1 GMT | 2973.5 | 2464.9 | 2884.0 | 2974.8 | 3851.1 | 3178.6 |
| Day 28 GMT | 2967.1 | 15277.9 | 14617.9 | 17363.0 | 27306.8 | 19037.2 |
| Day 28 GMR | 1.00 | 8.52 | 5.07 | 5.84 | 7.09 | 6.04 |
| Day 28 SR | 0.0 | 66.7 | 51.9 | 62.1 | 65.5 | 60.2 |
| hMPV-B | | | | | | |
| Day 1 GMT | 3640.1 | 3779.7 | 6337.0 | 2926.8 | 6213.7 | 4783.0 |
| Day 28 GMT | 3777.9 | 12904.8 | 30881.2 | 22626.0 | 43579.7 | 30307.8 |
| Day 28 GMR | 1.04 | 3.53 | 4.87 | 7.73 | 7.01 | 6.33 |
| Day 28 SR | 0.0 | 66.7 | 59.3 | 82.8 | 62.1 | 68.2 |
| PIV3 | | | | | | |
| Day 1 GMT | 384.8 | 336.3 | 341.6 | 359.0 | 450.5 | 379.7 |
| Day 28 GMT | 396.6 | 1075.6 | 1149.3 | 1124.8 | 1482.0 | 1238.1 |

TABLE 7-continued

Neutralizing Antibody by Dose Level and Visit Day; PP Immunogenicity Set

|  | Placebo N = 28 | 25 μg N = 4 | 75 μg N = 27 | 150 μg N = 29 | 300 μg N = 29 | Total (mRNA) N = 89 |
|---|---|---|---|---|---|---|
| Day 28 GMR | 1.03 | 2.67 | 3.36 | 3.13 | 3.29 | 3.24 |
| Day 28 SR | 0.00 | 33.3 | 37.0 | 31.0 | 51.7 | 39.8 |

N = number of subjects who meet per protocol immunogenicity analysis definition at any timepoint;
GMT—geometric mean titer;
GMR—geometric mean ratio (post-baseline/baseline titer);
SR—seroresponse = percentage of subjects with >4 × baseline titer value at indicated time point.

Neutralizing Antibody Response to Second Vaccination

In the dose selection phase of the study, subjects in the 75 μg, 150 μg and 300 μg cohorts were randomly assigned in a 1:1 ratio to receive a second dose of the hMPV/hPIV3 mRNA vaccine (2-dose groups) or placebo (1-dose groups) on Day 28. Within any given dose level, the 1-dose and 2-dose cohorts might be expected to have similar GMT, GMR and seroresponse values at Day 28; however, this was not always the case. These differences are likely the result of smaller Ns when 1-dose and 2-dose cohorts are analyzed separately (N=12-17, Table 8), than when combined (N=28-29, Table 7).

Figure 5A:
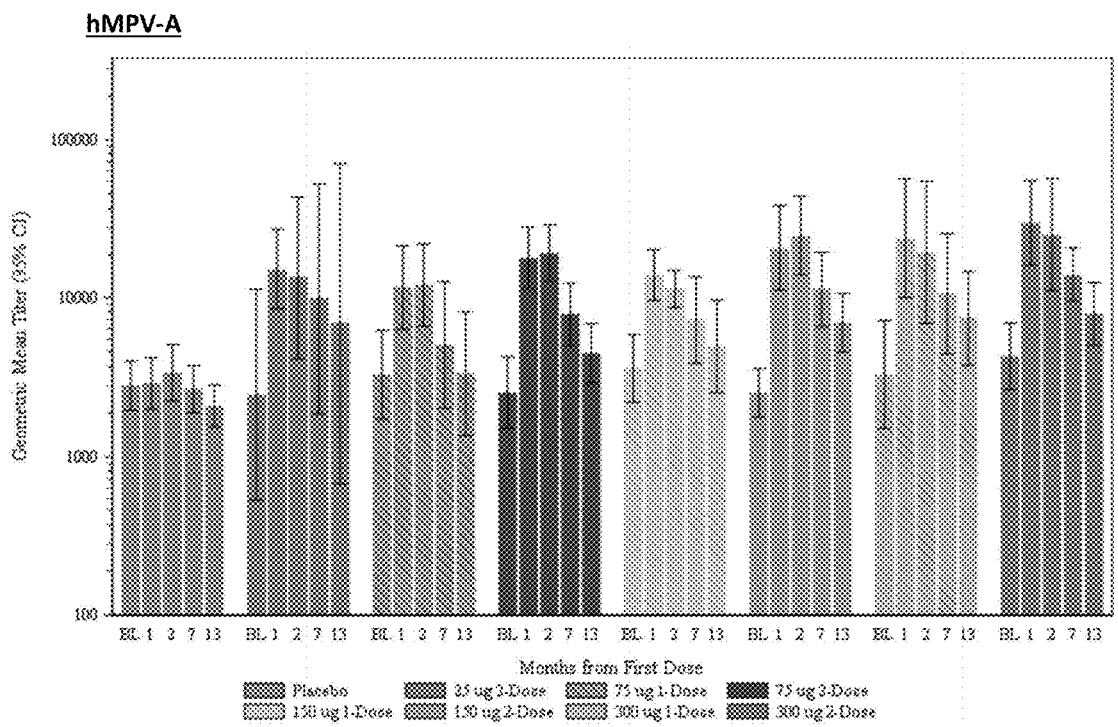
Figure 5B:
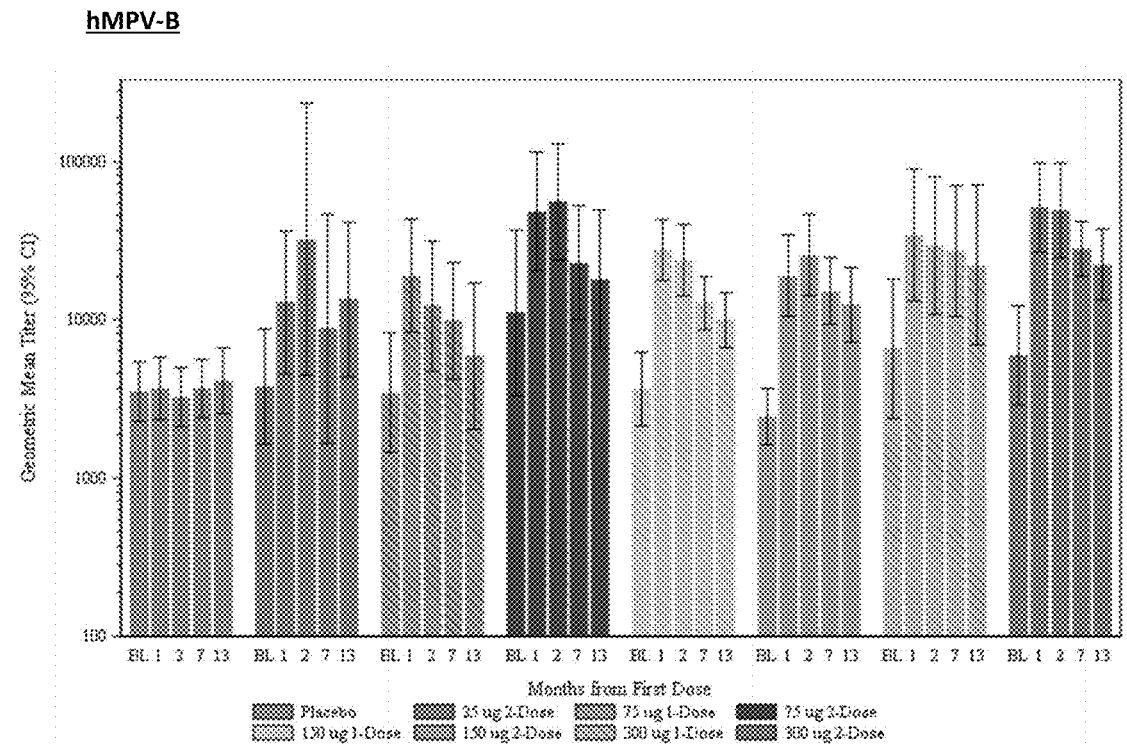
Figure 5C:
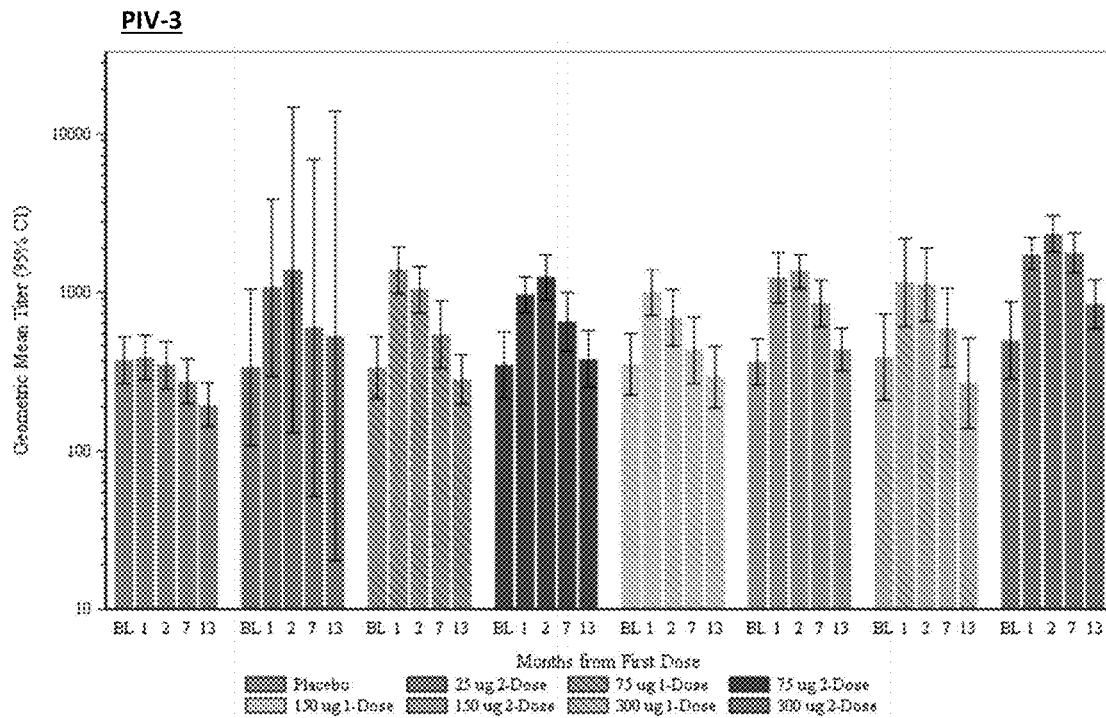

For the hMPV-A and hMPV-B neutralizing antibody titers, the 95% CIs for the GMR of the Month 2 titers to the Month 1 titers was approximately 1 for the comparison at all dose levels. For the PIV3 neutralizing antibody titer, the ratio of the Month 2 titers to the Month 1 titers was 1.51 for the 300 μg treatment group. This was the only treatment group for PIV3 where the 95% CI for the GMR excluded 1. This suggests that the second vaccination did not impact the hMPV or PIV3 neutralizing antibody titers over this timeframe (FIG. 5).

TABLE 8

Neutralizing Antibody by Dose Level, Regimen (1-dose vs. 2-dose) and Visit Day; PP Immunogenicity Set

|  |  | Placebo N = 28 | 25 μg 2-dose N = 4 | 75 μg 1-dose N = 13 | 75 μg 2-dose N = 14 | 150 μg 1-dose N = 13 | 150 μg 2-dose N = 16 | 300 μg 1-dose N = 12 | 300 μg 2-dose N = 17 |
|---|---|---|---|---|---|---|---|---|---|
| hMPV-A |  |  |  |  |  |  |  |  |  |
| GMT | Day 1 | 2973.5 | 2464.9 | 3301.1 | 2543.9 | 3611.8 | 2541.0 | 3302.5 | 4292.4 |
|  | Day 28 | 2967.1 | 15277.9 | 11715.6 | 17953.0 | 13964.7 | 20724.4 | 23915.5 | 29986.4 |
|  | Day 56 | 3468.4 | 13483.0 | 12094.3 | 19240.8 | 11491.6 | 24962.5 | 19443.0 | 25165.1 |
|  | Day 196 | 2738.9 | 9932.2 | 5052.2 | 7875.0 | 7265.7 | 11372.8 | 10687.1 | 14127.4 |
| GMR | Day 28 | 1.00 | 8.52 | 3.55 | 7.06 | 3.87 | 8.16 | 7.24 | 6.99 |
|  | Day 56 | 1.17 | 7.52 | 3.87 | 7.56 | 3.18 | 9.82 | 6.05 | 5.86 |
|  | Day 196 | 0.90 | 5.54 | 1.82 | 3.10 | 2.08 | 4.48 | 3.33 | 2.89 |
| SR | Day 28 | 0.00 | 66.7 | 38.5 | 64.3 | 53.8 | 68.8 | 66.7 | 64.7 |
|  | Day 56 | 0.00 | 66.7 | 33.3 | 71.4 | 30.8 | 81.3 | 45.5 | 70.6 |
|  | Day 196 | 0.00 | 66.7 | 27.3 | 35.7 | 25.0 | 62.5 | 45.5 | 37.5 |
| hMPV-B |  |  |  |  |  |  |  |  |  |
| GMT | Day 1 | 3640.1 | 3779.7 | 3468.4 | 11090.2 | 3650.9 | 2445.6 | 6605.1 | 5951.5 |
|  | Day 28 | 3777.9 | 12904.8 | 18980.2 | 48527.4 | 27912.8 | 19077.0 | 34427.8 | 51469.3 |
|  | Day 56 | 3433.1 | 32382.7 | 12248.9 | 56084.6 | 24023.6 | 25900.1 | 29411.2 | 49424.8 |
|  | Day 196 | 3905.5 | 8814.9 | 9894.8 | 23051.3 | 12785.3 | 15223.6 | 27230.9 | 28335.3 |
| GMR | Day 28 | 1.04 | 3.53 | 5.47 | 4.38 | 7.65 | 7.80 | 5.21 | 8.65 |
|  | Day 56 | 0.94 | 8.86 | 4.14 | 5.06 | 6.58 | 10.59 | 4.24 | 8.30 |
|  | Day 196 | 1.07 | 2.41 | 3.06 | 2.08 | 3.47 | 6.22 | 3.93 | 4.23 |
| SR | Day 28 | 0.00 | 66.7 | 69.2 | 50.0 | 76.9 | 87.5 | 58.3 | 64.7 |
|  | Day 56 | 0.00 | 66.7 | 41.7 | 50.0 | 76.9 | 93.8 | 45.5 | 76.5 |
|  | Day 196 | 0.00 | 0.00 | 27.3 | 21.4 | 33.3 | 68.8 | 45.5 | 50.0 |
| PIV3 |  |  |  |  |  |  |  |  |  |
| GMT | Day 1 | 384.8 | 336.3 | 335.5 | 347.4 | 352.3 | 364.6 | 391.3 | 497.5 |
|  | Day 28 | 396.6 | 1075.6 | 1385.5 | 966.2 | 1000.3 | 1237.3 | 1158.4 | 1763.5 |
|  | Day 56 | 356.2 | 1387.8 | 1044.4 | 1250.5 | 692.9 | 1361.9 | 1121.6 | 2369.4 |
|  | Day 196 | 280.2 | 599.1 | 541.3 | 651.2 | 431.8 | 849.0 | 599.0 | 1786.5 |
| GMR | Day 28 | 1.03 | 2.67 | 4.13 | 2.78 | 2.84 | 3.39 | 2.96 | 3.54 |
|  | Day 56 | 0.93 | 3.45 | 3.34 | 3.60 | 1.97 | 3.74 | 3.23 | 4.76 |
|  | Day 196 | 0.72 | 1.49 | 1.76 | 1.87 | 1.26 | 2.33 | 1.73 | 3.52 |

TABLE 8-continued

Neutralizing Antibody by Dose Level, Regimen (1-dose vs. 2-dose) and Visit Day; PP Immunogenicity Set

|  |  | Placebo<br>N = 28 | 25 μg<br>2-dose<br>N = 4 | 75 μg<br>1-dose<br>N = 13 | 75 μg<br>2-dose<br>N = 14 | 150 μg<br>1-dose<br>N = 13 | 150 μg<br>2-dose<br>N = 16 | 300 μg<br>1-dose<br>N = 12 | 300 μg<br>2-dose<br>N = 17 |
|---|---|---|---|---|---|---|---|---|---|
| SR | Day 28 | 0.00 | 33.3 | 46.2 | 28.6 | 23.1 | 37.5 | 50.0 | 52.9 |
|  | Day 56 | 0.00 | 33.3 | 8.3 | 35.7 | 23.1 | 56.3 | 36.4 | 58.8 |
|  | Day 196 | 0.00 | 0.00 | 9.1 | 21.4 | 0.00 | 18.8 | 18.2 | 43.8 |

N = number of subjects who meet per protocol immunogenicity analysis definition at any timepoint;
GMT—geometric mean titer;
GMR—geometric mean ratio (post-baseline/baseline titer);
SR—seroresponse = percentage of subjects with >4 × baseline titer value at corresponding time point.

Neutralizing Antibody Persistence

Persistence of the neutralizing antibody response was evaluated at Month 7 and Month 13. At Month 7, the neutralizing antibody GMT for all hMPV/hPIV3 mRNA vaccine dose levels was below the peak at Month 1 or Month 2 but remained above baseline. Across the hMPV/hPIV3 mRNA vaccine dose levels, the Month 7 GMR ranged from 2.45 to 5.54 for hMPV-A, 2.41 to 4.85 for hMPV B, and 1.49 to 2.63 for PIV3. The Month 7 GMR for the pooled hMPV/hPIV3 mRNA vaccine treatment groups was 2.98 for hMPV-A, 3.65 for hMPV-B, and 2.03 for PIV3.

At Month 13, the hMPV neutralizing antibody GMT for all hMPV/hPIV3 mRNA vaccine dose levels remained above baseline. Across dose levels, the GMR ranged from 1.50 to 3.88 for hMPV A and 1.18 to 3.82 for hMPV-B. The Month 13 GMR for the pooled hMPV/hPIV3 mRNA vaccine treatment groups was 1.87 for hMPV-A and 2.91 for hMPV-B. At Month 13, the PIV3 neutralizing antibody GMT had generally returned to baseline. Across dose levels the PIV3 GMR ranged from 0.97 to 1.32 for PIV3, and was 1.06 for the pooled hMPV/hPIV3 mRNA vaccine treatment groups.

The dose level and regimen did not have a major impact on the persistence of the neutralizing antibody response, although it is noted that the Month 7 and Month 13 GMT was greatest in the 300 μg treatment group for neutralizing antibodies against hMPV (both A and B lineages) and neutralizing antibodies against PIV3.

There was no increase in neutralizing antibody titer in the placebo group from baseline to Month 7, reflected by a GMR ~1 and a 0% seroresponse, and suggesting absence of intercurrent hMPV or PIV3 infections during this time. This was also true for hMPV-A at Month 13. However, there was one subject in the placebo group for both hMPV-B and PIV3 with a seroresponse at Month 13.

Example 2. A Phase 1b, Randomized, Observer-Blind, Placebo-Controlled, Dose-Ranging Trial to Evaluate the Safety and Immunogenicity of a Combined Human Metapneumovirus (hMPV) and Parainfluenza Virus Type 3 (PIV3) Vaccine when Administered to Adults, and to Children 12-36 Months of Age with Serologic Evidence of Prior Exposure Scientific Rationale for Study Design The design and dose levels proposed for this Phase 1b are based on observations described in Example 1. Based on interim analysis to date, the hMPV/hPIV3 mRNA vaccine was generally well-tolerated in adults. No serious adverse events (SAEs), adverse events (AEs) of special interest, or AEs leading to withdrawal were reported. There was no pattern of clinically relevant laboratory abnormalities across treatment groups. Neutralizing antibodies against hMPV and PIV3 were present at baseline in all participants, consistent with prior exposure to both viruses.

Figure 8:
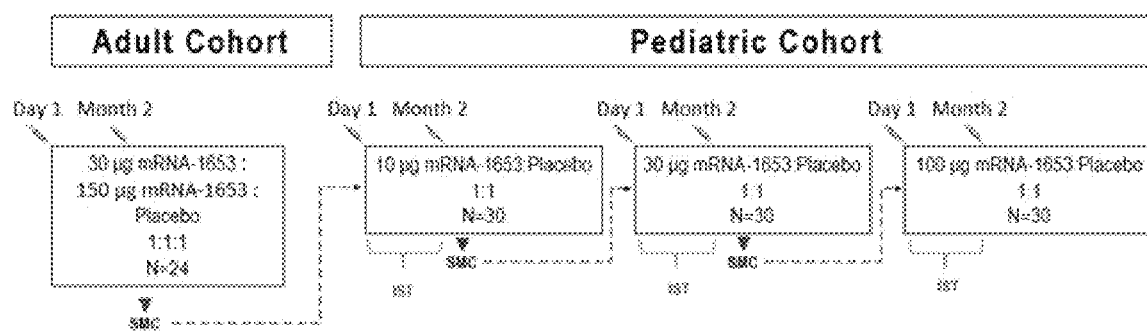

The Phase 1b study evaluates 3 dose levels of the hMPV/hPIV3 mRNA vaccine for safety and immunogenicity in seropositive hMPV and PIV3 children 12 to 36 months of age using a dose escalation design and is intended to support the progression to evaluation in seronegative children if tolerated in the seropositive children. See FIG. 8. A lead-in cohort in healthy adults is also included to confirm the safety profile observed in Example 1.

The safety and tolerability of the hMPV/hPIV3 mRNA vaccine is first evaluated in 15 participants 12-36 months of age at the lowest dose level of 10 μg before sequential escalation to the planned higher dose levels of 30 and 100 μg. Enrollment of successive dose level cohorts follows Safety Monitoring Committee (SMC) review and oversight in each instance.

Justification for the Choice of Study Population

The purpose of this study is to assess the safety and immunogenicity of the hMPV/hPIV3 mRNA vaccine in children 12-36 months of age corresponding to a pediatric population closer in age to the primary target population where the disease burden still exists, however generally considered to be less severe than in the very young infants. In an abundance of caution, participants are selected to be doubly seropositive to hMPV and PIV3 by microneutralization assay prior trial enrollment, to initiate the pediatric development in children who have had previous infection of both hMPV and PIV3.

A lead-in cohort in healthy adults is also included to confirm the safety profile observed in Example 1 in support of the implementation of a minor manufacturing process change in the hMPV/hPIV3 mRNA vaccine.

Justification for the Dose and Schedule

In the Phase 1b study, the 2 dose levels of the hMPV/hPIV3 mRNA vaccine tested in adults are 30 μg (corresponding to one dose intended to be tested in children), and 150 μg for comparison with one dose previously tested in Example 1.

The dose range being tested in the toddlers in the Phase 1b study has been selected based on the results of Example 1 and corresponds to a multiplying factor of approximately 3 starting with the lowest dose. The lowest dose level in the Phase 1b trial at 10 μg is lower than the lowest level of 25 μg tested in Example 1, considering that young children or infants reactogenicity may be more limiting.

Study Design

This is a Phase 1b, randomized, observer-blind, placebo-controlled, dose-ranging trial. The safety profile of the Adult Cohort permits enrollment of the Pediatric Cohort. The Adult Cohort comprises healthy adults 18-49 years of age randomized in parallel 1:1:1 who receive one of 2 dose levels of the hMPV/hPIV3 mRNA vaccine or placebo. The Pediatric Cohort comprises healthy children 12-36 months of age randomized sequentially into 3 increasing dose levels of the hMPV/hPIV3 mRNA vaccine, with each dose level randomized in a 1:1 ratio who receive the hMPV/hPIV3 mRNA vaccine or placebo. A 2-vaccination, 0, 2-month schedule is administered to all participants at all dose levels. The treatment dose levels are as follows:

Adult Cohort

Approximately 24 participants are randomized 1:1:1 to receive either 30 µg of hMPV/hPIV3 mRNA vaccine, 150 µg of hMPV/hPIV3 mRNA vaccine, or placebo.

Pediatric Cohort (enrolled sequentially following safety assessment post second vaccination before escalation to the next dose level):

Dose Level 1: 30 participants is randomized 1:1 to receive either 10 µg of hMPV/hPIV3 mRNA vaccine or placebo.

Dose Level 2: 30 participants is randomized 1:1 to receive either 30 µg of hMPV/hPIV3 mRNA vaccine or placebo.

Dose Level 3: 30 participants is randomized 1:1 to receive either 100 µg of hMPV/hPIV3 mRNA vaccine or placebo.

The primary purpose of this trial is to assess the safety and immunogenicity of the hMPV/hPIV3 mRNA vaccine in adults and pediatric participants with serologic evidence of prior exposure to hMPV and PIV3. The dose levels of the hMPV/hPIV3 mRNA vaccine are based on the safety and immunogenicity profile of the vaccine in the Phase 1 trial (Example 1). Enrollment into the trial begins with an Adult Cohort followed by enrollment of a Pediatric Cohort.

Number of Participants:

Approximately 24 adults and 90 children 12-36 months of age (114 total).

Inclusion Criteria:

Adult and pediatric participants are eligible to be included in the study. Adults 18-49 years of age and children 12-36 months of age.

Exclusion Criteria:

Adult and pediatric participants eligible for this study must not meet any of the following criteria: (1) Acutely ill or febrile (2) History of a diagnosis or condition that may affect trial assessment or compromise participant safety, specifically: Congenital or acquired immunodeficiency, including human immunodeficiency virus (HIV) infection. Chronic hepatitis, or suspected active hepatitis. A bleeding disorder that is considered a contraindication to IM injection or phlebotomy. Dermatologic conditions that could affect local solicited AR assessments. Allergic or anaphylactic reactions following a vaccination that required medical intervention. Febrile seizures or recent receipt of inactivated vaccines or live virus vaccines or undergoing systemic immunosuppression.

Investigational Product, Dosage, and Mode of Administration:

The hMPV/hPIV3 mRNA vaccine injection consists of 2 distinct mRNA sequences that encode the full-length membrane-bound F proteins of hMPV and PIV3. The 2 mRNA Drug Substances are formulated at a target mass ratio of 1:1 in a mixture of 4 lipids to form a drug lipid complex LNP. The 4 lipids are heptadecan-9-yl 8-((2-hydroxyethyl)(6-oxo-6(undecyloxy)hexyl)amino)octanoate (ionizable cationic lipid); 1,2-dimyristoyl-sn-glycerol, methoxypolyethyleneglycol (PEG2000-DMG); 1,2-distearoyl-sn-glycero-3-phosphocholine (DSPC); and cholesterol.

The hMPV/hPIV3 mRNA vaccine injection is provided in 2-mL glass vials as a sterile liquid for injection and stored until use.

Estimated Study Duration:

Adult participants are followed for up to approximately 8 months (approximately 6 months after the last vaccination). Pediatric participants are followed for up to approximately 13 months (approximately 11 months after the last vaccination).

Reference Therapy, Dosage, and Mode of Administration:

Placebo consisting of a 0.9% sodium chloride (saline) injection is administered intramuscularly.

Criteria for Evaluation:

Safety Assessments

In adult participants, solicited local adverse reactions (ARs) of injection site pain, erythema (redness), and swelling/induration (hardness), and solicited systemic ARs of fever, headache, fatigue, myalgia, arthralgia, nausea/vomiting, chills and rash are assessed. Solicited local and systemic ARs occurring during the 7 days following each vaccination (the day of vaccination and 6 subsequent days) are recorded by the participant via an electronic Diary (eDiary).

In pediatric participants, solicited local ARs of tenderness, erythema (redness) and swelling/induration (hardness), and solicited systemic ARs of fever, sleepiness, loss of appetite, chills/shivering, irritability/fussiness/persistent crying and rash are assessed. Solicited local and systemic ARs occurring during the 7 days following each vaccination (i.e., the day of vaccination and 6 subsequent days) are recorded.

Immunogenicity Assessments

GMT of serum anti-hMPV and anti-PIV3 neutralizing antibodies and GMR of post-baseline/baseline titers.

Proportion of participants with ≥2-fold and ≥4-fold increases in serum anti-hMPV or anti-PIV3 neutralizing antibody titer from baseline.

Exploratory assays to characterize the immune response to hMPV, PIV3 or other respiratory viruses are performed with excess serum.

Sequences

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

(SEQ ID NO: 3)
5' UTR: GGGAAAUAAGAGAGAAAAGAAGAGUAAGAAGAAAUAUAAGAGCCACC (SEQ ID NO: 4)
5' UTR: GGGAAAUAAGAGAGAAAAGAAGAGUAAGAAGAAAUAUAAGACCCCGGCGCCGCCACC (SEQ ID NO: 5)
3' UTR: UGAUAAUAGGCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC (SEQ ID NO: 6)
3' UTR: UGAUAAUAGGCUGGAGCCUCGGUGGCCUAGCUUCUUGCCCCUUGGGCCUCCCCCCAGCCCCUCCUCCCCUUCCUGCACCCGUACCCCCGUGGUCUUUGAAUAAAGUCUGAGUGGGCGGC

| hMPV F Glycoprotein | | SEQ ID NO: |
|---|---|---|
| SEQ ID NO: 1 consists of from 5' end to 3' end, 5' UTR SEQ ID NO: 3, mRNA ORF SEQ ID NO: 7, and 3' UTR SEQ ID NO: 5. | | 1 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 3 |
| ORF of mRNA Construct (excluding the stop codon) | AUGAGCUGGAAGGUGGUGAUUAUCUUCAGCCUGCUGAUU ACACCUCAACACGGCCUGAAGGAGAGCUACCUGGAAGAG AGCUGCUCCACCAUCACCGAGGGCUACCUGAGCGUGCUGC GGACCGGCUGGUACACCAACGUGUUCACCCUGGAGGUGG GCGACGUGGAGAACCUGACCUGCAGCGACGGCCCUAGCC UGAUCAAGACCGAGCUGGACCUGACCAAGAGCGCUCUGA GAGAGCUGAAGACCGUGUCCGCCGACCAGCUGGCCAGAG AGGAACAGAUCGAGAACCCUCGGCAGAGCAGAUUCGUGC UGGGCGCCAUCGCUCUGGGAGUCGCCGCUGCCGCUGCAG UGACAGCUGGAGUGGCCAUUGCUAAGACCAUCAGACUGG AAAGCGAGGUGACAGCCAUCAACAAUGCCCUGAAGAAGA CCAACGAGGCCGUGAGCACCCUGGGCAAUGGAGUGAGAG UGCUGGCCACAGCCGUGCGGGAGCUGAAGGACUUCGUGA GCAAGAACCUGACCAGAGCCAUCAACAAGAACAAGUGCG ACAUCGAUGACCUGAAGAUGGCCGUGAGCUUCUCCCAGU UCAACAGACGGUUCCUGAACGUGGUGAGACAGUUCUCCG ACAACGCUGGAAUCACACCUGCCAUUAGCCUGGACCUGA UGACCGACGCCGAGCUGGCUAGAGCCGUGCCCAACAUGCC CACCAGCGCUGGCCAGAUCAAGCUGAUGCUGGAGAACAG AGCCAUGGUGCGGAGAAAGGGCUUCGGCAUCCUGAUUGG GGUGUAUGGAAGCUCCGUGAUCUACAUGGUGCAGCUGCC CAUCUUCGGCGUGAUCGACACACCCUGCUGGAUCGUGAA GGCCGCUCCUAGCUGCUCCGAGAAGAAAGGAAACUAUGC CUGUCUGCUGAGAGAGGACCAGGGCUGGUACUGCCAGAA CGCCGGAAGCACAGUGUACUAUCCCAACGAGAAGGACUG CGAGACCAGAGGCGACCACGUGUUCUGCGACACCGCUGCC GGAAUCAACGUGGCCGAGCAGAGCAAGGAGUGCAACAUC AACAUCAGCACAACCAACUACCCCUGCAAGGUGAGCACCG GACGGCACCCCAUCAGCAUGGUGGCUCUGAGCCCUCUGG GCGCUCUGGUGGCCUGCUAUAAGGGCGUGUCCUGUAGCA UCGGCAGCAAUCGGGUGGGCAUCAUCAAGCAGCUGAACA AGGGAUGCUCCUACAUCACCAACCAGGACGCCGACACCGU GACCAUCGACAACACCGUGUACCAGCUGAGCAAGGUGGA GGGCGAGCAGCACGUGAUCAAGGGCAGACCCGUGAGCUC CAGCUUCGACCCCAUCAAGUUCCCUGAGGACCAGUUCAAC GUGGCCCUGGACCAGGUGUUUGAGAACAUCGAGAACAGC CAGGCCCUGGUGGACCAGAGCAACAGAAUCCUGUCCAGC GCUGAAGGGCAACACCGGCUUCAUCAUUGUGAUCAUU CUGAUCGCCGUGCUGGGCAGCUCCAUGAUCCUGGUGAGC AUCUUCAUCAUUAUCAAGAAGACCAAGAAACCCACCGGA GCCCCUCCUGAGCUGAGCGGCGUGACCAACAAUGGCUUC AUUCCCCACAACUGA | 7 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCGUGGUCUUUGAAUAAAGUCUGAGUGGGCGG C | 5 |
| Corresponding amino acid sequence | MSWKVVIIFSLLITPQHGLKESYLEESCSTITEGYLSVLRTGWY TNVFTLEVGDVENLTCSDGPSLIKTELDLTKSALRELKTVSAD QLAREEQIENPRQSRFVLGAIALGVAAAAAVTAGVAIAKTIRL ESEVTAINNALKKTNEAVSTLGNGVRVLATAVRELKDFVSKN LTRAINKNKCDIDDLKMAVSFSQFNRRFLNVVRQFSDNAGITP AISLDLMTDAELARAVPNMPTSAGQIKLMLENRAMetVRRKG FGILIGVYGSSVIYMVQLPIFGVIDTPCWIVKAAPSCSEKKGNY ACLLREDQGWYCQNAGSTVYYPNEKDCETRGDHVFCDTAA GINVAEQSKECNINISTTNYPCKVSTGRHPISMVALSPLGALVA CYKGVSCSIGSNRVGIIKQLNKGCSYITNQDADTVTIDNTVYQ LSKVEGEQHVIKGRPVSSSFDPIKFPEDQFNVALDQVFENIENS QALVDQSNRILSSAEKGNTGFIIVIILIAVLGSSMILVSIF IIIKKTKKPTGAPPELSGVTNNGFIPHN | 8 |
| PolyA tail | 100 nt | |

-continued

| hPIV3 F Glycoprotein | | SEQ ID NO: |
|---|---|---|
| SEQ ID NO: 2 consists of from 5' end to 3' end, 5' UTR SEQ ID NO: 3, mRNA ORF SEQ ID NO: 9, and 3' UTR SEQ ID NO: 5. | | 2 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGAGCCACC | 3 |
| ORF of mRNA Construct (excluding the stop codon) | AUGCCCAUCAGCAUCCUGCUGAUCAUCACCACAAUGAUC<br>AUGGCCAGCCACUGCCAGAUCGACAUCACCAAGCUGCAGC<br>ACGUGGGCGUGCUCGUGAACAGCCCCAAGGGCAUGAAGA<br>UCAGCCAGAACUUCGAGACACGCUACCUGAUCCUGAGCC<br>UGAUCCCCAAGAUCGAGGACAGCAACAGCUGCGGCGACC<br>AGCAGAUCAAGCAGUACAAGCGGCUGCUGGACAGACUGA<br>UCAUCCCCCUGUACGACGGCCUGCGGCUGCAGAAAGACG<br>UGAUCGUGACCAACCAGGAAAGCAACGAGAACACCGACC<br>CCCGGACCGAGAGAUUCUUCGGCGGCGUGAUCGGCACAA<br>UCGCCCUGGGAGUGGCCACAAGCGCCCAGAUUACAGCCGC<br>UGUGGCCCUGGUGGAAGCCAAGCAGGCCAGAAGCGACAU<br>CGAGAAGCUGAAAGAGGCCAUCCGGGACACCAACAAGGC<br>CGUGCAGAGCGUGCAGUCCAGCGUGGGCAAUCUGAUCGU<br>GGCCAUCAAGUCCGUGCAGGACUACGUGAACAAAGAAAU<br>CGUGCCCUCUAUCGCCCGGCUGGGCUGUGAAGCUGCCGG<br>ACUGCAGCUGGGCAUUGCCCUGACACAGCACUACAGCGA<br>GCUGACCAACAUCUUCGGCGACAACAUCGGCAGCCUGCA<br>GGAAAAGGGCAUUAAGCUGCAGGGAAUCGCCAGCCUGUA<br>CCGCACCAACAUCACCGAGAUCUUCACCACCAGCACCGUG<br>GAUAAGUACGACAUCUACGACCUGCUGUUCACCGAGAGC<br>AUCAAAGUGCGCGUGAUCGACGUGGACCUGAACGACUAC<br>AGCAUCACCCUGCAAGUGCGGCUGCCCCUGCUGACCAGAC<br>UGCUGAACACCCAGAUCUACAAGGUGGACAGCAUCUCCU<br>ACAACAUCCAGAACCGCGAGUGGUACAUCCCUCUGCCCAG<br>CCACAUUAUGACCAAGGGCGCCUUUCUGGGCGGAGCCGA<br>CGUGAAAGAGUGCAUCGAGGCCUUCAGCAGCUACAUCUG<br>CCCCAGCGACCCUGGCUUCGUGCUGAACCACGAGAUGGA<br>AAGCUGCCUGAGCGGCAACAUCAGCCAGUGCCCCAGAACC<br>ACCGUGACCUCCGACAUCGUGCCCAGAUACGCCUUCGUGA<br>AUGGCGGCGUGGUGGCCAACUGCAUCACCACCACCUGUA<br>CCUGCAACGGCAUCGGCAACCGGAUCAACCAGCCUCCCGA<br>UCAGGGCGUGAAGAUUAUCACCCACAAAGAGUGUAACAC<br>CAUCGGCAUCAACGGCAUGCUGUUCAAUACCAACAAAGA<br>GGGCACCCUGGCCUUCUACACCCCCGACGAUAUCACCCUG<br>AACAACUCCGUGGCUCUGGACCCCAUCGACAUCUCCAUCG<br>AGCUGAACAAGGCCAAGAGCGACCUGGAAGAGUCCAAAG<br>AGUGGAUCCGGCGGAGCAACCAGAAGCUGGACUCUAUCG<br>GCAGCUGGCACCAGAGCAGCACCACCAUCAUCGUGAUCCU<br>GAUUAUGAUGAUUAUCCUGUUCAUCAUCAACAUUACCAU<br>CAUCACUAUCGCCAUUAAGUACUACCGGAUCCAGAAACG<br>GAACCGGGUGGACCAGAAUGACAAGCCCUACGUGCUGAC<br>AAACAAG | 9 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 5 |
| Corresponding amino acid sequence | MPISILLIITTMIMASHCQIDITKLQHVGVLVNSPKGMKISQNFE<br>TRYLILSLIPKIEDSNSCGDQQIKQYKRLLDRLIIPLYDGLRLQK<br>DVIVTNQESNENTDPRTERFFGGVIGTIALGVATSAQITAAVAL<br>VEAKQARSDIEKLKEAIRDTNKAVQSVQSSVGNLIVAIKSVQD<br>YVNKEIVPSIARLGCEAAGLQLGIALTQHYSELTNIFGDNIGSL<br>QEKGIKLQGIASLYRTNITEIFTTSTVDKYDIYDLLFTESIKVRV<br>IDVDLNDYSITLQVRLPLLTRLLNTQIYKVDSISYNIQNREWYI<br>PLPSHIMTKGAFLGGADVKECIEAFSSYICPSDPGFVLNHEMES<br>CLSGNISQCPRTTVTSDIVPRYAFVNGGVVANCITTTCTCNGIG<br>NRINQPPDQGVKIITHKECNTIGINGMLFNTNKEGTLAFYTPDD<br>ITLNNSVALDPIDISIELNKAKSDLEESKEWIRRSNQKLDSIGSW<br>HQSSTTIIVILIMMIILFIINITIITIAIKYYRIQKRNRVDQND<br>KPYVLTNK | 10 |
| PolyA tail | 100 nt | |

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean ±10% of the recited numerical value.

Where a range of values is provided, each value between the upper and lower ends of the range are specifically contemplated and described herein.

The entire contents of International Application Nos. PCT/US2015/02740, PCT/US2016/043348, PCT/US2016/043332, PCT/US2016/058327, PCT/US2016/058324, PCT/US2016/058314, PCT/US2016/058310, PCT/US2016/058321, PCT/US2016/058297, PCT/US2016/058319, and PCT/US2016/058314 are incorporated herein by reference.

What is claimed is:

1. A method of inducing in a human subject human metapneumovirus (hMPV) and human parainfluenza virus 3 (hPIV3) neutralizing antibody titers, the method comprising administering to the human subject a vaccine composition comprising:

(a) an mRNA comprising a nucleic acid sequence having at least 95% identity to the nucleic acid sequence of SEQ ID NO: 1; and (b) an mRNA comprising a nucleic acid sequence having at least 95% identity to the nucleic acid sequence of SEQ ID NO: 2, wherein the mRNA of (a) and the mRNA of (b) are in a lipid nanoparticle (LNP).

2. The method of claim 1, wherein the vaccine composition comprises a 25 μg to 150 μg dose of mRNA.

3. The method of claim 2, wherein the vaccine composition comprises a 150 μg dose of mRNA.

4. The method of claim 1, wherein the vaccine composition comprises a 25 μg to 75 μg dose of mRNA.

5. The method of claim 4, wherein the vaccine composition comprises a 75 μg dose of mRNA.

6. The method of claim 4, wherein the vaccine composition comprises a 25 μg dose of mRNA.

7. The method of claim 1, wherein the lipid nanoparticle comprises 45-55 mole percent (mol %) ionizable cationic lipid, 5-15 mol % non-cationic lipid, 35-40 mol % sterol, and 1-2 mol % PEG-modified lipid.

8. The method of claim 7, wherein the lipid nanoparticle comprises 50 mol % Compound I ionizable cationic lipid, 10 mol % DSPC (1,2-Distearoyl-sn-glycero-3-phosphocholine), 38.5 mol % cholesterol, and 1.5 mol % DMG-PEG (1,2-dimyristoyl-rac-glycero-3-methoxypolyethylene glycol-2000), wherein Compound I has the formula:

9. The method of claim 1, wherein the nucleotide sequence of the mRNA of (a) encodes an hMPV F glycoprotein comprising the amino acid sequence of SEQ ID NO: 8.

10. The method of claim 1, wherein the nucleotide sequence of the mRNA of (b) encodes an hPIV3 F glycoprotein comprising the amino acid sequence of SEQ ID NO: 10.

11. The method of claim 1, wherein the mRNA of (a) comprises an open reading frame sequence having at least 95% identity to the nucleic acid sequence of SEQ ID NO: 7 and encodes an hMPV glycoprotein F.

12. The method of claim 11, wherein the mRNA of (a) comprises an open reading frame sequence that comprises the nucleic acid sequence of SEQ ID NO: 7 and encodes an hMPV glycoprotein F.

13. The method of claim 1, wherein the mRNA of (b) comprises an open reading frame sequence having at least 95% identity to the nucleic acid sequence of SEQ ID NO: 9 and encodes an hPIV3 glycoprotein F.

14. The method of claim 13, wherein the mRNA encoding the hPIV3 glycoprotein comprises an open reading frame sequence that comprises the nucleic acid sequence of SEQ ID NO: 9 and encodes an hPIV3 glycoprotein F.

15. The method of claim 1, wherein the mRNA of (a) comprises the nucleic acid sequence of SEQ ID NO: 1.

16. The method of claim 1, wherein the mRNA of (b) comprises the nucleic acid sequence of SEQ ID NO: 2.

17. A method of inducing in a human subject human metapneumovirus (hMPV) and human parainfluenza virus 3 (hPIV3) neutralizing antibody titers, the method comprising administering to the human subject a vaccine composition comprising a 25 μg to 150 μg dose of messenger ribonucleic acid (mRNA) formulated in a lipid nanoparticle (LNP), wherein the mRNA comprises mRNA encoding an hMPV fusion (F) glycoprotein comprising the amino acid sequence of SEQ ID NO: 8 and mRNA encoding an hPIV3 F glycoprotein comprising the amino acid sequence of SEQ ID NO: 10, wherein the lipid nanoparticle comprises 45-55 mole percent (mol %) Compound I ionizable cationic lipid, 5-15 mol % DSPC, 35-40 mol % cholesterol, and 1-2 mol % DMG-PEG, and the geometric mean titer (GMT) of hMPV neutralizing antibodies and hPIV3 neutralizing antibodies induced in the subject is increased by at least 3-fold within 30 days of administering the vaccine composition, relative to baseline, and wherein Compound I has the formula:

18. The method of claim 17, wherein the mRNA encoding the hMPV glycoprotein comprises an open reading frame sequence having at least 95% identity to the nucleic acid sequence of SEQ ID NO: 7, and the mRNA encoding the hPIV3 glycoprotein comprises an open reading frame sequence having at least 95% identity to the nucleic acid sequence of SEQ ID NO: 9.

* * * * *